US011400344B2

(12) United States Patent
Foley et al.

(10) Patent No.: US 11,400,344 B2
(45) Date of Patent: Aug. 2, 2022

(54) EXERCISE SYSTEM AND METHOD

(71) Applicant: Peloton Interactive, Inc., New York, NY (US)

(72) Inventors: John Foley, New York, NY (US); Thomas Cortese, Brooklyn, NY (US); Yu Feng, New York, NY (US); Hisao Kushi, Santa Monica, CA (US); Maureen C. Coiro, Brooklyn, NY (US); Anthony Moschella, Brooklyn, NY (US); Jason Poure, Hastings on Hudson, NY (US); Joseph Intonato, Brooklyn, NY (US)

(73) Assignee: Peloton Interactive, Inc., New York, NY (US)

( * ) Notice: Subject to any disclaimer, the term of this patent is extended or adjusted under 35 U.S.C. 154(b) by 46 days.

(21) Appl. No.: 17/120,928

(22) Filed: Dec. 14, 2020

(65) Prior Publication Data
US 2021/0093921 A1    Apr. 1, 2021

Related U.S. Application Data

(63) Continuation of application No. 15/686,875, filed on Aug. 25, 2017, now Pat. No. 10,864,406.
(Continued)

(51) Int. Cl.
*A63B 24/00* (2006.01)
*A63B 22/02* (2006.01)
(Continued)

(52) U.S. Cl.
CPC ...... *A63B 24/0075* (2013.01); *A63B 22/0023* (2013.01); *A63B 22/025* (2015.10);
(Continued)

(58) Field of Classification Search
CPC ............ A63B 24/0075; A63B 22/0023; A63B 22/025; A63B 23/0405; A63B 23/1227;
(Continued)

(56) References Cited

U.S. PATENT DOCUMENTS 3,976,192 A    8/1976  Muller
4,591,147 A    5/1986  Smith et al.
(Continued)

FOREIGN PATENT DOCUMENTS

CN         2877780        3/2007
CN       101766891        7/2010
(Continued)

OTHER PUBLICATIONS

Chinese Office Action dated May 20, 2020 for Chinese Patent Application No. 201780066713.X, a counterpart of U.S. Appl. No. 15/686,875, 12 pages.
(Continued)

*Primary Examiner* — Garrett K Atkinson
(74) *Attorney, Agent, or Firm* — Haynes and Boone, LLP

(57) ABSTRACT

An exercise machine includes a processor, a first display, a deck, and a belt rotatable about the deck. The machine also includes a sensor operably connected to the processor and configured to detect a first performance parameter of a first user running on the belt of the exercise machine. The processor is configured to receive information indicative of a second performance parameter of a second user, the second performance parameter being detected at an additional exercise machine during display of the at least part of the exercise class on a display associated with the additional exercise machine. The processor is also configured to cause the second performance parameter to be displayed on the first display together with the first performance parameter.

20 Claims, 35 Drawing Sheets

Related U.S. Application Data

(60) Provisional application No. 62/380,412, filed on Aug. 27, 2016.

(51) Int. Cl.
  *A63B 22/00* (2006.01)
  *A63B 23/04* (2006.01)
  *A63B 23/12* (2006.01)
  *A63B 71/06* (2006.01)

(52) U.S. Cl.
  CPC ...... *A63B 23/0405* (2013.01); *A63B 23/1227* (2013.01); *A63B 24/0062* (2013.01); *A63B 71/0616* (2013.01); *A63B 71/0622* (2013.01); *A63B 2024/0081* (2013.01); *A63B 2071/065* (2013.01); *A63B 2071/0625* (2013.01); *A63B 2071/0658* (2013.01); *A63B 2071/0675* (2013.01); *A63B 2071/0694* (2013.01); *A63B 2225/20* (2013.01)

(58) Field of Classification Search
  CPC ............ A63B 24/0062; A63B 71/0616; A63B 71/0622; A63B 2024/0081; A63B 2071/0625; A63B 2071/065; A63B 2071/0658; A63B 2071/0675; A63B 2071/0694; A63B 2225/20; A63B 24/0084; A63B 24/0087; A63B 21/072; A63B 21/0726; A63B 2225/12; G16H 20/30
  See application file for complete search history.

(56) References Cited

U.S. PATENT DOCUMENTS

| | | | |
|---|---|---|---|
| 4,614,337 | A | 9/1986 | Schonenberger |
| 4,771,148 | A | 9/1988 | Bersonnet |
| D303,414 | S | 9/1989 | Armstrong et al. |
| 5,029,801 | A | 7/1991 | Dalebout et al. |
| 5,104,120 | A | 4/1992 | Watterson et al. |
| D330,399 | S | 10/1992 | Furline |
| 5,178,594 | A | 1/1993 | Wu |
| 5,336,145 | A | 8/1994 | Keiser |
| 5,441,468 | A | 8/1995 | Deckers et al. |
| 5,458,548 | A | 10/1995 | Crossing et al. |
| 5,547,439 | A | 8/1996 | Rawls et al. |
| 5,656,000 | A | 8/1997 | Russell |
| 5,947,868 | A * | 9/1999 | Dugan ................. A63F 13/211 482/4 |
| 5,984,838 | A | 11/1999 | Wang et al. |
| 5,989,161 | A | 11/1999 | Wang et al. |
| 6,042,514 | A | 3/2000 | Abelbeck |
| 6,050,924 | A | 4/2000 | Shea |
| 6,171,218 | B1 | 1/2001 | Shea |
| 6,231,482 | B1 | 5/2001 | Thompson |
| 6,409,633 | B1 | 6/2002 | Abelbeck |
| 6,471,622 | B1 | 10/2002 | Hammer et al. |
| 6,601,016 | B1 | 7/2003 | Brown et al. |
| 6,626,803 | B1 | 9/2003 | Oglesby et al. |
| 6,648,798 | B2 | 11/2003 | Yoo |
| 6,695,751 | B1 | 2/2004 | Hsu |
| 6,702,719 | B1 | 3/2004 | Brown et al. |
| 6,749,536 | B1 | 6/2004 | Cuskaden et al. |
| 6,764,430 | B1 | 7/2004 | Fencel |
| 6,830,541 | B2 | 12/2004 | Wu |
| 6,899,659 | B2 | 5/2005 | Anderson et al. |
| 6,902,513 | B1 * | 6/2005 | McClure ............ A63B 24/0006 482/4 |
| 6,923,746 | B1 | 8/2005 | Skowronski et al. |
| 6,984,193 | B2 | 1/2006 | Chen |
| 6,997,853 | B1 | 2/2006 | Cuskaden et al. |
| 7,153,241 | B2 | 12/2006 | Wang |
| 7,252,624 | B2 | 8/2007 | Wu et al. |
| 7,455,620 | B2 | 11/2008 | Frykman et al. |
| 7,562,761 | B2 | 7/2009 | Tasma et al. |
| 7,594,878 | B1 | 9/2009 | Joannou |
| 7,618,352 | B1 | 11/2009 | Wei |
| D606,599 | S | 12/2009 | Murray et al. |
| 7,628,730 | B1 | 12/2009 | Watterson et al. |
| 7,746,997 | B2 | 6/2010 | Brunson |
| 7,927,253 | B2 * | 4/2011 | Vincent .................. H04B 1/385 482/8 |
| 8,001,472 | B2 * | 8/2011 | Gilley ................... A63B 22/02 715/834 |
| 8,012,067 | B2 | 9/2011 | Joannou |
| 8,348,813 | B2 | 1/2013 | Huang |
| 8,376,910 | B2 | 2/2013 | Cheung |
| 8,545,369 | B2 | 10/2013 | Cheung |
| 8,579,767 | B2 * | 11/2013 | Ellis ..................... H04W 12/02 482/901 |
| 8,608,624 | B2 | 12/2013 | Shabodyash et al. |
| 8,829,376 | B2 | 9/2014 | Wei |
| 8,986,169 | B2 | 3/2015 | Bayerlein et al. |
| 9,174,085 | B2 * | 11/2015 | Foley ..................... A63B 22/06 |
| 9,254,411 | B1 | 2/2016 | Chang |
| 9,452,314 | B2 | 9/2016 | Hou |
| 9,452,315 | B1 | 9/2016 | Murray et al. |
| 9,463,349 | B1 | 10/2016 | Chang |
| 9,579,544 | B2 | 2/2017 | Watterson |
| 9,613,659 | B2 * | 4/2017 | Maser ................. G09B 19/0038 |
| 9,616,278 | B2 | 4/2017 | Olson |
| 9,623,285 | B1 | 4/2017 | Ruiz |
| 9,636,567 | B2 * | 5/2017 | Brammer ............. A63B 71/0622 |
| 9,649,528 | B2 | 5/2017 | Hou |
| 9,675,839 | B2 | 6/2017 | Dalebout et al. |
| 9,682,307 | B2 | 6/2017 | Dalebout |
| 9,694,234 | B2 | 7/2017 | Dalebout et al. |
| 9,694,242 | B2 | 7/2017 | Ashby et al. |
| 9,713,742 | B2 | 7/2017 | Pasini et al. |
| 9,767,785 | B2 | 9/2017 | Ashby et al. |
| 9,808,672 | B2 | 11/2017 | Dalebout |
| 9,814,929 | B2 | 11/2017 | Moser |
| 9,814,930 | B2 | 11/2017 | Manzke et al. |
| 10,009,644 | B2 * | 6/2018 | Aimone ............ H04N 21/43072 |
| 10,010,748 | B1 | 7/2018 | Weinstein et al. |
| 2002/0091627 | A9 | 7/2002 | Yang |
| 2003/0093248 | A1 * | 5/2003 | Vock ..................... A42B 3/0433 702/188 |
| 2003/0199366 | A1 | 10/2003 | Anderson et al. |
| 2004/0102931 | A1 * | 5/2004 | Ellis ..................... H04W 4/029 702/188 |
| 2004/0121884 | A1 | 6/2004 | Chang |
| 2004/0166995 | A1 | 8/2004 | Wu |
| 2005/0054490 | A1 | 3/2005 | Chou |
| 2005/0137062 | A1 | 6/2005 | Kuokkanen |
| 2005/0239601 | A1 | 10/2005 | Thomas |
| 2006/0058160 | A1 | 3/2006 | Lee et al. |
| 2006/0136173 | A1 * | 6/2006 | Case ..................... G09B 19/003 702/182 |
| 2006/0207867 | A1 | 9/2006 | Waddington |
| 2007/0072743 | A1 | 3/2007 | Severino et al. |
| 2007/0105693 | A1 | 5/2007 | Wang |
| 2007/0116207 | A1 | 5/2007 | Brunson |
| 2007/0219059 | A1 * | 9/2007 | Schwartz ............ A61B 5/02405 482/8 |
| 2007/0281831 | A1 | 12/2007 | Wang |
| 2008/0076637 | A1 * | 3/2008 | Gilley ................. G06Q 30/0201 482/9 |
| 2008/0086318 | A1 * | 4/2008 | Gilley ................. G16H 10/20 705/319 |
| 2008/0116036 | A1 | 5/2008 | Tasma et al. |
| 2008/0242511 | A1 | 10/2008 | Munoz et al. |
| 2009/0098524 | A1 | 4/2009 | Walton |
| 2009/0233771 | A1 * | 9/2009 | Quatrochi .......... A63B 71/0622 434/247 |
| 2010/0048358 | A1 * | 2/2010 | Tchao ..................... G06F 3/016 482/8 |
| 2010/0160115 | A1 | 6/2010 | Morris et al. |
| 2011/0082008 | A1 | 4/2011 | Cheung |
| 2011/0082011 | A1 | 4/2011 | Ellis |
| 2011/0190097 | A1 | 8/2011 | Daly et al. |
| 2011/0306911 | A1 | 12/2011 | Tran |

(56) References Cited

U.S. PATENT DOCUMENTS

| | | | |
|---|---|---|---|
| 2012/0088633 | A1 | 4/2012 | Crafton |
| 2013/0125025 | A1 | 5/2013 | Cheung |
| 2013/0237374 | A1 | 9/2013 | Ashby |
| 2013/0267386 | A1 | 10/2013 | Her |
| 2013/0281241 | A1 | 10/2013 | Watterson et al. |
| 2014/0038781 | A1 | 2/2014 | Foley et al. |
| 2014/0082526 | A1 | 3/2014 | Park et al. |
| 2014/0172135 | A1* | 6/2014 | Eisner .............. A63K 3/00 700/91 |
| 2014/0223462 | A1* | 8/2014 | Aimone .......... H04N 21/4788 725/10 |
| 2014/0280219 | A1* | 9/2014 | Maser .............. G06F 16/739 707/748 |
| 2015/0182800 | A1 | 7/2015 | Watterson |
| 2015/0190671 | A1 | 7/2015 | Golen, Jr. et al. |
| 2015/0238817 | A1 | 8/2015 | Watterson et al. |
| 2015/0273272 | A1 | 10/2015 | Wang |
| 2016/0023045 | A1 | 1/2016 | Dalebout |
| 2016/0023049 | A1 | 1/2016 | Dalebout |
| 2016/0103970 | A1 | 4/2016 | Liu et al. |
| 2016/0129311 | A1 | 5/2016 | Yang |
| 2016/0166877 | A1 | 6/2016 | Cei et al. |
| 2016/0170436 | A1 | 6/2016 | Farrar et al. |
| 2016/0181028 | A1 | 6/2016 | Ebrom et al. |
| 2016/0199695 | A1 | 7/2016 | Armstrong |
| 2016/0287930 | A1 | 10/2016 | Moser |
| 2017/0186444 | A1 | 6/2017 | Lu |
| 2017/0281079 | A1 | 10/2017 | Nachman |
| 2017/0326411 | A1 | 11/2017 | Watterson |
| 2017/0333751 | A1 | 11/2017 | Seol |
| 2017/0340917 | A1 | 11/2017 | Chang |
| 2018/0056132 | A1 | 3/2018 | Foley et al. |
| 2018/0126248 | A1* | 5/2018 | Dion .................. A63B 23/1227 |
| 2018/0126249 | A1* | 5/2018 | Consiglio ............ A63B 22/025 |
| 2018/0140903 | A1 | 5/2018 | Poure et al. |
| 2019/0111318 | A1* | 4/2019 | Evancha ............ A63B 24/0075 |
| 2019/0143194 | A1* | 5/2019 | Evancha ............ A63B 24/0062 482/4 |
| 2020/0015736 | A1 | 1/2020 | Alhathal |

FOREIGN PATENT DOCUMENTS

| | | |
|---|---|---|
| CN | 105409145 A | 3/2016 |
| CN | 205595259 U | 9/2016 |
| CN | 206544889 U | 10/2017 |
| EP | 0919259 | 6/1999 |
| EP | 2964349 | 1/2016 |
| TW | I644706 | 12/2018 |
| WO | WO199741925 | 11/1997 |
| WO | WO2005087323 | 9/2005 |
| WO | WO 2017/209500 | 12/2017 |
| WO | WO 2019/143488 | 7/2019 |

OTHER PUBLICATIONS

"CompuTrainer", Racermate, 2017, retrieved Nov. 30, 2018 from <<http://www.racermateinc.com/computrainer/>>, 3 pages.

Extended European Search Report dated Apr. 1, 2020 for European Patent Application No. 17847265.0, 8 pages.

"Netathlon", WebRacing, 2014, retrieved Nov. 30, 2018 from <<http://webracinginc.com/products_netathlon.htm>>, 3 pages.

Non Final Office Action dated Sep. 9, 2019 for U.S. Appl. No. 15/863,368 "Exercise System and Method" Consiglio, 33 pages.

Non Final Office Action dated Sep. 18, 2019 for U.S. Appl. No. 15/686,875 "Exercise System and Method" Foley, 10 pages.

Final Office Action dated Nov. 16, 2020 for U.S. Appl. No. 15/863,057, "Exercise System and Method", Dion, 26 pages.

Office Action for U.S. Appl. No. 15/863,596, dated Nov. 29, 2019, Poure, Exercise System and Method, 21 Pages.

Non Final Office Action dated Nov. 30, 2020 for U.S. Appl. No. 15/863,596, "Exercise System and Method", Poure, 28 pages.

Non Final Office Action dated Mar. 19, 2020 for U.S. Appl. No. 15/863,057 "Exercise System and Method" Dion, 20 pages.

Final Office Action dated Apr. 14, 2020 for U.S. Appl. No. 15/863,368 "Exercise System and Method" Consiglio, 33 pages.

Final Office Action dated Apr. 29, 2020 for U.S. Appl. No. 15/686,875 "Exercise System and Method" Foley, 7 pages.

Final Office Action dated Jun. 12, 2020 for U.S. Appl. No. 15/863,596 "Exercise System and Method" Poure, 25 pages.

PCT Search Report and Written Opinion dated Dec. 13, 2017, for PCT Application No. PCT/US2017/48650, 14 pages.

PCT Search Report and Written Opinion dated May 1, 2019 for PCT Application No. PCT/US2019/012321, 12 pages.

\* cited by examiner

EXERCISE SYSTEM AND METHOD

CROSS-REFERENCE TO RELATED APPLICATIONS

This application is a continuation of U.S. application Ser. No. 15/686,875, filed Aug. 25, 2017, which is a nonprovisional of U.S. Provisional Application No. 62/380,412, filed Aug. 27, 2016, the entire disclosures of which are incorporated herein by reference.

FIELD OF THE INVENTION

This application relates generally to the field of exercise equipment and methods associated therewith. In particular, this application relates to an exercise system and method configured to provide streaming and on-demand exercise classes to one or more users.

BACKGROUND

Humans are competitive by nature, striving to improve their performance both as compared to their own prior efforts and as compared to others. Humans are also drawn to games and other diversions, such that even tasks that a person may find difficult or annoying can become appealing if different gaming elements are introduced. Existing home and gym-based exercise systems and methods frequently lack key features that allow participants to compete with each other, converse with each other, and that gamify exercise activities.

While some existing exercise equipment incorporates diversions such as video displays that present content or performance data to the user while they exercise, these systems lack the ability to truly engage the user in a competitive or gaming scenario that improves both the user's experience and performance. Such systems also lack the ability to facilitate real-time sharing of information, conversation, data, and/or other content between users, as well as between an instructor and one or more users.

To improve the experience and provide a more engaging environment, gyms offer exercise classes such as aerobics classes, yoga classes, or other classes in which an instructor leads participants in a variety of exercises. Such class-based experiences, however, are accessible only at specific times and locations. As a result, they are unavailable to many potential users, generally are very expensive, and often sell-out so that even users in a location convenient to the gym cannot reserve a class. Example embodiments of the present disclosure address these problems, providing an exercise machine, embodied by an example treadmill, that incorporates multimedia inputs and outputs for live streaming or archived instructional content, socially networked audio and video chat, networked performance metrics and competition capabilities, along with a range of gamification features.

SUMMARY OF THE INVENTION

In an example embodiment of the present disclosure, a method includes providing information about available exercise classes to a processor associated with a first exercise machine, the first exercise machine being located at a first remote location, receiving, from a first user of the first exercise machine and via the processor, a selection of one of the available exercise classes, and providing, via a network and to the processor, digital content comprising the one of the available exercise classes. Such an example method also includes receiving, via the network, a first plurality of performance parameters detected at the first exercise machine during display of at least part of the one of the available exercise classes on a display associated with the first exercise machine, the at least part of the one of the available exercise classes requiring participants to run on a treadmill. Such an example method further includes receiving, via the network, a second plurality of performance parameters detected at a second exercise machine during display of the at least part of the one of the available exercise classes on a display associated with the second exercise machine, the second exercise machine being located at a second remote location different from the first remote location. The method also includes providing, via the network, at least one parameter of the second plurality of performance parameters to the processor. In such methods, the processor is configured to cause the at least one parameter of the second plurality of performance parameters to be displayed on the display associated with the first exercise machine together with a corresponding at least one parameter of the first plurality of performance parameters.

In another example embodiment of the present disclosure, an exercise machine includes a processor, a first display operably connected to the processor and configured to display content, a deck configured to move relative to a surface supporting the exercise machine, and a belt rotatable about the deck. Such an example exercise machine also includes a sensor operably connected to the processor. The sensor is configured to detect a first performance parameter of a first user running on the belt of the exercise machine during display of at least part of an exercise class on the first display. In such embodiments, the processor is configured to receive, via a network, information indicative of a second performance parameter of a second user, the second performance parameter being detected at an additional exercise machine during display of the at least part of the exercise class on a display associated with the additional exercise machine, the additional exercise machine being located at location remote from the exercise machine. In such embodiments, the processor is also configured to cause the second performance parameter to be displayed on the first display together with the first performance parameter.

In a further example embodiment of the present disclosure, a method includes causing at least part of an exercise class to be displayed on a first display associated with a first treadmill, and receiving information indicative of a first performance parameter detected by a sensor associated with the first treadmill, the first performance parameter being associated with a first user running on a belt of the first treadmill during display of the at least part of the exercise class on the first display. Such an example method also includes receiving, via a network, information indicative of a second performance parameter associated with a second user, the second performance parameter being detected at a second treadmill during display of the at least part of the exercise class on a second display associated with the second treadmill, the second treadmill being located at location remote from the first treadmill. Such a method further includes causing the second performance parameter to be displayed on the first display together with the first performance parameter.

BRIEF DESCRIPTION OF THE DRAWINGS

The detailed description is described with reference to the accompanying figures. In the figures, the left-most digit of a reference number identifies the figure in which the reference number first appears. The same reference numbers in different figures indicate similar or identical items.

FIG. 12 illustrates an example user interface of the present disclosure including information related to featured exercise classes.

FIG. 13 illustrates another example user interface of the present disclosure including information related to featured exercise classes.

FIG. 14 illustrates a further example user interface of the present disclosure including information related to a class library.

DETAILED DESCRIPTION

Figure 1:
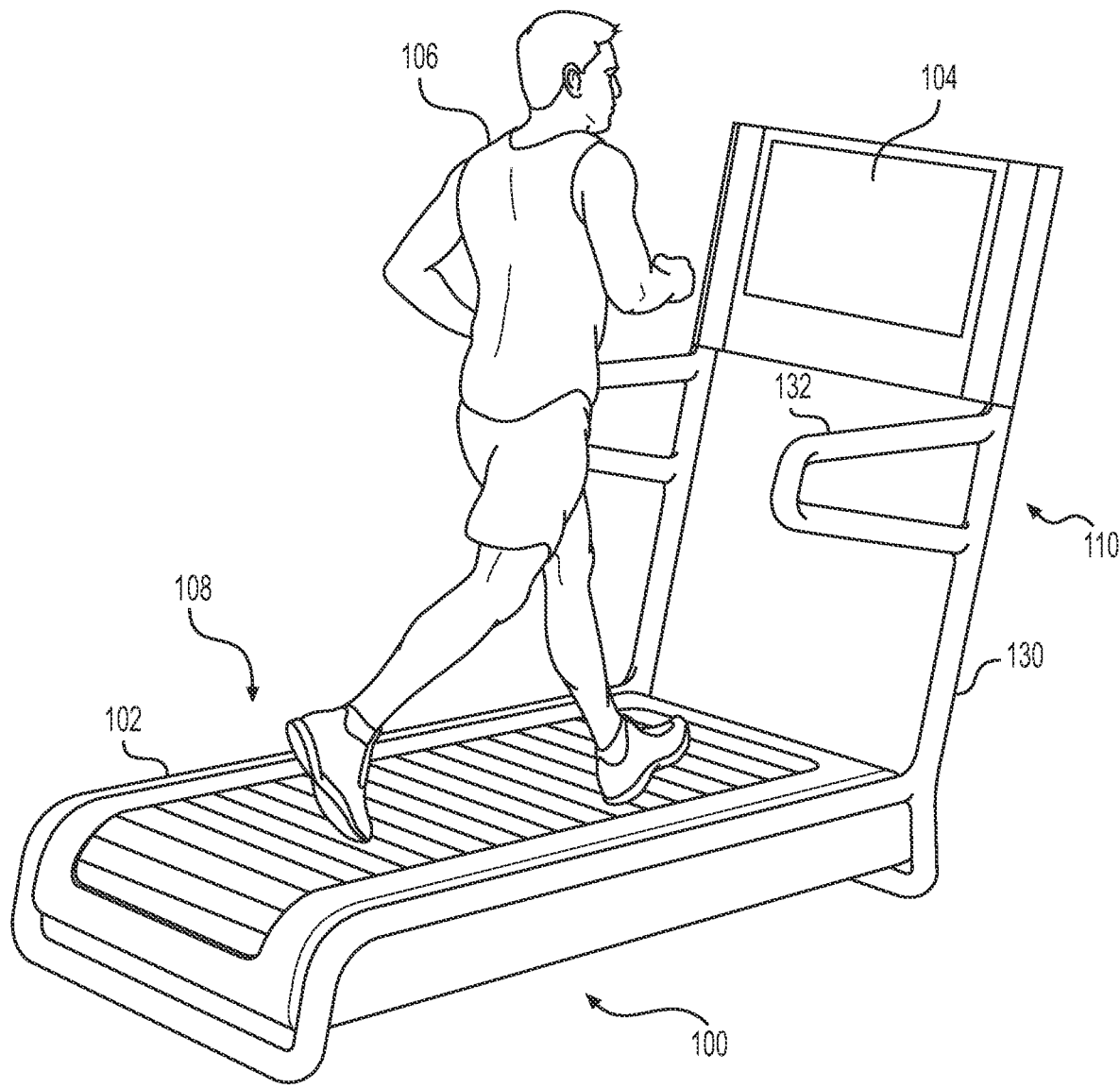
FIG. 1 is a rear perspective view of an exemplary exercise machine as disclosed herein with a user shown.
Figure 2:
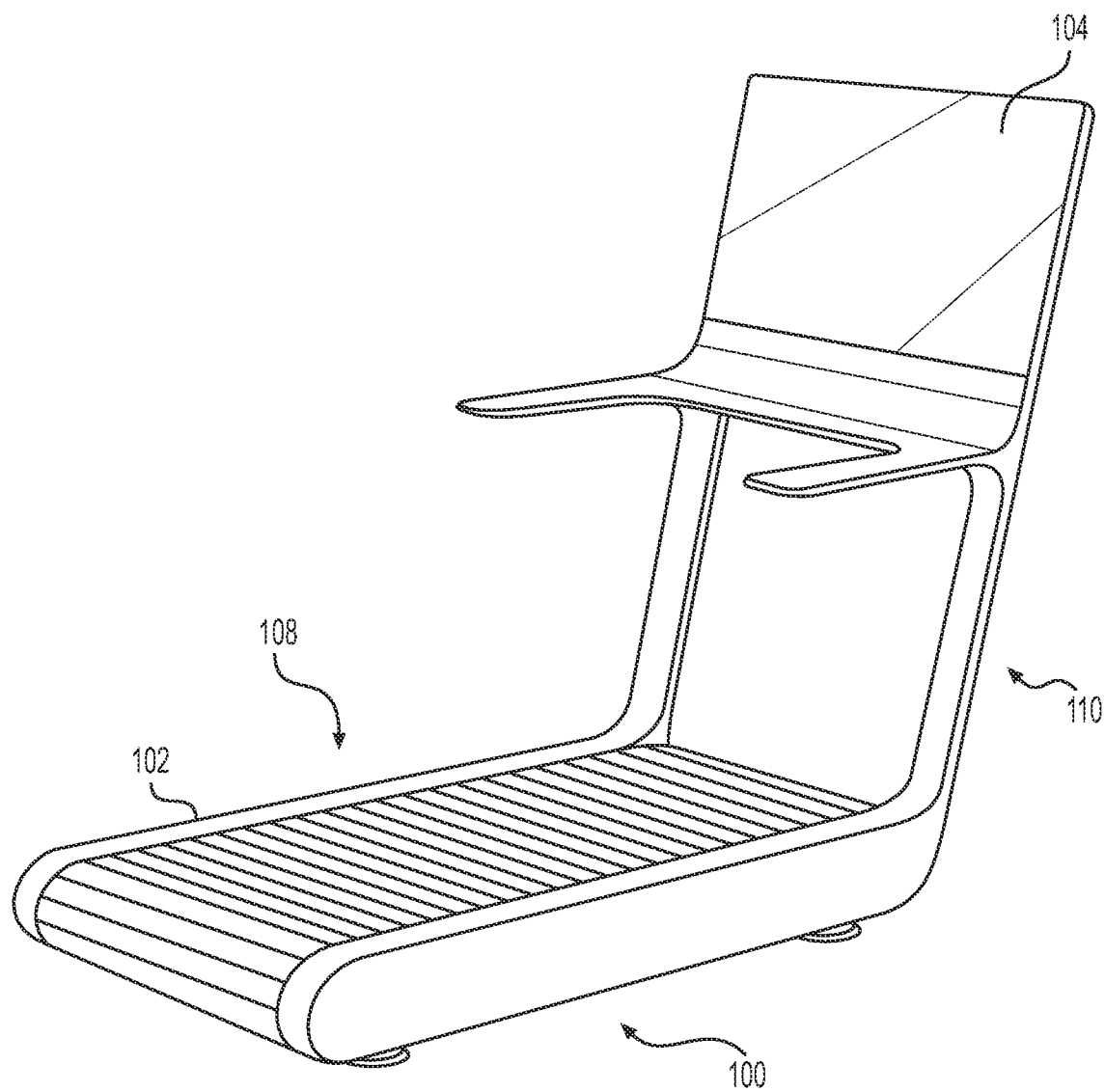
FIG. 2 is a rear perspective view of another exemplary exercise machine as disclosed herein.
Figure 3:
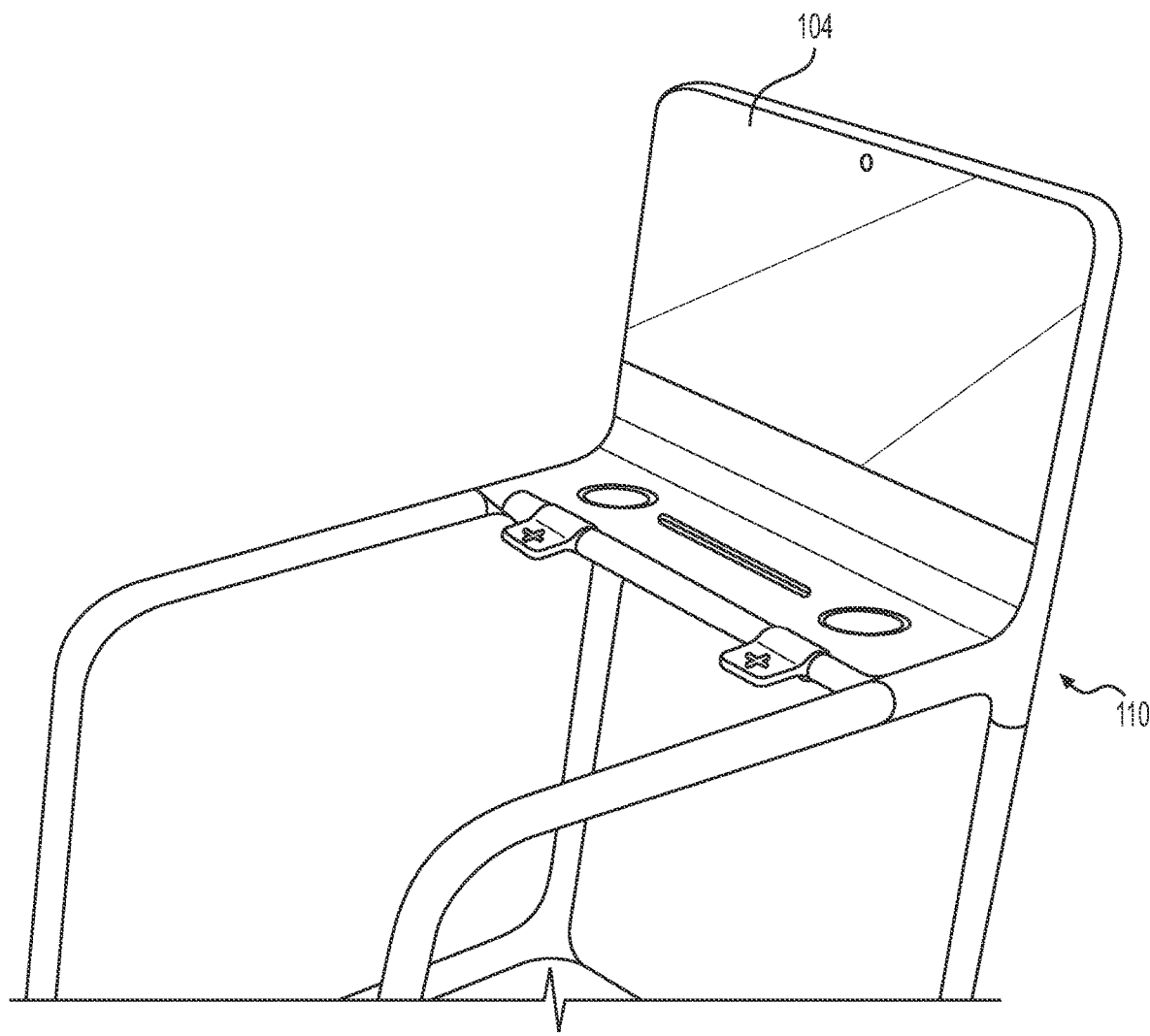
FIG. 3 is a rear perspective view of a portion of a further exemplary exercise machine as disclosed herein.
Figure 4:
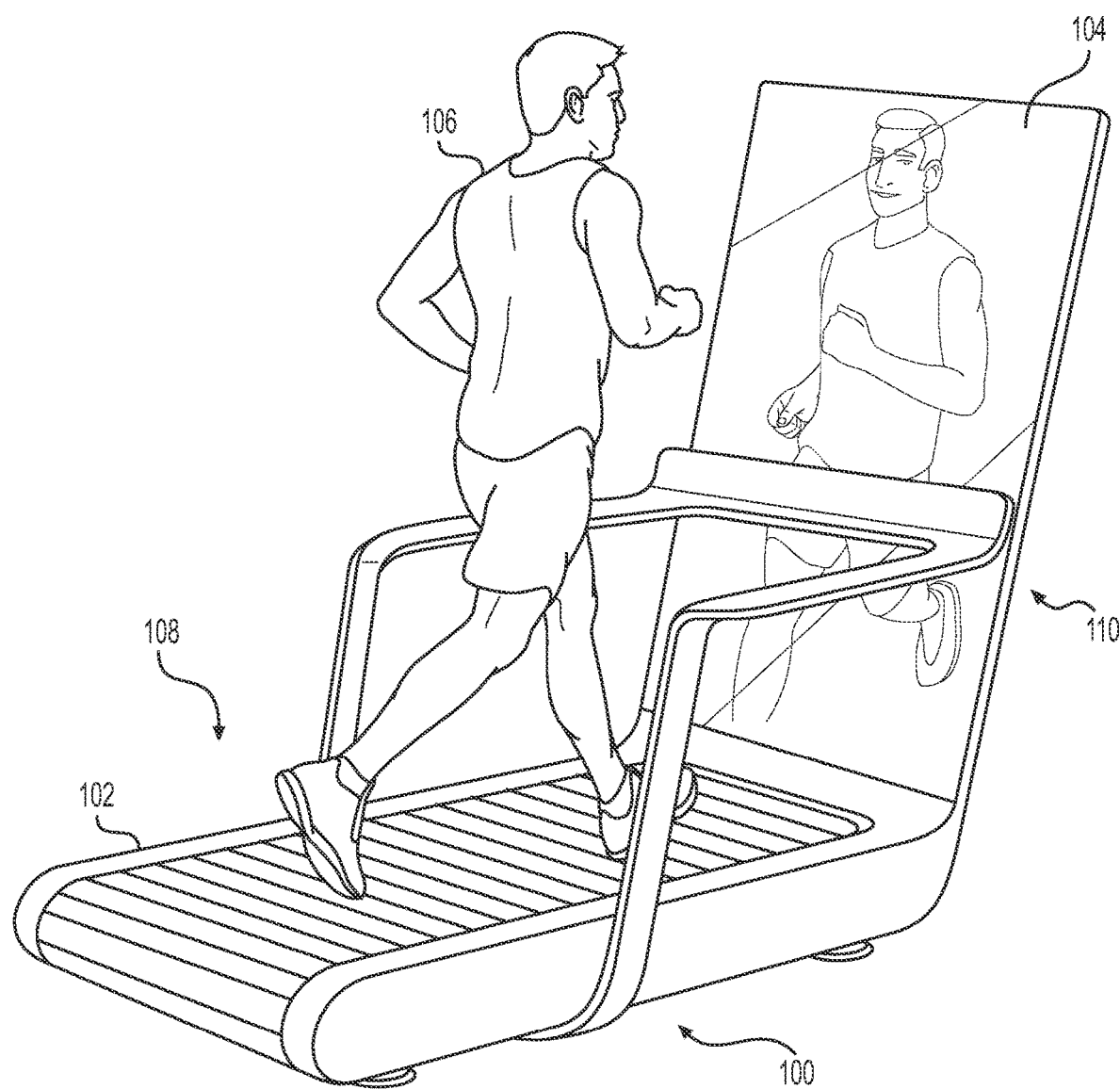
FIG. 4 is a rear perspective view of still another exemplary exercise machine as disclosed herein with a user shown.

The following description is presented to enable any person skilled in the art to make and use aspects of the example embodiments described herein. For purposes of explanation, specific nomenclature is set forth to provide a thorough understanding of the present invention. Descriptions of specific embodiments or applications are provided only as examples. Various modifications to the embodiments will be readily apparent to those skilled in the art, and general principles defined herein may be applied to other embodiments and applications without departing from the spirit and scope of the present disclosure. Thus, the present disclosure is not intended to be limited to the embodiments shown, but is to be accorded the widest possible scope consistent with the principles and features disclosed herein.

Example embodiments of the present disclosure include networked exercise systems and methods whereby one or more exercise devices, such as treadmills, rowing machines, stationary bicycles, elliptical trainers, or any other suitable equipment, may be equipped with an associated local system that allows a user to fully participate in live instructor-led or recorded exercise classes from any location that can access a suitable communications network. The networked exercise systems and methods may include backend systems with equipment including without limitation servers, digital storage systems, and other hardware as well as software to manage all processing, communications, database, and other functions. The networked exercise systems and methods may also include one or more studio or other recording locations with cameras, microphones, and audio and/or visual outputs where one or more instructors can lead exercise classes and in some embodiments where live exercise classes can be conducted, and where such live and previously recorded classes can be distributed via the communications network. In various embodiments there may be a plurality of recording locations that can interact with each other and/or with any number of individual users.

In various embodiments, the example exercise systems and machines describe herein provide for full interactivity in all directions. Whether remote or in the same location, instructors may be able to interact with users, users may be able to interact with instructors, and users may be able to interact with other users. Through the disclosed networked exercise systems and machines, instructors may be able to solicit feedback from users, and users may be able to provide feedback to the instructor, vote or express opinions on different choices or options, and communicate regarding their experience. Such example exercise systems and machines allow for interaction through all media, including one or more video channels, audio including voice and/or music, and data including a complete range of performance data, vital statistics, chat, voice, and text-based and other communications.

In various embodiments, the exercise systems and machines described herein also allow an unlimited number of remote users to view and participate in the same live or recorded content simultaneously, and in various embodiments they may be able to interact with some or all of the other users viewing same content. Remote users can participate in live exercise classes offered from any available remote recording location, or they can access previously recorded classes archived in the system database. In various embodiments, a plurality of remote users can simultaneously access the same recorded class and interact with each other in real time, or they can access the same recorded class at different times and share data and communications about their performance or other topics.

Thus, the networked exercise systems and machines, and the corresponding methods described herein, provide for content creation, content management and distribution, and content consumption. Various aspects of such exercise systems and machines, and the potential interactions between such machines, will now be described in more detail.

Exercise Machine

Referring generally to FIGS. 1 through 7 and FIGS. 25-35, in various example embodiments of the present disclosure, a local system 100 may include an exercise machine 102, such as a treadmill, with integrated or connected digital hardware including one or more displays 104 for use in connection with an instructor lead exercise class and/or for displaying other digital content. While the exercise machine 102 may be described and/or otherwise referred to herein as a "treadmill 102," as noted above, example exercise machines of the present disclosure may be any suitable type of exercise machine, including a rowing machine, stationary bicycle, elliptical trainer, stair climber, etc.

In various example embodiments, the one or more displays 104 may be mounted directly to the exercise machine 102 or otherwise placed within view of a user 106. In various exemplary embodiments, the one or more displays 104 allow the user 106 to view content relating to a selected exercise class both while working out on the exercise machine 102 and while working out in one or more locations near or adjacent to the exercise machine 102. As will be described in greater detail below, the exercise machine 102 may also include a hinge, joint, pivot, bracket or other suitable mechanism to allow for adjustment of the position or orientation of the display 104 relative to the user 106 whether they are using the exercise machine 102 or working out near or adjacent to the exercise machine 102.

In example embodiments, the exercise machine 102 may generally include a lower assembly 108 and an upper assembly 110. The lower assembly 108 may generally include a deck 112 of the exercise machine 102 that provides support for the user 106 while the use is working out on the exercise machine 102, as well as other components of bot the lower assembly 108 and the upper assembly 110. For example, as shown in at least the exploded view of FIG. 26, the deck 112 may support a first motor 114 of the exercise machine 102 configured to increase, decrease, and/or otherwise change an incline of the deck 112 relative to a support surface on which the exercise machine 102 is disposed. The deck 112 may also include one or more linkages 116 coupled to the motor 114 and configured to, for example, raise and lower the deck 112 by acting on the support surface when the motor 114 is activated. The deck 112 may also include a second motor 118 configured to increase, decrease, and/or otherwise change a rotational speed of a belt 120 connected to the deck 112. The belt 120 may be rotatable relative to the deck 112 and, in particular, may be configured to revolve or otherwise move completely around (i.e., encircle) the deck 112 during use of the exercise machine 120. For example, in embodiments in which the exercise machine 102 comprises a treadmill, the belt 120 may support the user 106 and may repeatedly encircle the deck 112 as the user 106 runs, walks, and/or otherwise works out on the treadmill. Such an example belt 120 may include one or more continuous tracks 122 movably coupled to a gear, flywheel, pulley, and/or other member 124 of the deck 112, and such a member 124 may be coupled to an output shaft or other component of the motor 118. In such examples, rotation of the output shaft or other component of the motor 118 may drive commensurate rotation of the member 124. Likewise, rotation of the member 124 may drive commensurate revolution of the one or more continuous tracks 122 and/or the belt 120 generally.

Figure 27:
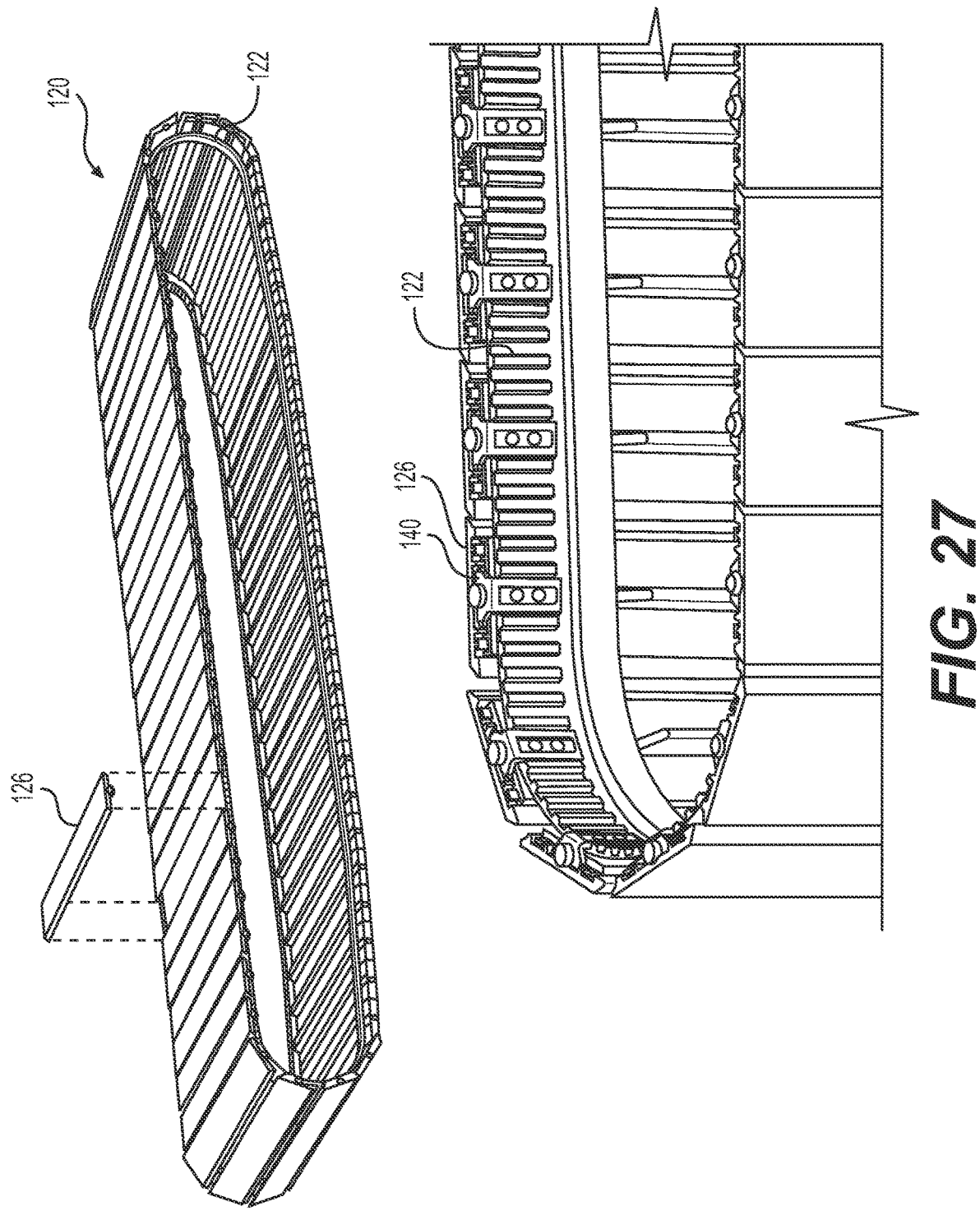
FIG. 27 illustrates a belt associated with the example exercise machine shown in FIG. 25.
Figure 28:
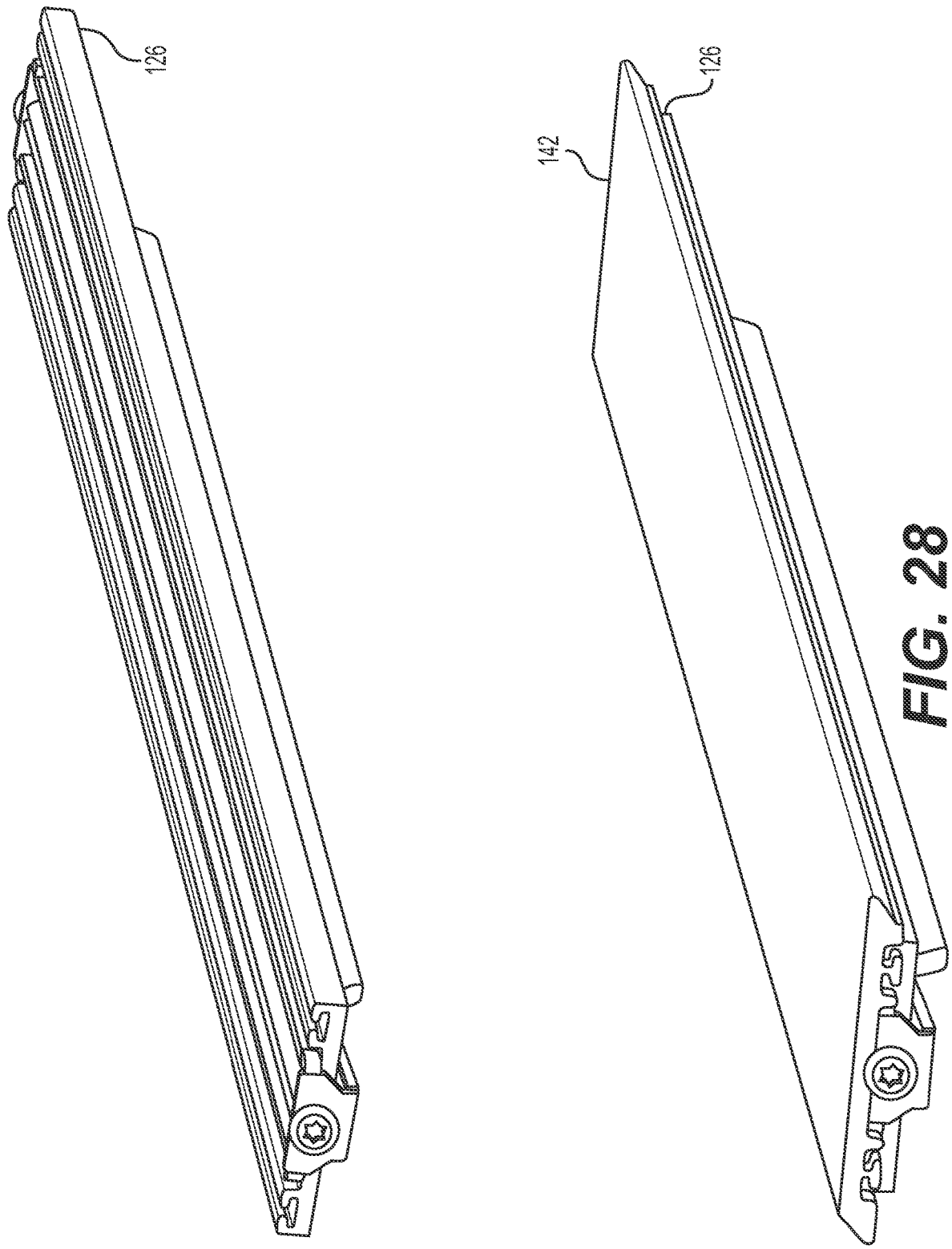
FIG. 28 illustrates a slat associated with the example exercise machine shown in FIG. 25.

The belt 120 may also include a plurality of laterally aligned slats 126 connected to the one or more continuous tracks 122. For example, as shown in FIGS. 27 and 28, each slat 126 may extend substantially parallel to at least one adjacent slat 126. Additionally, each slat 126 may be hingedly, pivotally, and/or otherwise movably coupled to the one or more continuous tracks 122 via one or more respective couplings 140. Such couplings 140 may comprise, for example, a bracket, pin, screw, clip, bolt, and/or one or more other fastening components configured to secure a respective slat 126 to the continuous track 122 while allowing the slat 126 to pivot, rotate, and/or otherwise move relative to the track 122 while the belt 120 revolves about the deck 112. As shown in at least FIG. 28, each slat 126 may also include a top pad 142 coupled thereto. The top pad 142 may comprise a plastic, rubber, polymeric, and/or other type of non-slip pad configured to reduce and/or substantially eliminate slipping of the user 106 when the user is running, walking, and/or otherwise exercising on the exercise machine 102. Such a top pad 142 may also reduce the impact associated with walking and/or running on the exercise machine 102, and may thus improve the comfort of the user 106 during various exercise classes associated with the exercise machine 102.

Figure 26:
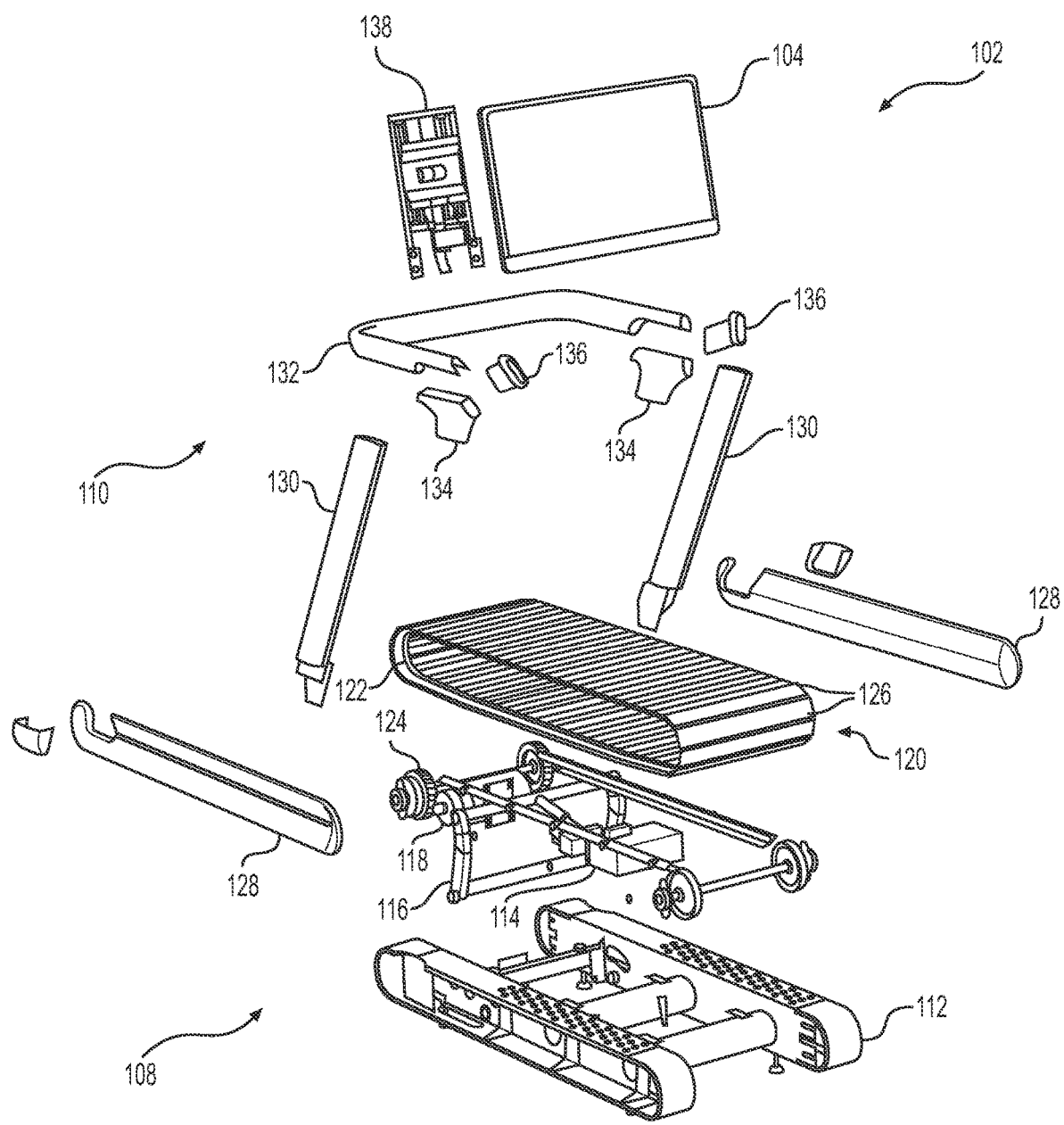
FIG. 26 illustrates an exploded view of the example exercise machine shown in FIG. 25.

With continued reference to FIG. 26, the exercise machine 102 may also include one or more sidewalls 128 connected to the deck 112. For example, the exercise machine 102 may include a first sidewall 128 on a left hand side of the deck 112, and a second sidewall 128 on the right hand side of the deck 112. Such sidewalls 128 may be made from cloth, foam, plastic, rubber, polymers, and/or other like material, and in some examples, the sidewalls 128 may assist in damping and/or otherwise reducing noise generated by one or more of the motors 114, 118 and/or other components of the deck 112.

The exercise machine 102 may also include one or more posts 130 extending upwardly from the deck 112. For example, the exercise machine 102 may include a first post 130 on the left hand side of the deck 112, and a second post 130 on the right hand side of the deck 112. Such posts 130 may be made from a metal, alloy, plastic, polymer, and/or other like material, and similar such materials may be used to manufacture the deck 112, the slats 126, and/or other components of the exercise machine 102. In such examples, the posts 130 may be configured to support the display 104, and in some examples, the display 104 may be directly coupled to a crossbar 132 of the exercise machine 102, and the crossbar 132 may be connected to and/or otherwise supported by the posts 130. For example, the crossbar 132 may comprise one or more hand rests or handles useful in supporting the user 106 during exercise. In some examples, the crossbar 132 may be substantially C-shaped, substantially U-shaped, and/or any other configuration. In any of the examples described herein, the crossbar 132 may extend from a first one of the posts 130 to a second one of the posts 130. Further, in some examples, the posts 130 and the crossbar 132 may comprise a single integral component of the upper assembly 110. Alternatively, in other examples, the posts 130 and the crossbar 132 may comprise separate components of the upper assembly 110. In such examples, the upper assembly 110 may include one or more brackets 134, endcaps 136, and/or additional components configured to assist in coupling the one or more posts 130 to the crossbar 132.

As noted above, the exercise machine 102 may also include a hinge, joint, pivot, bracket 138 and/or other suitable mechanism to allow for adjustment of the position or orientation of the display 104 relative to the user 106 whether they are using the exercise machine 102 or working out near or adjacent to the exercise machine 102. For example, such brackets 138 may include at least one component rigidly connected to the crossbar 132. Such brackets 138 may also include one or more additional components rigidly coupled to the display 104. In such examples, the components of the bracket 138 connected to the display 104 may be moveable, with the display 104 relative to the components of the bracket 138 connected to the crossbar 132. Such components may include one or more dove-tail slider mechanism, channels, and/or other components enabling the display 104 to controllably slide and/or otherwise move relative to the crossbar 132. Such components may also enable to the user 106 to fix the position of the display 104 relative to the crossbar 132 once the user 106 has positioned the display 104 as desired.

Figure 29:
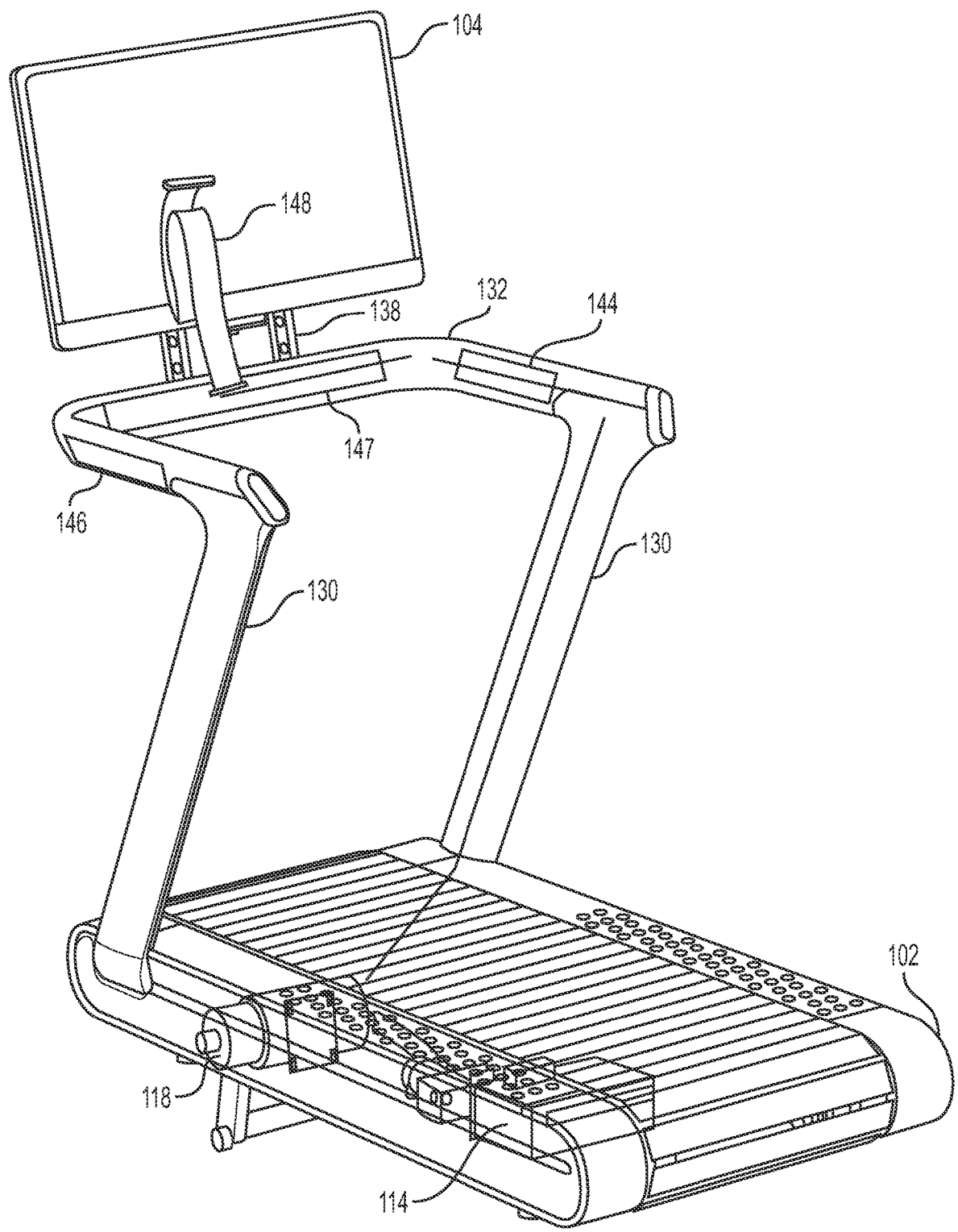
FIG. 29 illustrates another view of the example exercise machine shown in FIG. 25 including one or more sensors and one or more controls.
Figure 30:
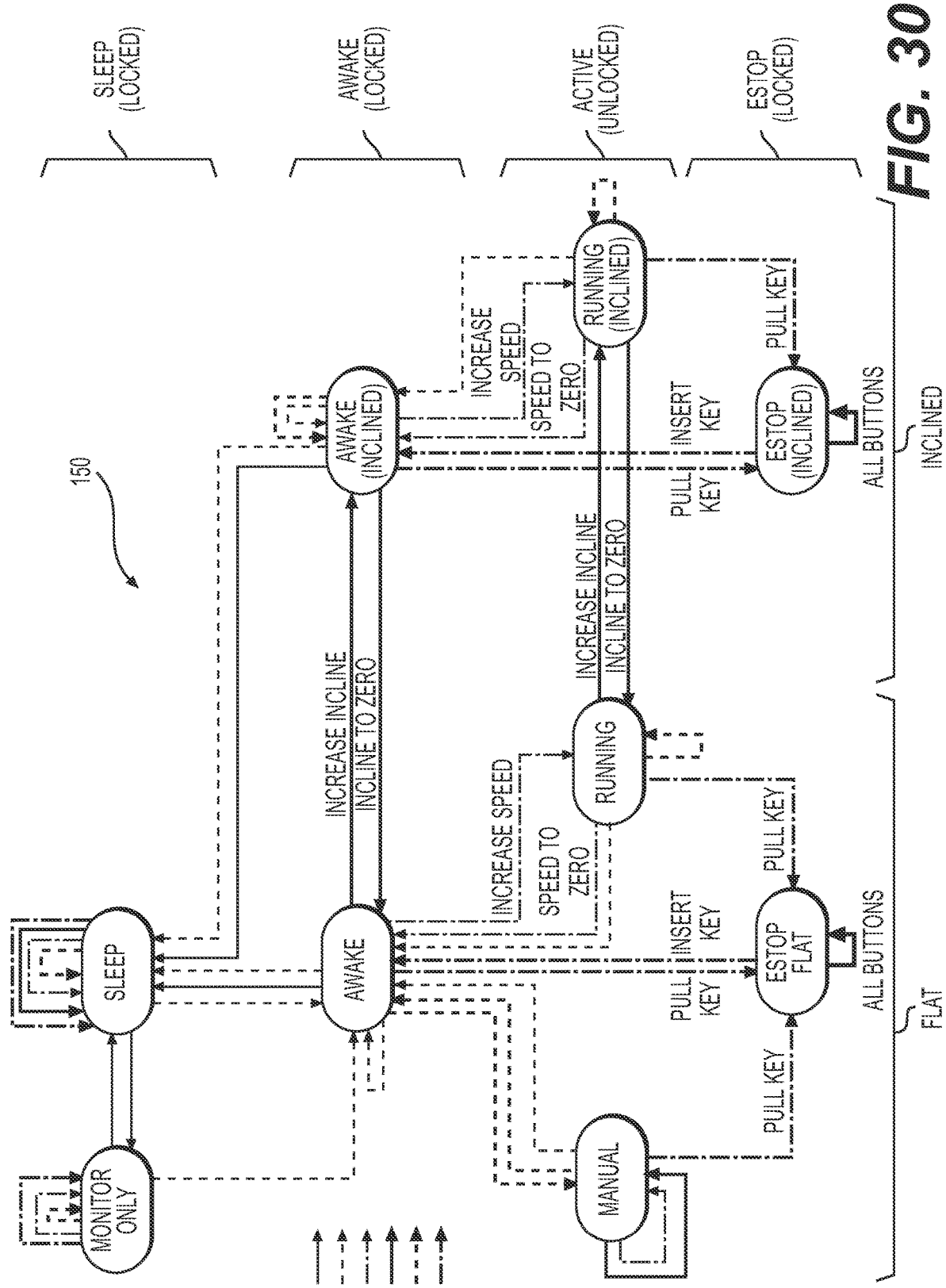
FIG. 30 illustrates a control architecture associated with the example exercise machine shown in FIG. 25.

As shown in at least FIG. 29, the exercise machine 102 may also include one or more controls 144, 146 configured to receive input from the user 106. The exercise machine 102 may further include one or more sensors 147 configured to sense, detect, and/or otherwise determine one or more performance parameters of the user 106 before, during, and/or after the user 106 participates in an exercise class using the exercise machine 102. In any of the examples described herein, the controls 144, 146 and the one or more sensors 147 may be operably and/or otherwise connected to one or more controllers, processors, and/or other digital hardware 148 of the exercise machine 102.

The digital hardware 148 associated with the exercise machine 102 may be connected to or integrated with the exercise machine 102, or it may be located remotely and wired or wirelessly connected to the exercise machine 102. The digital hardware 148 may include digital storage, one or more processors or other like computers or controllers, communications hardware, software, and/or one or more media input/output devices such as displays, cameras, microphones, keyboards, touchscreens, headsets, and/or audio speakers. In various exemplary embodiments these components may be connected to and/or otherwise integrated with the exercise machine 102. All communications between and among such components of the digital hardware 148 may be multichannel, multi-directional, and wireless or wired, using any appropriate protocol or technology. In various exemplary embodiments, the digital hardware 148 of the exercise machine 102 may include associated mobile and web-based application programs that provide access to account, performance, and other relevant information to users from local or remote exercise machines, processors, controllers, personal computers, laptops, mobile devices, or any other digital device or digital hardware. In any of the examples described herein, the one or more controllers, processors, and/or other digital hardware 148 associated with the exercise machine 102 may be operable to perform one or more functions associated with control logic 150 of the exercise machine 102. Such control logic 150 is illustrated schematically in at least FIG. 30, and such control logic 150 may comprise one or more rules, programs, or other instructions stored in a memory of the digital hardware 148. For example, one or more processors included in the digital hardware 148 may be programmed to perform operations in accordance with rules, programs, or other instructions of the control logic 150, and such processors may also be programmed to perform one or more additional operations in accordance with and/or at least partly in response to input received via one or more of the controls 144, 146 and/or via one or more of the sensors 147.

Figure 31:
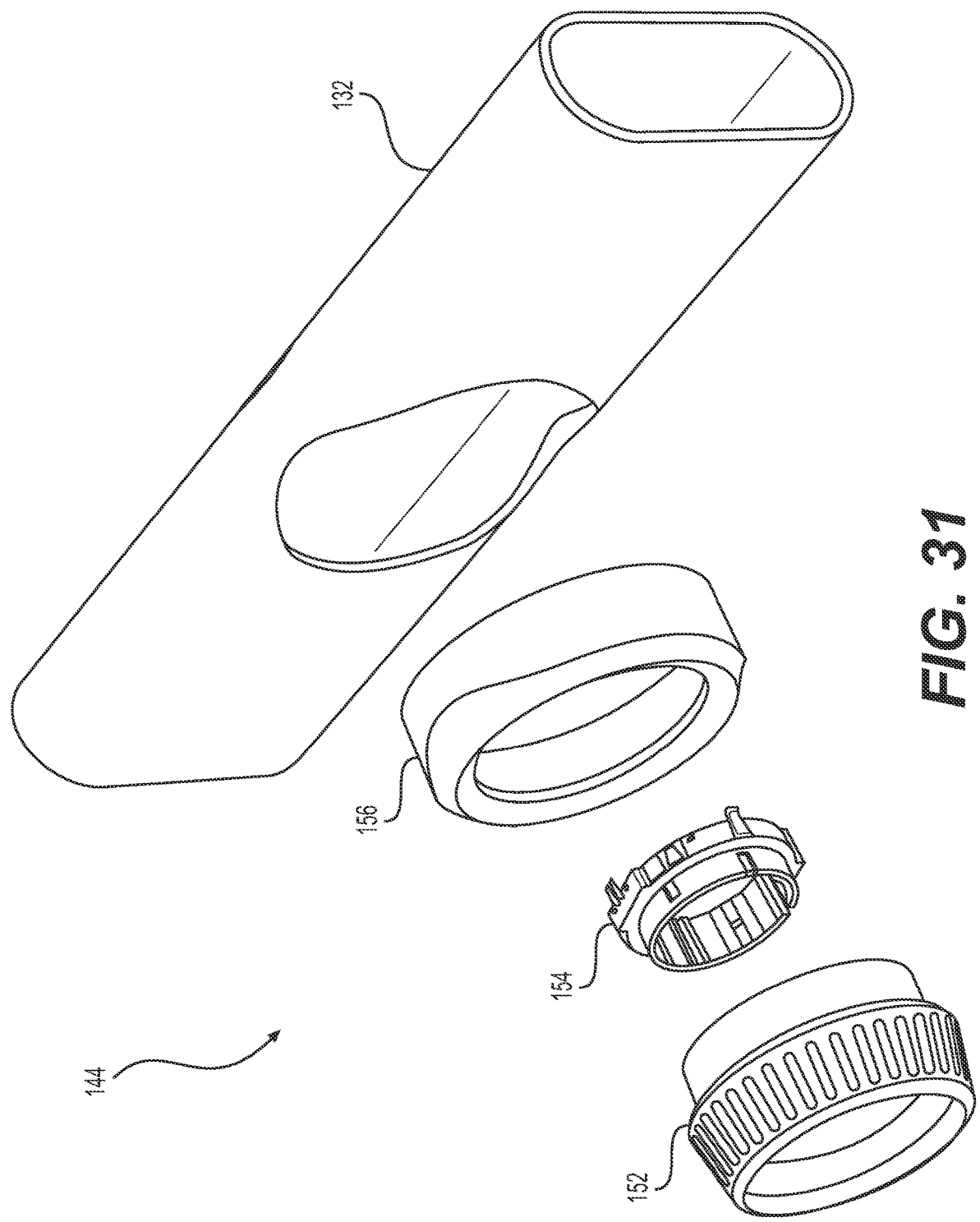
FIG. 31 illustrates an exploded view of a rotary control associated with the example exercise machine shown in FIG. 25.
Figure 32:
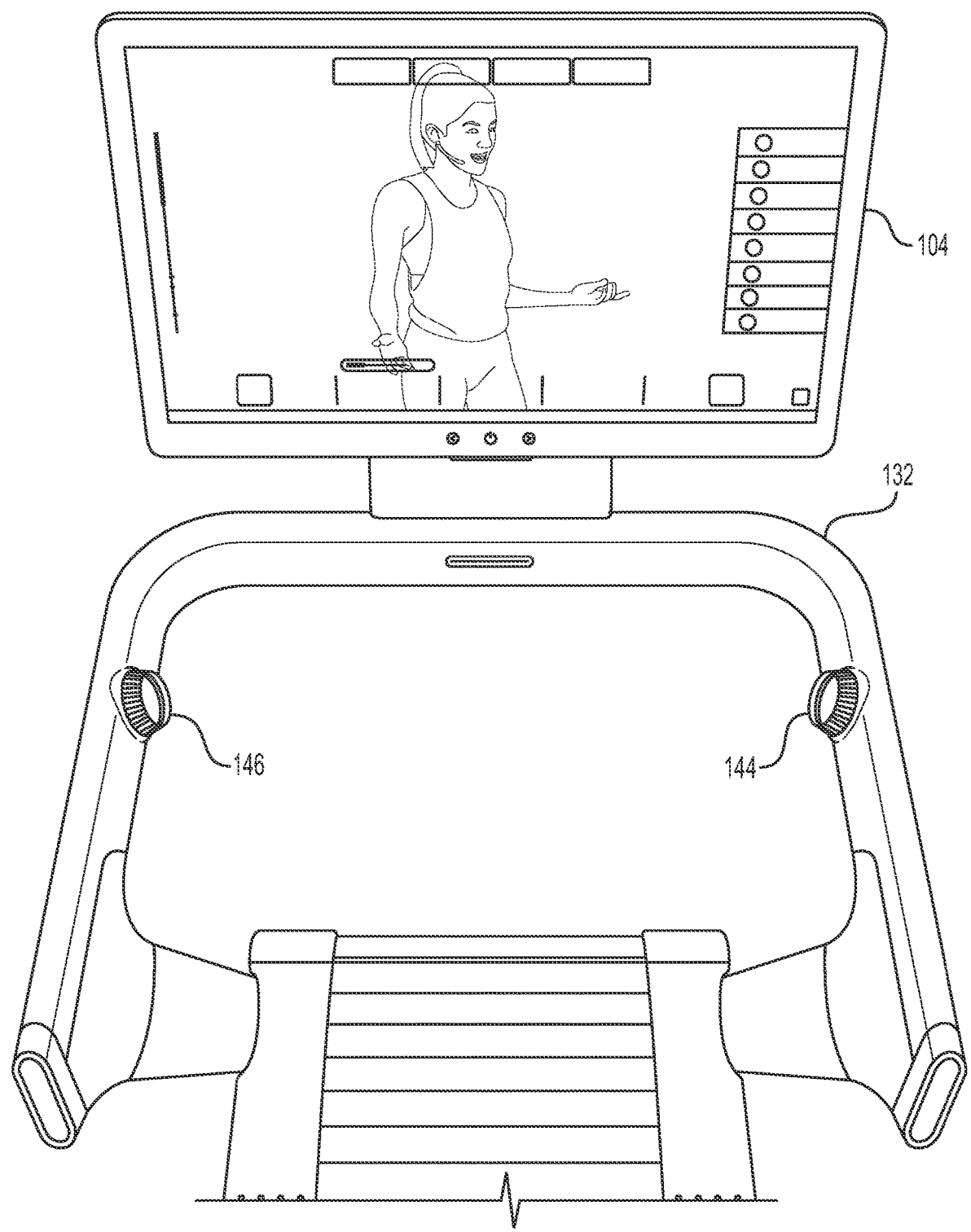
FIG. 32 illustrates another view of the example exercise machine shown in FIG. 25 including first and second rotary controls.

As shown in FIGS. 31 and 32, one or more such controls 144, 146 may comprise an infinity wheel-type control 144. Such a control may be useful in changing and/or otherwise controlling, for example, the incline of the deck 112, the speed of the belt 120, and/or other operations of the exercise machine 102 associated with incremental increases or decreases. In an example embodiment, such a control 144 may include a rotary dial 152 connected to a corresponding rotary encode 154. In such examples, the rotary encoder 154 may include one or more detents or other components/structures that may be tuned for a desired incremental change in a corresponding functionality of the exercise machine 102. For example, the rotary encoder 154 may be tuned such that each detent thereof may correlate to a 0.5% increase or decrease in an incline angle of the deck 112. Alternatively, the rotary encoder 154 may be tuned such that each detent thereof may correlate to a 0.1 mph increase or decrease in a speed of the belt 120. IN still further examples, percentages, speeds, and/or other increments greater than or less than those noted above may be chosen. Additionally, one or more such controls 144, 146 may include one or more additional buttons, wheels, touch pads, levers, knobs, or other components configured to receive additional inputs from the user 106, and such additional components may provide the user 106 with finer control over the corresponding functionality of the exercise machine 102. One or more such controls 144, 146 may also include a respective control housing 156 configured to assist in mounting the control 144, 146 to the crossbar 132 or other components of the exercise machine 102.

Figure 33:
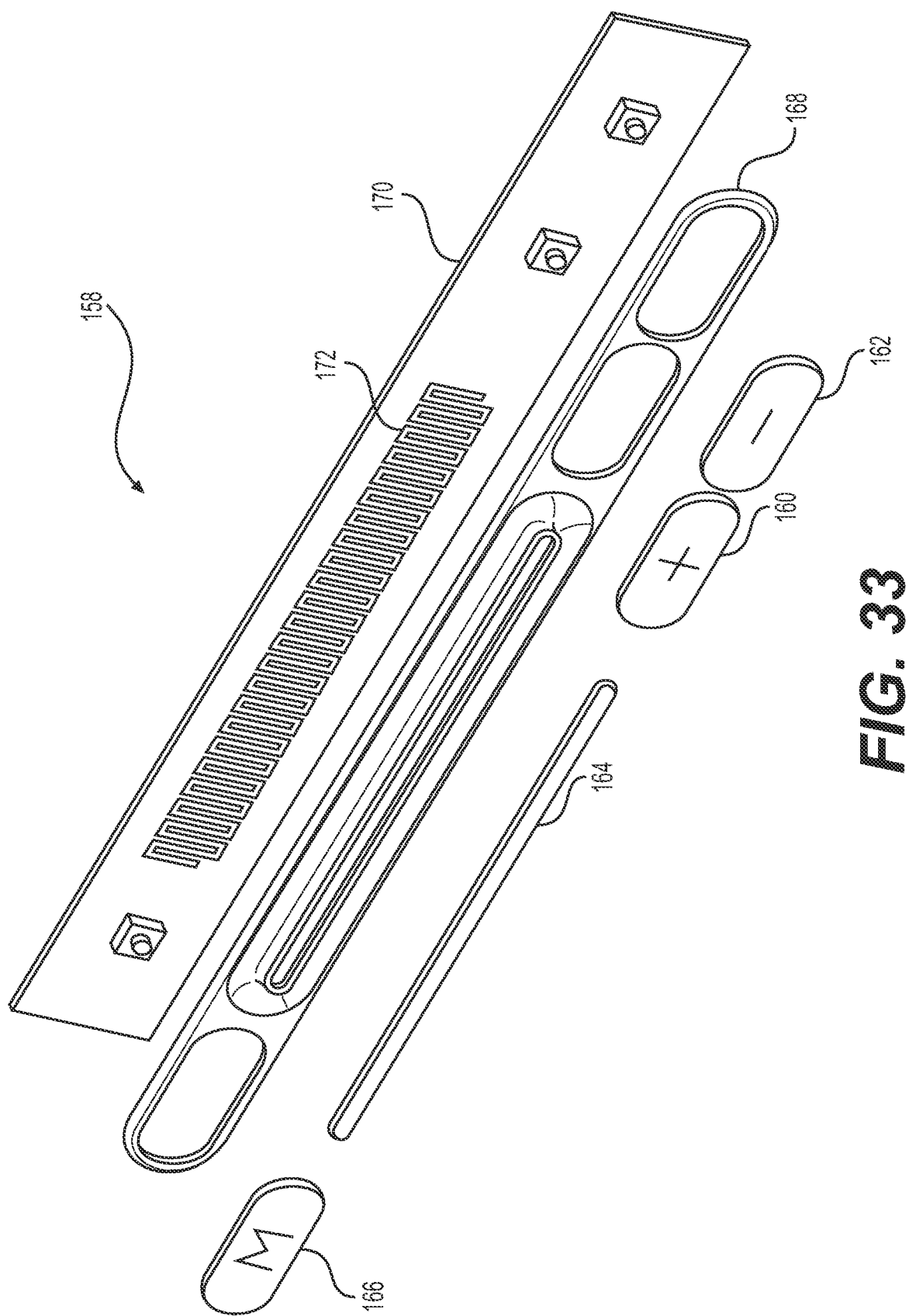
FIG. 33 illustrates an exploded view of a substantially linear control associated with the example exercise machine shown in FIG. 25.
Figure 34:
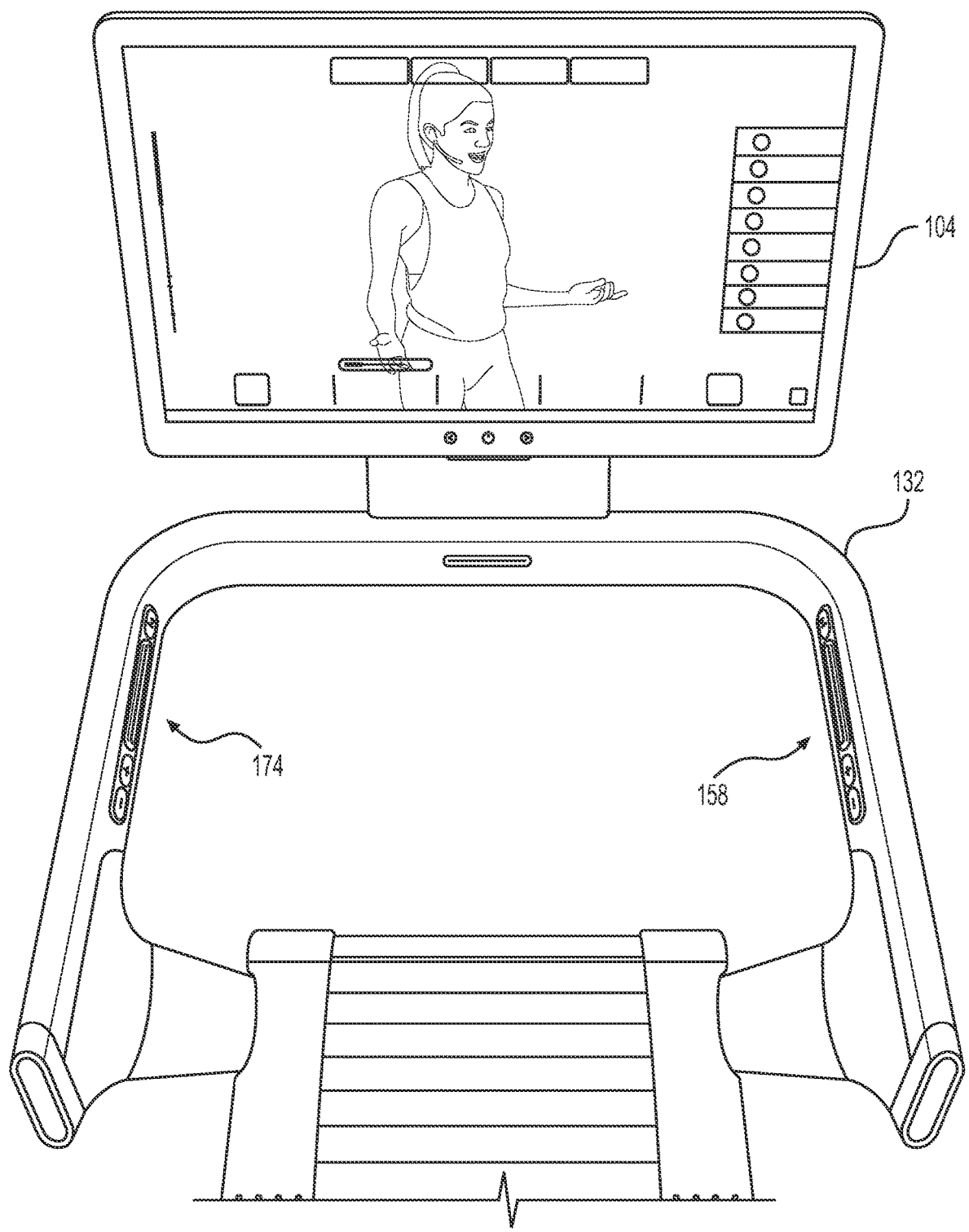
FIG. 34 illustrates another view of the example exercise machine shown in FIG. 25 including first and second substantially linear controls.
Figure 35:
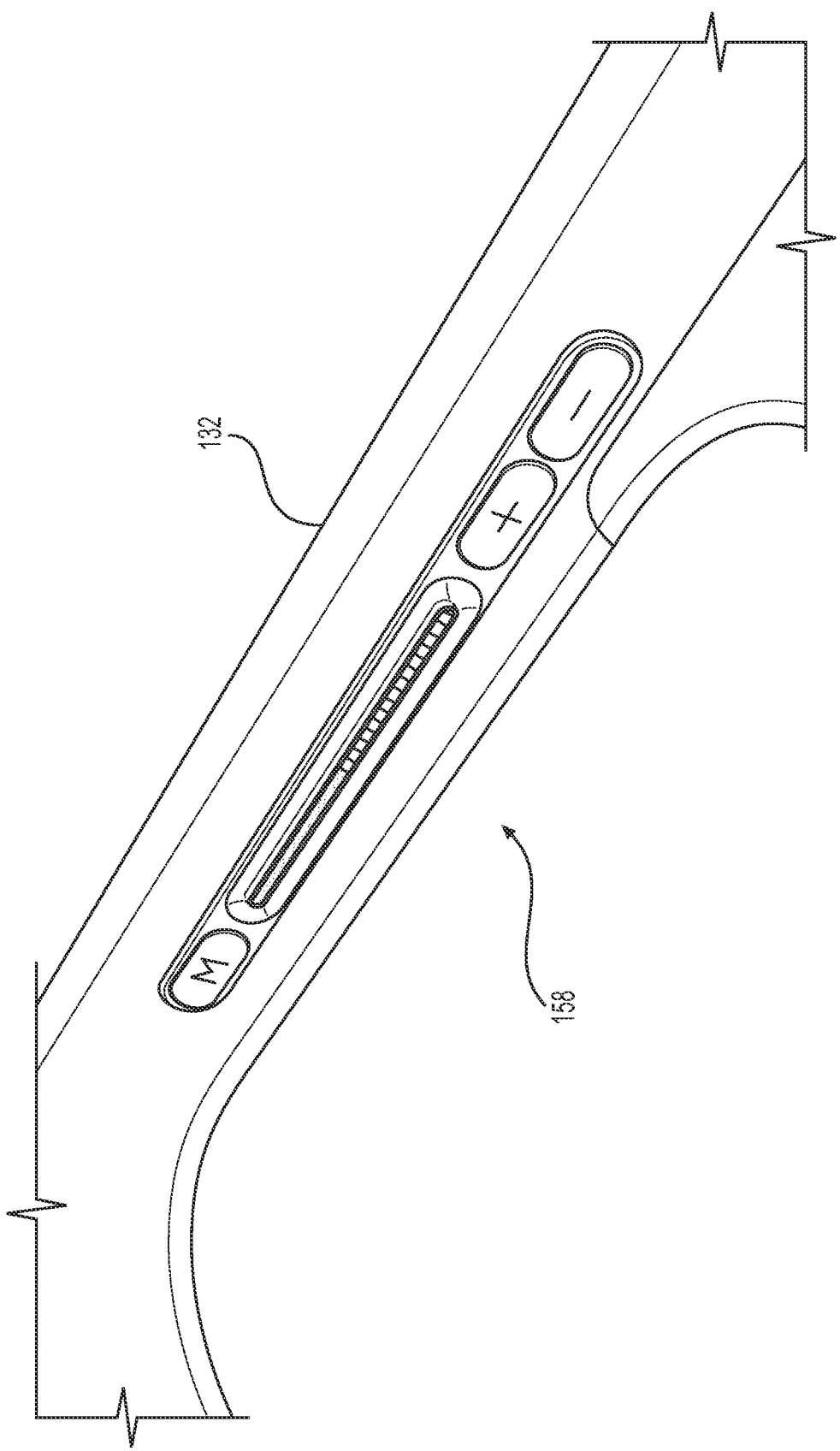
FIG. 35 illustrates a portion of the example exercise machine shown in FIG. 25 including a substantially linear control.

As shown in FIGS. 33-35, in still further embodiments one or more of the infinity wheel-type controls 144, 146 described herein may be replaced with a capacitive slider-type control and/or other substantially linear control 158. Such controls 158 may include one or more touch pads, buttons, levers, and/or other components 160, 162, 166 configured to receive a touch, tap, push, and/or other input from the user 106. Such components 160, 162, 166 may be operably connected to respective touch and/or tactile switches of the control 158 mounted to a printed circuit board 170 thereof. Such tactile switches may be configured to generate signals indicative of the input received via such components 160, 162, 166, and to direct such signals to the processor and/or other digital hardware 148 associated with the exercise machine 102. The controls 158 may also include one or more additional touch pads 164 having a substantially linear configuration. Such touch pads 164 may also be configured to receive a touch, tap, push, and/or other input from the user 106. Additionally, the touch pads 164 may be operably connected to a respective capacitive trace 172 of the control 158 mounted to the printed circuit board 170. In such examples, the capacitive trace 172 may be configured to generate signals indicative of the input received via the touch pad 164 and to direct such signals to the processor and/or other digital hardware 148 associated with the exercise machine 102. FIG. 34 illustrates a first substantially linear control 158 disposed on the right hand side of the crossbar 132, and a second substantially linear control 174 disposed on the left hand side of the crossbar 132 opposite the control 158. In any of the examples described herein, one or more of the components 160, 162, 166 may be operable to control and/or change operating modes of the exercise machine 102. Additionally, in any of the examples described herein, one or more of the infinity wheel-type controls 144, 146 and/or one or more of the substantially linear controls 158, 174 may include light emitting diodes and/or other lighting indicating a change in operation that is affected by the respective control.

With continued reference to at least FIG. 29, in various exemplary embodiments, the sensors 147 of the exercise machine 102 may be configured to sense, detect, measure, and/or otherwise determine a range of performance metrics from both the exercise machine 102 and the user 106, instantaneously and/or over time. For example, the exercise machine 102 may include one or more sensors 147 that measure the incline of the deck 112, the speed of the belt 120, a load applied to the deck 112, the belt 120, one or more of the motors 114, 118, and/or other components of the exercise machine 102, an amount of energy expended by the user 106, a power output of the exercise machine 102, user weight, steps, distance, total work, repetitions, an amount of resistance applied to the belt 120 by one or more of the motors 114, 118 and/or other components of the exercise machine 102, as well as any other suitable performance metric associated with, for example, a treadmill. The exercise machine 102 may also include sensors 147 to measure user heart-rate, respiration, hydration, calorie burn, or any other physical performance metrics, or to receive such data from sensors provided by the user 106. Where appropriate, such performance metrics can be calculated as current/ instantaneous values, maximum, minimum, average, or total over time, or using any other statistical analysis. Trends can also be determined, stored, and displayed to the user, the instructor, and/or other users. Such sensors 147 may communicate with memory and/or processors of the digital hardware 148 associated with the exercise machine 102, nearby, or at a remote location, using wired or wireless connections.

Figure 6:
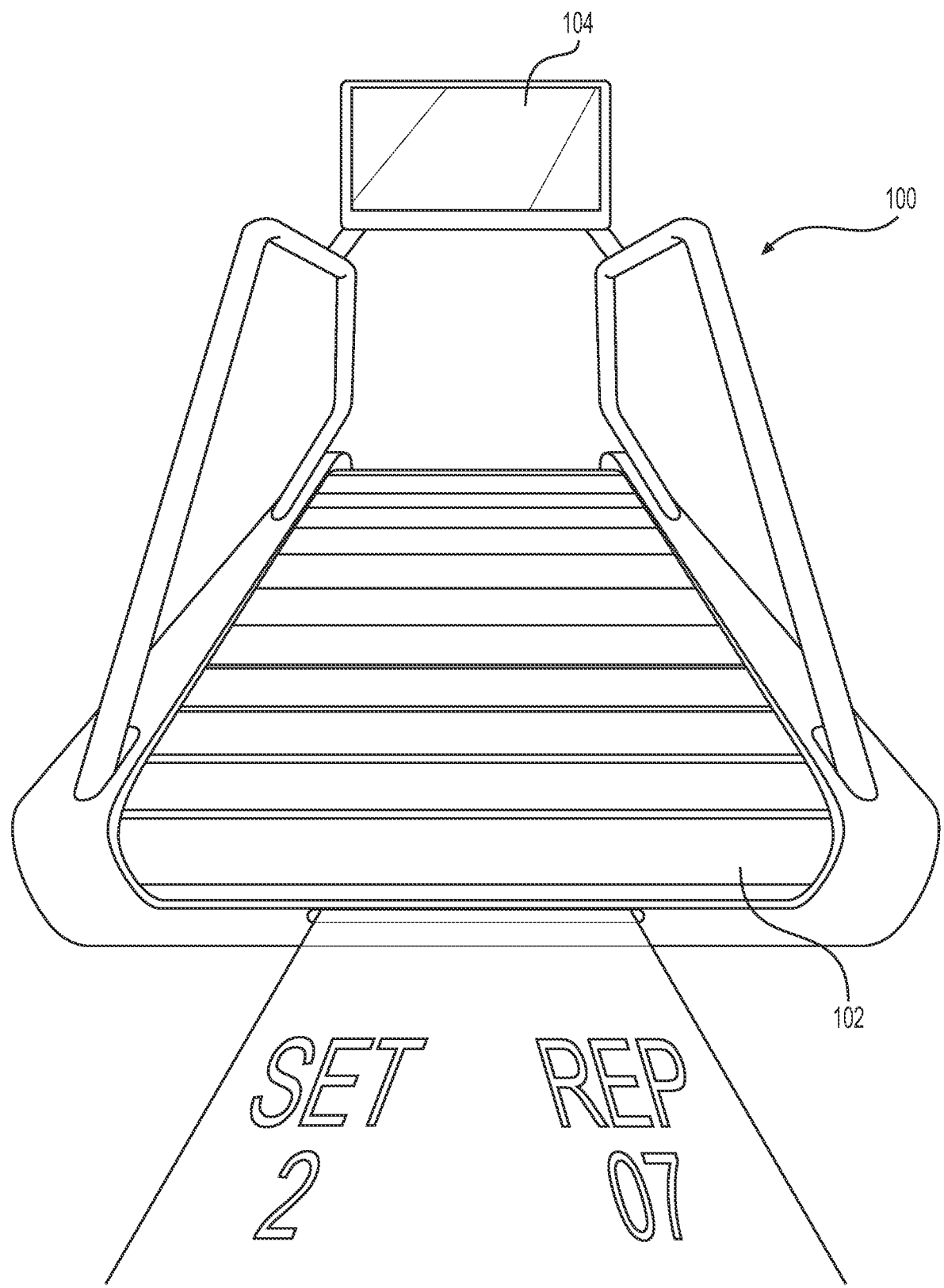
FIG. 6 is a rear view of yet another exemplary exercise machine as disclosed herein.
Figure 7:
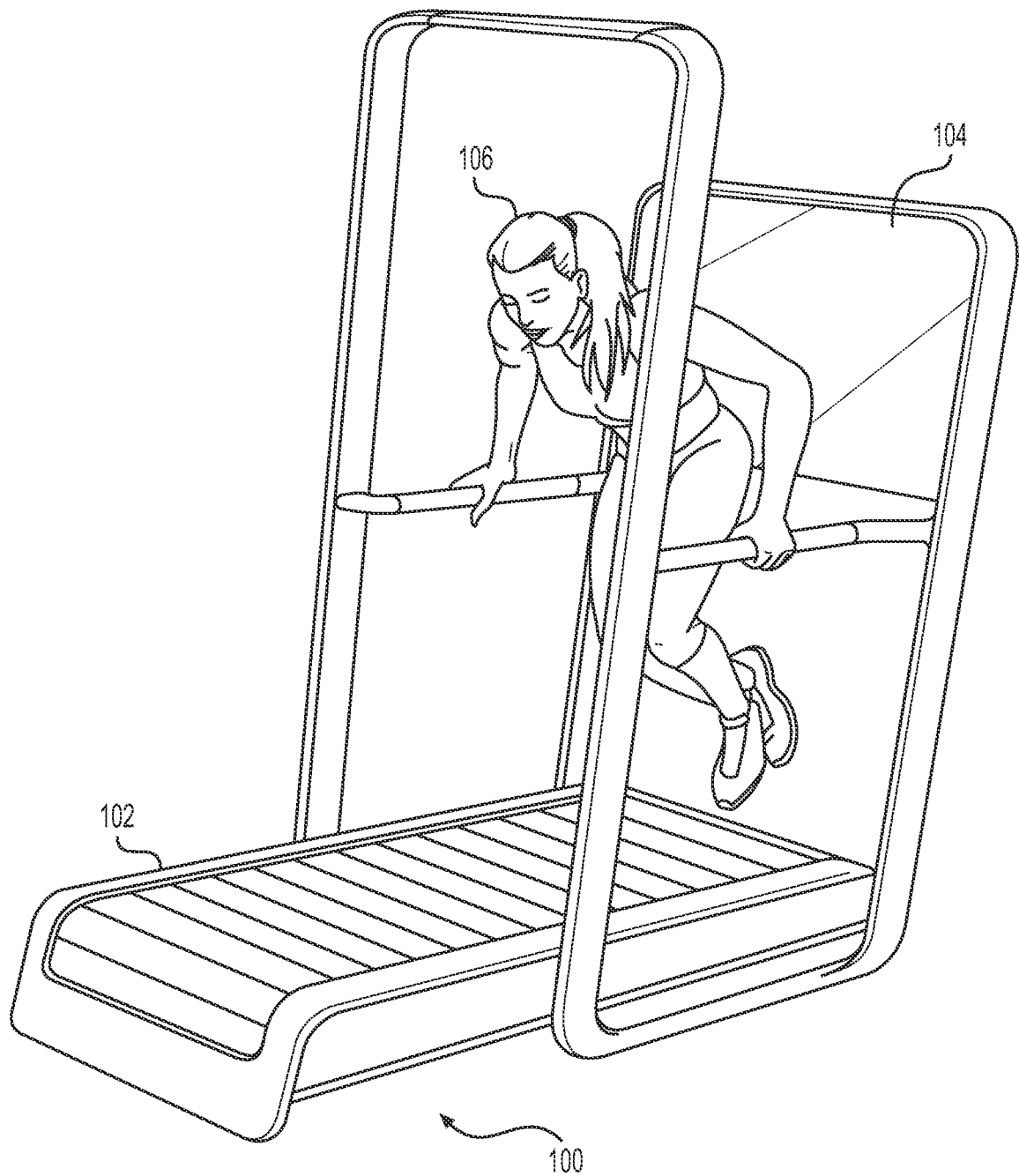
FIG. 7 is a rear perspective view of still another exemplary exercise machine as disclosed herein with a user shown.

In various exemplary embodiments, the exercise machine 102 may also be provided with one or more indicators to provide information to the user 106. Such indicators may include lights, projected displays, speakers for audio outputs, or other output devices capable of providing a signal to a user 106 to provide the user 106 with information such as timing for performing an exercise, time to start or stop exercise, or other informational indicators. For example, as illustrated in FIG. 6, such indicators (e.g., lights or projected displays) could display information regarding the number of sets and repetitions performed by the user 106 at a location where it can be seen by the user 106 during the performance of the relevant exercise.

Display and User Interface

The one or more displays 104 may be driven by a user input device such as a touchscreen, mouse, voice control, or other suitable input device. In some examples, the display 104 or at least a portion thereof, may comprise a touchscreen configured to receive touch input from the user 104. The one or more displays 104 may be any size, but optimally are large enough and oriented to allow the display of a range of information including one or more video streams, a range of performance metrics corresponding to the user 106, a range of additional performance metrics associated with one or more additional users exercising on exercise machines remote from the exercise machine 102, and a range of different controls. In various exemplary embodiments, such as the embodiment illustrated in FIG. 4, the display 104 may include some or all of its area that can reflect the image of the user 106 to provide user feedback regarding their form and performance of various activities.

In various exemplary embodiments the user can use the display 104 or one or more user interfaces 200 displayed on the display 104 to selectively present a range of different information including live and/or archived video, performance data, and other user and system information. As will be described below with respect to at least FIGS. 12-24, such user interfaces 200 can provide a wide range of control and informational windows that can be accessed and removed individually and/or as a group by a click, touch, voice command, or gesture. In various exemplary embodiments, such windows may provide information about the user's own performance and/or the performance of other participants in the same class both past and present.

Example user interfaces 200 presented via the display 104 may be used to access member information, login and logout of the system 100, access live content such as live exercise classes and archived classes or other content. User information may be displayed in a variety of formats and may include historical and current performance and account information, social networking links and information, achievements, etc. The user interfaces described herein 200 can also be used to access the system 100 to update profile or member information, manage account settings such as information sharing, and control device settings.

An example user interface 200 may also be presented on the one or more displays 104 to allow users to manage their experience, including selecting information to be displayed and arranging how such information is displayed on the display 104. Such a user interface 200 may present multiple types of information overlaid such that different types of information can be selected or deselected easily by the user 106. For example, performance metrics and/or other information may be displayed over video content using translucent or partially transparent elements so the video behind the information elements can be seen together with (i.e., simultaneously with) the performance metrics and/or other information itself. Further, example user interfaces 200 may present a variety of screens to the user 106 which the user 106 can move among quickly using the provided user input device, including by touching if a touchscreen is used.

In any of the examples described herein, the processor and/or other components of the digital hardware 148 may control the display 104 and/or otherwise cause the display 104 to display the various user interfaces 200 of the present disclosure. For example, the processor or other components of the digital hardware 148 may cause the display 104 to display a user interface 200 comprising a home screen that provides basic information about the system 100 and/or the exercise machine 102, as well as available options. Such a home screen may provide direct links to information such as scheduled classes, archived classes, a leaderboard, instructors, and/or profile and account information. The home screen may also provide direct links to content such as a link to join a particular class. The user can navigate among the different portions of the home screen by selecting such links using the applicable input device such as by touching the touchscreen at the indicated location, or by swiping to bring on a new screen. An example user interface 200 providing such a home screen may also provide other information relevant to the user such as social network information, and navigation buttons that allow the user to move quickly among the different screens in the user interface.

Figure 12:
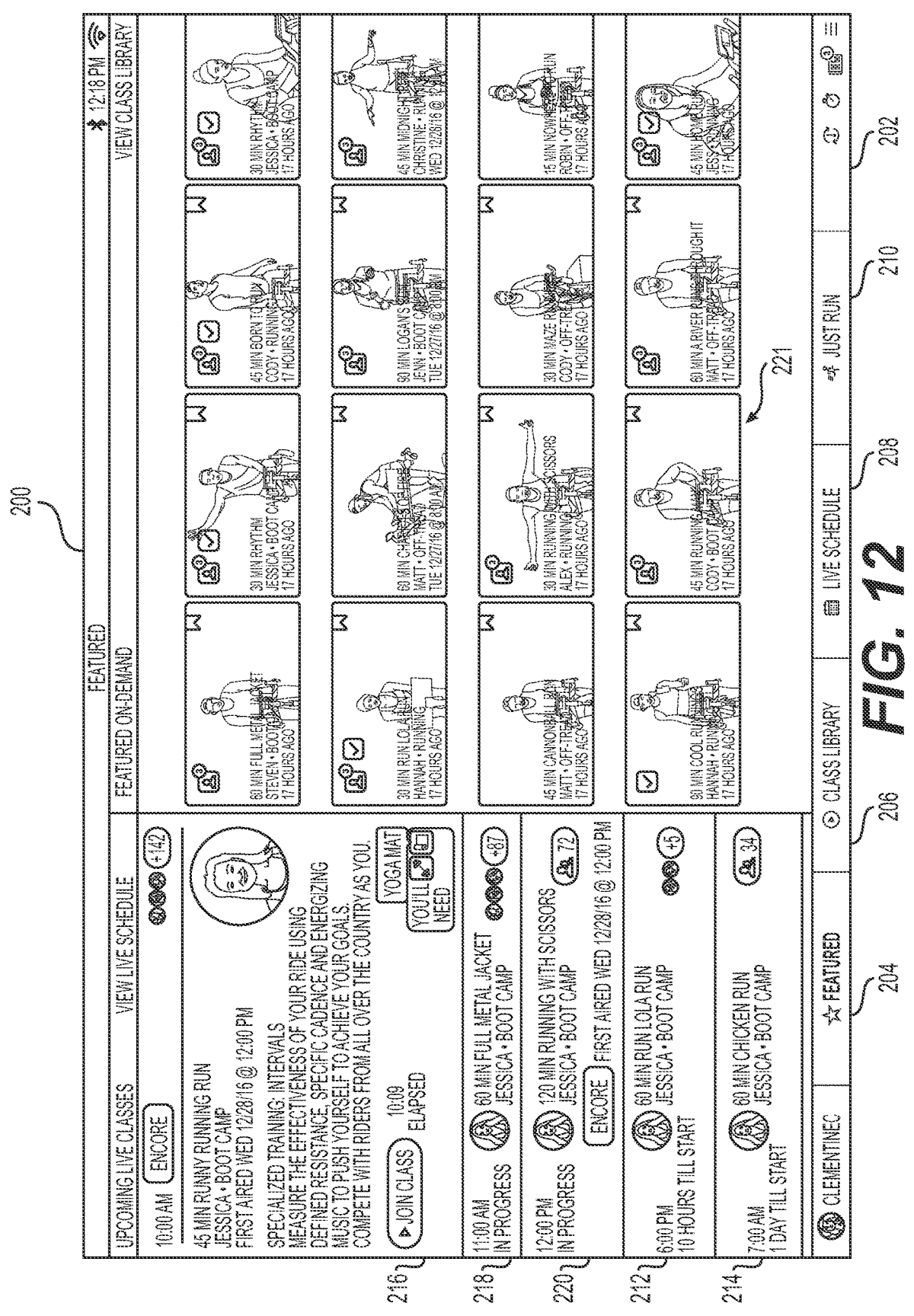
Figure 13:
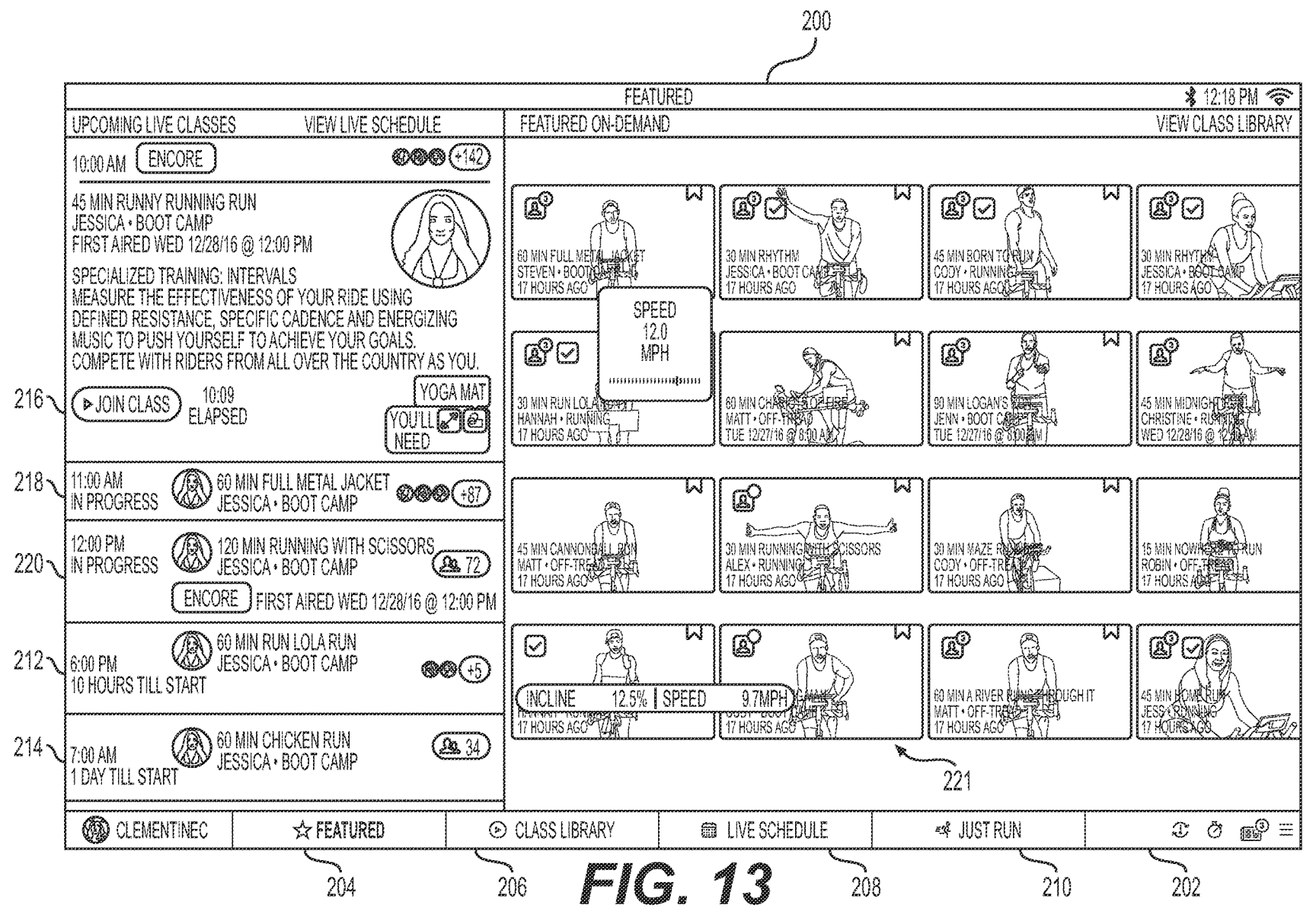
Figure 14:
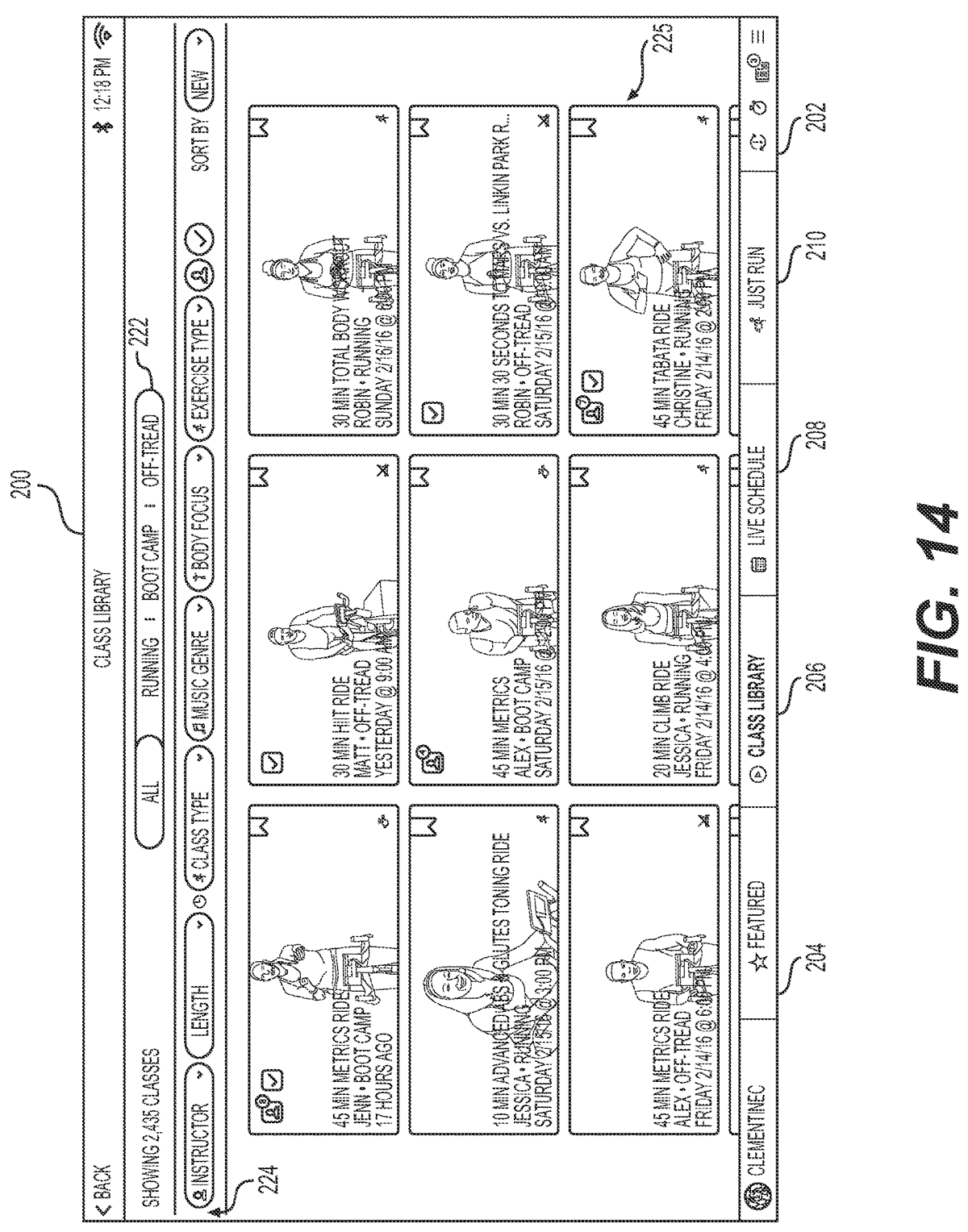

In various exemplary embodiments, the user 106 can use one or more of the user interfaces 200 to browse and select among both live and archived content. For example, as shown in FIGS. 12-14, example user interfaces 200 may include one or more toolbars 202 enabling the user 106 to access listings and/or other information regarding available exercise classes. Such example toolbars 200 may include respective tabs or other controls enabling the user 106 to browse such content. For example, the toolbar 200 may include a first tab 204 enabling the user to access featured live and archived exercise classes, a second tab 206 enabling the user to access a library of archived exercise classes, a third tab 208 enabling the user to access a schedule of live classes, a fourth tab 210 enabling the user to access a variety of quick start or "just run" content, and/or other additional or different tabs.

As shown in FIGS. 12 and 13, if the user 106 selects the first tab 204 associated with featured classes, the user interface 200 may present a schedule of upcoming live or archived classes that have achieved a high ranking or other preferential (e.g., "featured") status. The user interface 200 may include one or more drop-down menus or other display features, and such features may also allow users to find such featured classes by type, instructor, or by any other appropriate category. The user interfaces 200 associated with the featured classes tab 204 may allow the user 106 to select future classes (as illustrated by thumbnails or icons 212, 214) or to start a class that is underway or about to begin (as illustrated by thumbnails or icons 216, 218, 220). Further, the user interfaces 200 associated with the featured classes tab 204 may allow the user 106 to select an archived or on-demand class that has already taken place (as illustrated by thumbnails or icons 221). The class schedule and information regarding "featured" content or any other content may be presented via such user interfaces 200 in any suitable format, including a calendar, list, or any other appropriate layout. For example, selecting the third tab 208 associated with the live schedule of exercise classes may yield a user interface 200 presenting an upcoming schedule of live classes set forth on a calendar.

Figure 15:
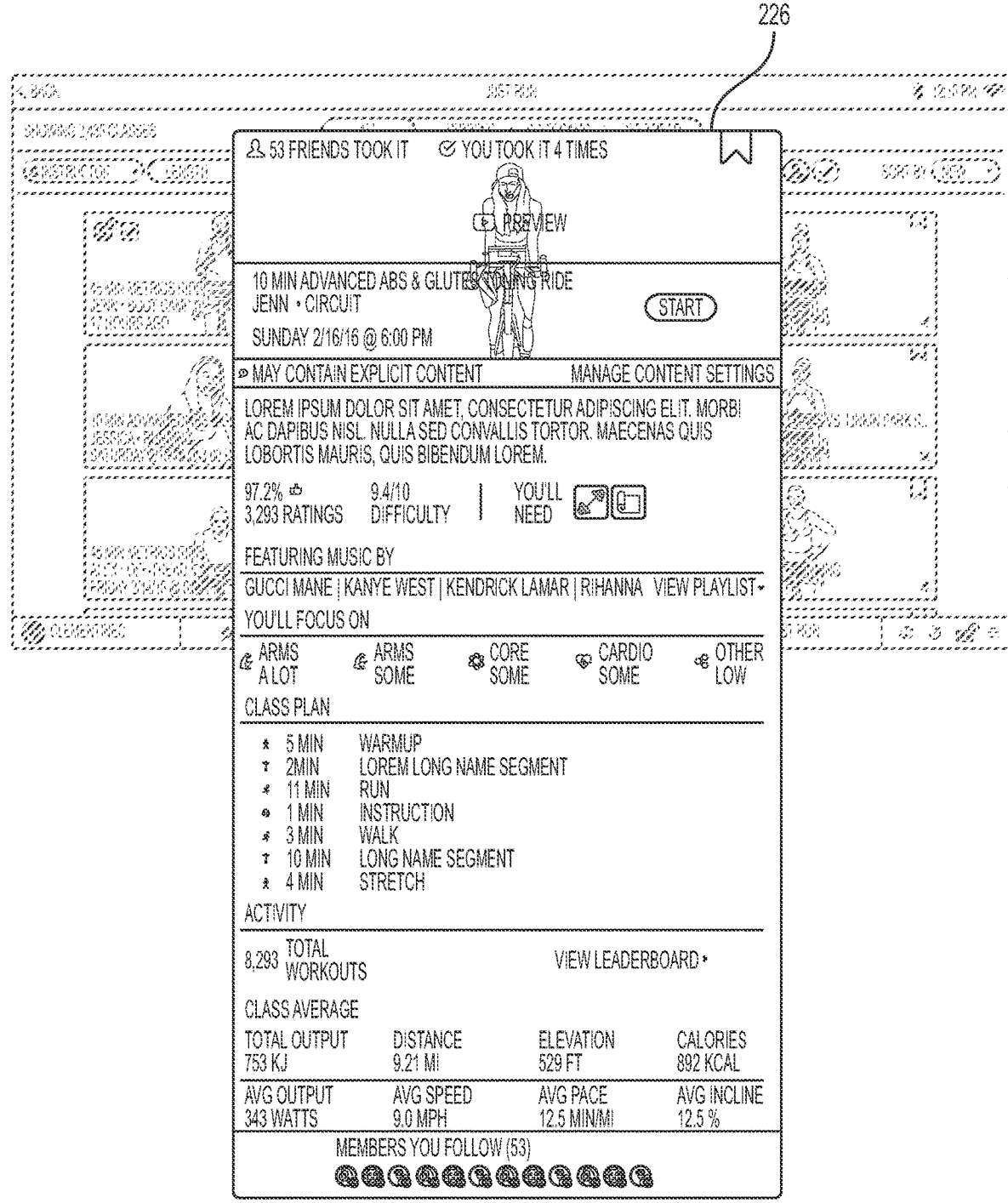
FIG. 15 illustrates another example user interface of the present disclosure including information related to a selected exercise class.

As illustrated by the example user interface 200 shown in FIG. 14, if the user 106 selects the second tab 206 associated with the class library, the system 100 may provide a user interface 200 showing information related to available archived classes, and such information may be sorted in a number of different ways. As illustrated by the menu icon 222, the user interface 200 may filter the classes included in the class library such that only icons or thumbnails 225 corresponding to classes associated with running, boot camp, and off-tread are provided to the user 106. Additionally, such user interfaces 200 may include one or more drop down menus 224 enabling the user 106 to further filter the classes included in the class library. For example, such drop down menus 224 may enable the user 106 to select classes based on instructor, length, class type, music genre, body focus, exercise type, etc. Additionally, as shown in FIG. 14, the icons or thumbnails 225 may be displayed in any suitable format, and may include information including the instructor of the class, the class length, the date on which the class was originally held, the type of class, and/or other related information. Further, as shown in FIG. 15, selecting one of the thumbnails 225 may surface additional information to the user 106 via an additional window 226 of the user interface 200. Such additional information may include, for example, a rating of the class, how many times the user has taken that class in the past, the portions of the body that are focused on during the class, additional equipment (e.g., weights) that may be needed during the class, as well as other performance or class-related information.

Figure 16:
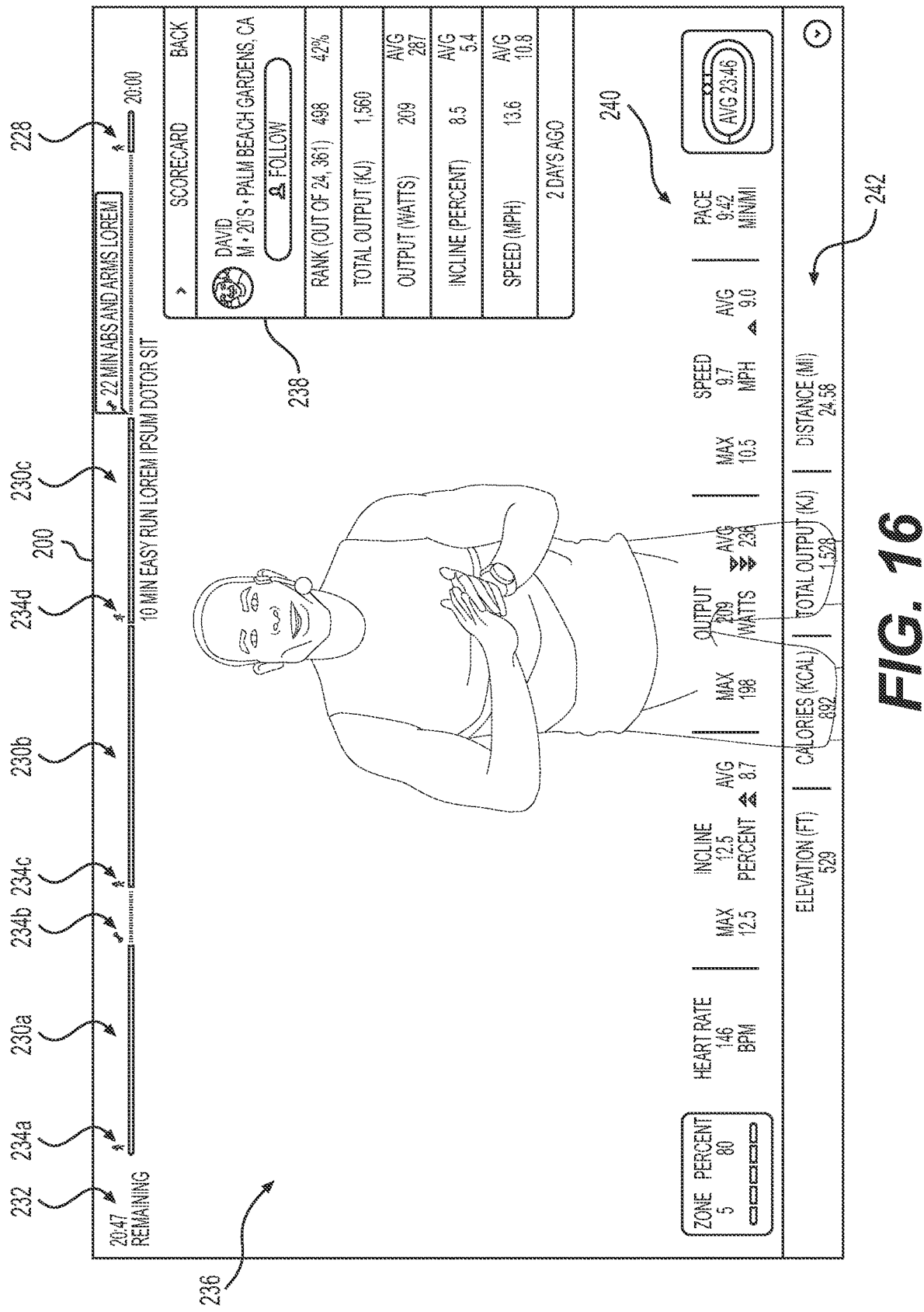
FIG. 16 illustrates still another example user interface of the present disclosure showing an exercise class and a scorecard.
Figure 17:
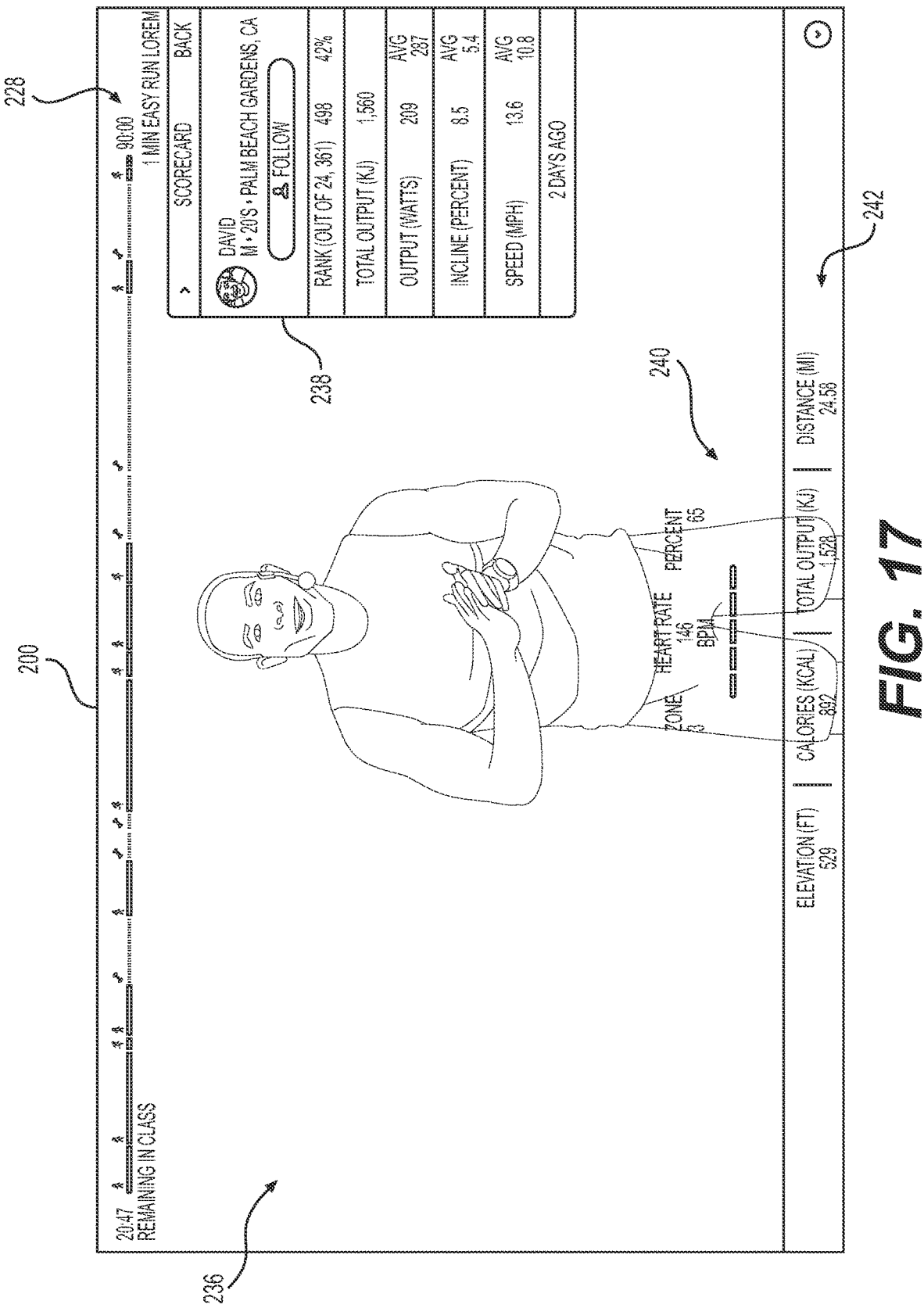
FIG. 17 illustrates yet another example user interface of the present disclosure showing an exercise class and a scorecard.
Figure 18:
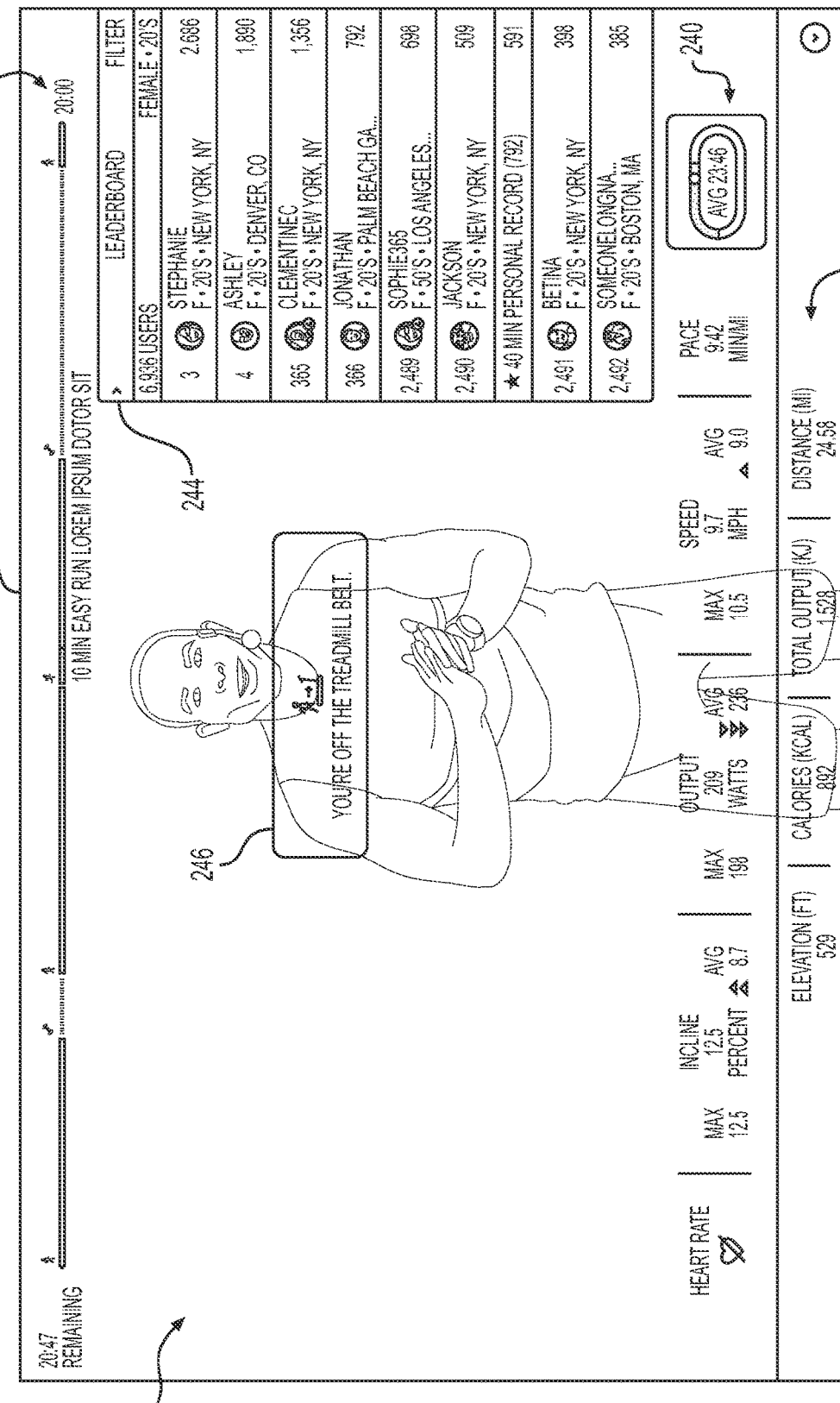
FIG. 18 illustrates a further example user interface of the present disclosure showing an exercise class and a leaderboard.

FIGS. 16-18 illustrate example user interfaces 200 that may be provided to the user 106 during a selected exercise class. When an exercise class is being played on the one or more displays 104 through the user interface 200, in various exemplary embodiments the primary video feed may be shown as the background video full-screen or in a sub-window on the display 104. Information elements may be provided on different parts of the display screen to indicate any performance metrics, including total time, elapsed time, time left, distance, speed, mile pace of the user 106, incline, elevation, resistance, power, total work, energy expended (e.g., output), cadence, heart rate, respiration, hydration, calorie burn, and/or any custom performance scores that may be developed. The displayed information may also include the trend or relationship between different performance metrics. For example, the display can indicate a particular metric in a color that indicates current performance compared to average performance for a class or over time, such as red to indicate that current performance is below average or green to indicate above average performance. Trends or relative performance can also be shown using color and graphics, such as a red down arrow to show that current performance is below average.

In various exemplary embodiments, the display 104 may also display information that supports or supplements the information provided by the instructor. Examples include one or more segmented timelines 228 that are illustrated together with at least part of the selected exercise class in the user interface 200. As shown in FIGS. 16-18, an example segmented timeline 228 may include one or more segments 230a, 230b, 230c . . . 230n (collectively, "segments 230") corresponding to respective portions or parts of the selected exercise class. The size, length, width, height, relative position, color, opacity, and/or other configurations of such segments 230 may be representative of, for example, the length of the corresponding portions or parts of the selected exercise class. The segmented timeline 228 may also provide an indication 232 of elapsed time and/or remaining time for the present workout segment and/or for the exercise class generally. The segmented timeline 228 may also include one or more visual indica 234a, 234b, 234c . . . 234n (collectively, "indicia 234") indicating an activity and/or equipment required during a respective portion or part of the selected exercise class. For example, the indicia 234a may indicate that the segment 230a comprises a walking segment, indicia 234d may indicate that the segment 230c comprises a running segment, and the indicia 234b may indicate that weights are required for at least part of the segment 230a. In any of the examples described herein, such timelines 228 may also include one or more lists or windows identifying and/or describing upcoming workout segments or features, instructional information such as graphics or videos demonstrating how to properly perform exercises, or other information relevant to the exercise class in progress.

As shown in FIGS. 16-18, the user interface 200 may include a primary window 236 configured to show the live or archived exercise class or other content that the user 106 selected. In various exemplary embodiments, the user interface 200 may further include one or more performance metric windows 238 (e.g., the "scorecard" illustrated in FIGS. 16 and 17) overlaid on and/or otherwise displayed together with the primary window 236. Such performance metric windows 238 may show a ranking, total output, current output, incline, belt speed, mile pace, and/or other specific performance metrics for the user's current class, past classes, or other performance information. Such performance metric windows 238 may be presented anywhere on the display 104, and may be user selectable such that they can be displayed or removed by a screen touch or gesture.

The user interface 200 may also allow the user 106 to toggle between display of maximum, average, and total results for different performance metrics. Additionally, the user interface 200 may allow the user 106 to hide or display information elements, including performance metrics, video streams, user information, etc. all at once or individually. Performance metrics and/or other performance information can also be displayed in various display bars 240, 242 that can be hidden or displayed as a group or individually. The user interface 200 may provide for complete controls for audio volume, inputs, and outputs as well as display output characteristics.

As shown in FIG. 18, a leaderboard 244 may also be displayed to allow the user 106 to see their performance in comparison to others taking the same exercise class. In various exemplary embodiments, a leaderboard 244 may comprise a separate window overlaid on and/or otherwise displayed together with the primary window 236. An example leaderboard 244 may be configured to display the relative performance of all participants, and/or of one or more subgroups of participants. For example, the user 106 may be able to select a leaderboard 244 that shows the performance of participants in a particular age group, male participants, female participants, male participants in a particular age group, participants in a particular geographic area, etc. As indicated by the example filter shown in FIG. 18, the leaderboard 244 has been configured to show the performance of a group of female participants in their 20's. Users 106 may have the ability to individually curate and/or otherwise configure a leaderboard 244, or have the system 100 curate a leaderboard 244 by selecting an appropriate group of participants relative to the user 106. Users 106 may be able to curate their own leaderboards 244 for specific previously recorded classes to create a leaderboard 244 that provides the maximum personal performance incentive to the user 106.

Users 106 may be provided with the ability to deselect the leaderboard 244 entirely and remove it from the user interface 200. In various exemplary embodiments, the exercise machine 102 may incorporate various social networking aspects such as allowing the user 106 to follow other participants, or to create groups or circles of participants. User lists and information may be accessed, sorted, filtered, and used in a wide range of different ways. For example, other users can be sorted, grouped and/or classified based on any characteristic including personal information such as age, gender, weight, or based on performance such as current power output, speed, or a custom score.

The leaderboard 244 may be fully interactive, allowing the user 106 to scroll up and down through the participant rankings, and to select a participant to access their detailed performance data, create a connection such as choosing to follow that participant, or establish direct communication such as through an audio and/or video connection. The leaderboard 244 may also display the user's personal best performance in the same or a comparable class, to allow the user 106 to compare their current performance to their previous personal best. In some examples, such performance information may also be displayed in one or more of the display bars 240, 242. The leaderboard 244 may also highlight certain participants, such as those that the user 106 follows, or provide other visual cues to indicate a connection or provide other information about a particular entry on the leaderboard 244.

In various exemplary embodiments, the leaderboard 244 will also allow the user 106 to view their position and performance information at all times while scrolling through the leaderboard 244. For example, if the user 106 scrolls up toward the top of the leaderboard 244 such as by dragging their fingers upward on the display 104, when the user 106 reaches the bottom of the leaderboard 244, it will lock in position and the rest of the leaderboard 244 will scroll underneath it. Similarly, if the user 106 scrolls down toward the bottom of the leaderboard 244, when the user's window reaches the top of the leaderboard 244, it will lock in position and the rest of the leaderboard 244 will continue to scroll underneath it.

In various exemplary embodiments, the system 100 may calculate and/or display one or more custom scores to describe one or more aspects of the users' performance. One example of such a custom score would be a decimal number calculated for a particular class or user session. Such a score could also be calculated using performance data from some or all classes or sessions over a particular period of time. In any of the examples described herein, such a custom score may be calculated and/or otherwise determined by the system 100 and/or by one or more processors of the exercise machine 102 based at least partly on an amount of time elapsed during an exercise class, a total output or total energy expended by the user 106 during such a class, and/or a number of exercise classes that the user 106 participated in within a given time period.

In various exemplary embodiments, performance information about other users may also be presented on the leaderboard 244 or in any other format, including formats that can be sorted by relevant performance parameters. Users may elect whether or not to make their performance available to all users, select users, and/or instructors, or to maintain it as private so that no one else can view it.

In various exemplary embodiments the user interface 200 may also present one or more video streams from a range of different sources. For example, one video stream may be the live or archived class content shown in the primary window 236, while one or more additional video streams may be displayed in other windows on the display 104. The various video streams may include live or recorded streaming instructor video or any other video content, including one or more live video chat streams. Such video content may include instructional information such as informational or demonstration content regarding how to perform a particular exercise. It may also include visual cues for the user 106 to follow in performing their exercise, such as timing indicators, counts, etc.

In further examples, one or more of the in-class user interfaces 200 illustrated in FIGS. 16-18 may be configured to provide one or more notifications 246 to the user 106 during the exercise class. For example, one or more of the sensors 147 may be configured to sense, detect, and/or otherwise determine a load applied to at least one of the belt 120, the deck 112, one or both of the motors 114, 118, and/or other components of the exercise machine 102. Such sensors 147 may send one or more signals to the processor or other digital hardware 148 of the exercise machine 102 indicative of such a load and/or of a change in such a load. At least partly in response to such signals, the processor or other digital hardware 148 of the exercise machine 102 may cause the notification 246 to be displayed on the display 104 together with at least part of the exercise class selected by the user 106. Such signals may indicate, for example, that the user 106 has stepped off of the belt 120 during a run segment of the exercise class. Accordingly, such notifications 246 may indicate that the user 106 has stepped off of the belt 120 and/or the deck 112. Such notifications 246 may also request a response from the user 106. For example, such notifications 246 may request the that the user 106 confirm that he/she is not hurt and/or that the user 106 would like to continue exercising.

Figure 19:
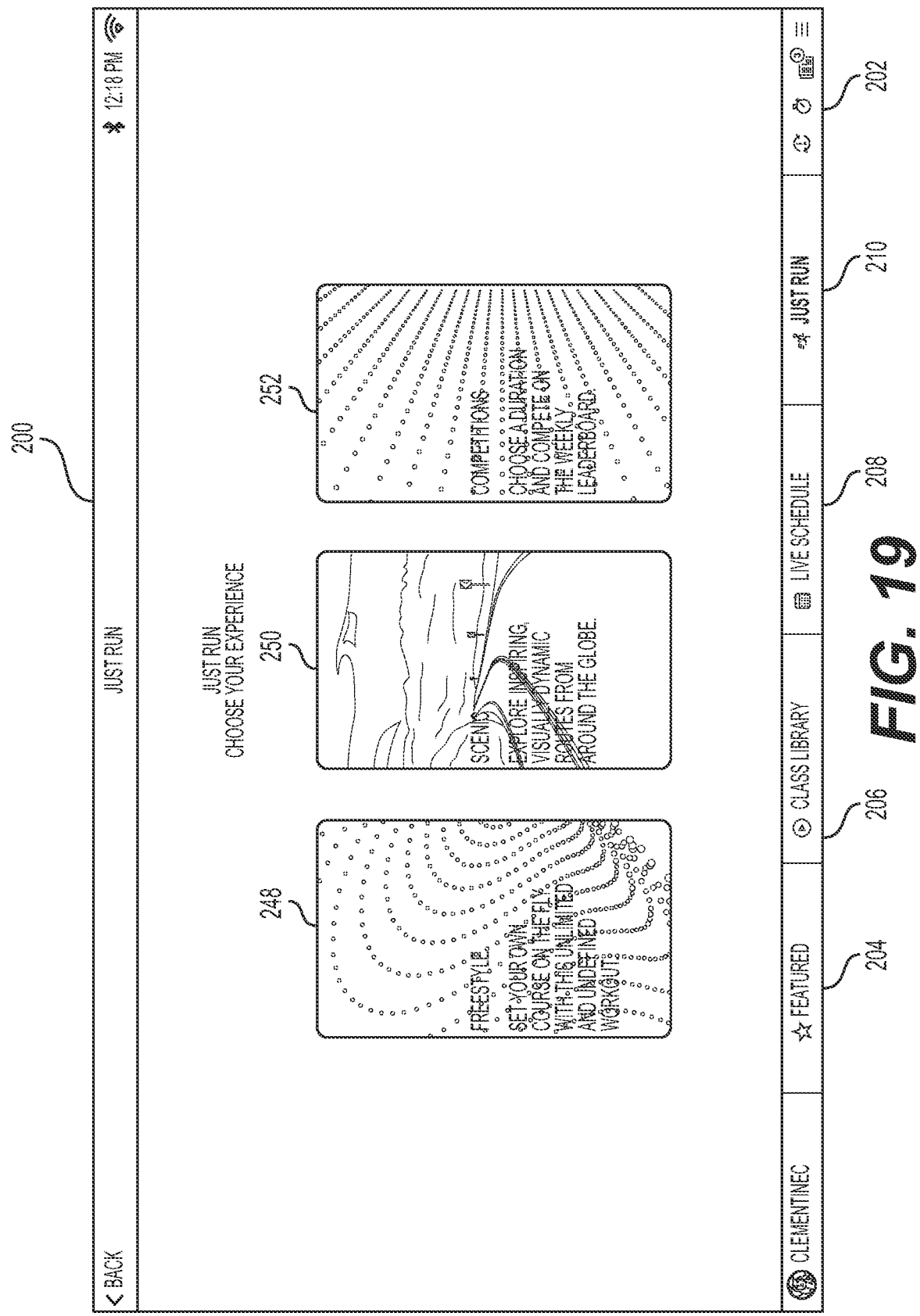
FIG. 19 illustrates another example user interface of the present disclosure including information related to a just run user experience.
Figure 20:
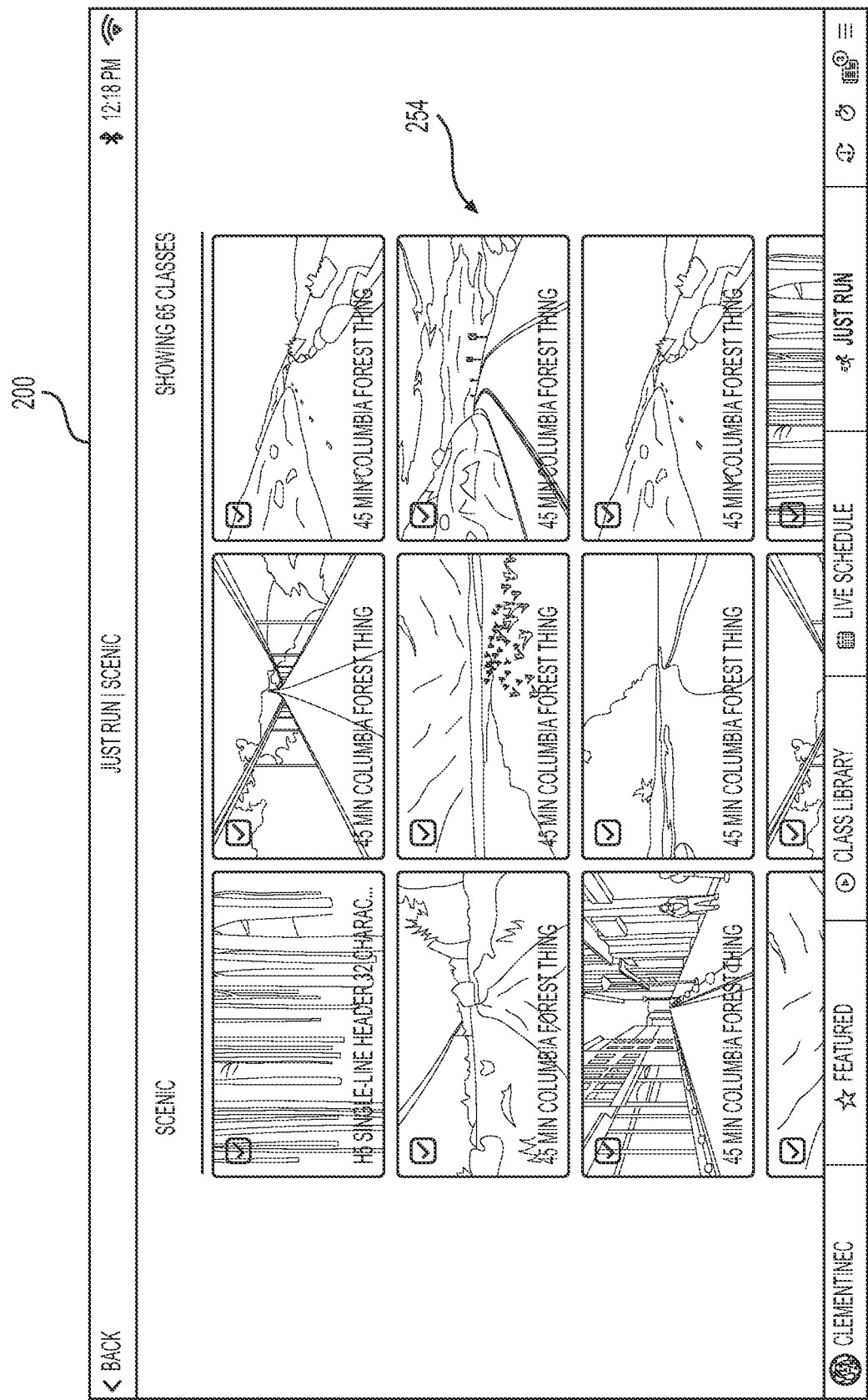
FIG. 20 illustrates still another example user interface of the present disclosure including information related to scenic running paths associated with the just run user experience.
Figure 21:
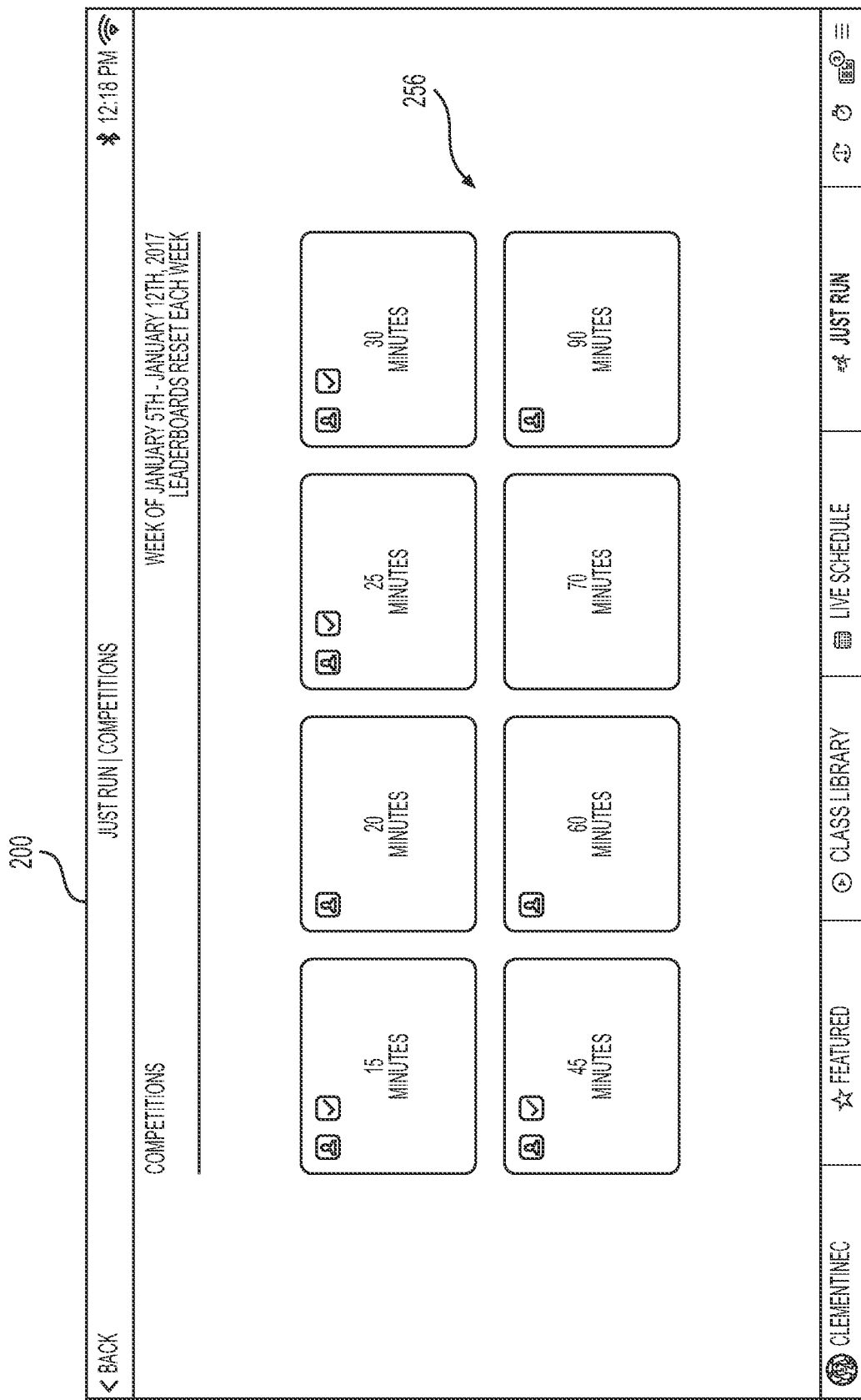
FIG. 21 illustrates yet another example user interface of the present disclosure including information related to competitions associated with the just run user experience.

As illustrated by the example user interfaces 200 shown in FIGS. 19-21, if the user 106 selects the fourth tab 210 associated with the "just run" functionality of the exercise machine 102, the system 100 may provide a user interface 200 showing information related to available quick-start running exercises/applications. For example, the user interface 200 may include one or more icons or thumbnails 248, 250, 252 allowing the user 106 to select a desired exercise regimen. The freestyle icon 248 may, for example, enable the user 106 to set his/her own incline, belt speed, running course, and/or other parameters, and may enable the user 106 to exercise in an undefined and unlimited way (e.g., without a specific exercise class being displayed on the display 104). The scenic icon 250, may be similar to the freestyle icon 248 in that it may enable the user 106 to exercise without a specific exercise class being displayed on the display 104. However, in response to receiving an input indicative of the selection of the scenic icon 250, the user interface 200 may present a plurality of additional icons or thumbnails 254 corresponding to respective scenic running trails stored in a memory of the exercise machine 102. Such icons or thumbnails 254 are illustrated in FIG. 20. Upon selecting one of the icons or thumbnails 254, the user interface 200 may display the selected running trail on the display 104 as the user 106 exercises on the treadmill 102. Further, the competitions icon 252 may enable the user 106 to perform a relatively high-intensity workout without a specific exercise class being displayed on the display 104. For example, in response to receiving an input indicative of the selection of the competitions icon 252, the user interface 200 may present a plurality of additional icons or thumbnails 256 corresponding to respective time-based challenges or competitions stored in a memory of the exercise machine 102. Such icons or thumbnails 256 are illustrated in FIG. 21. Upon selecting one of the icons or thumbnails 256, the user interface 200 may display belt speed, deck incline, output, elapsed time, mile pace, calories burn, and/or other performance parameters or other information on the display 104 associated with the selected competition.

Figure 22:
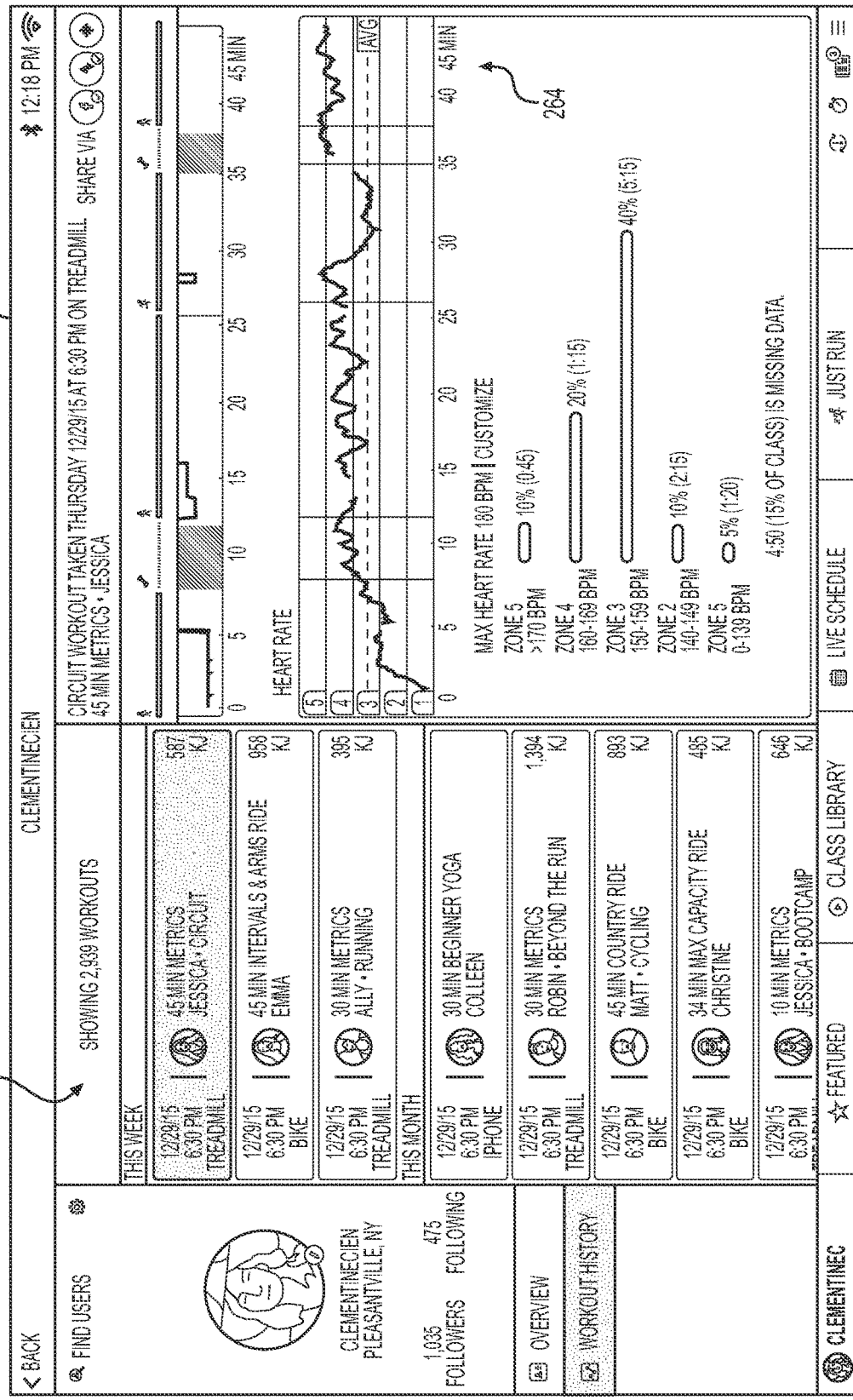
FIG. 22 illustrates a further example user interface of the present disclosure including performance information associated with a particular exercise class.
Figure 23:
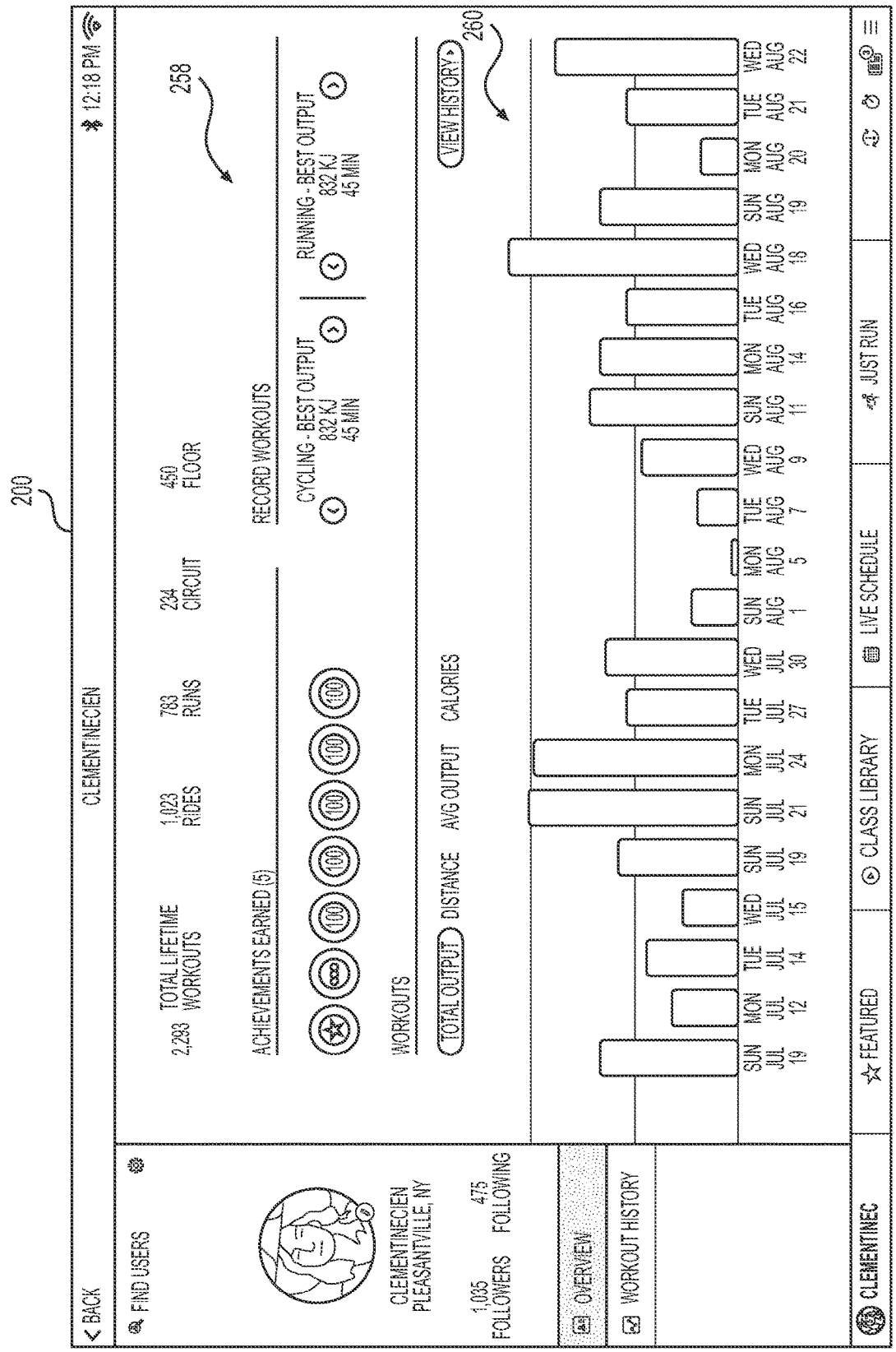
FIG. 23 illustrates another example user interface of the present disclosure including performance information associated with a particular exercise class.
Figure 24:
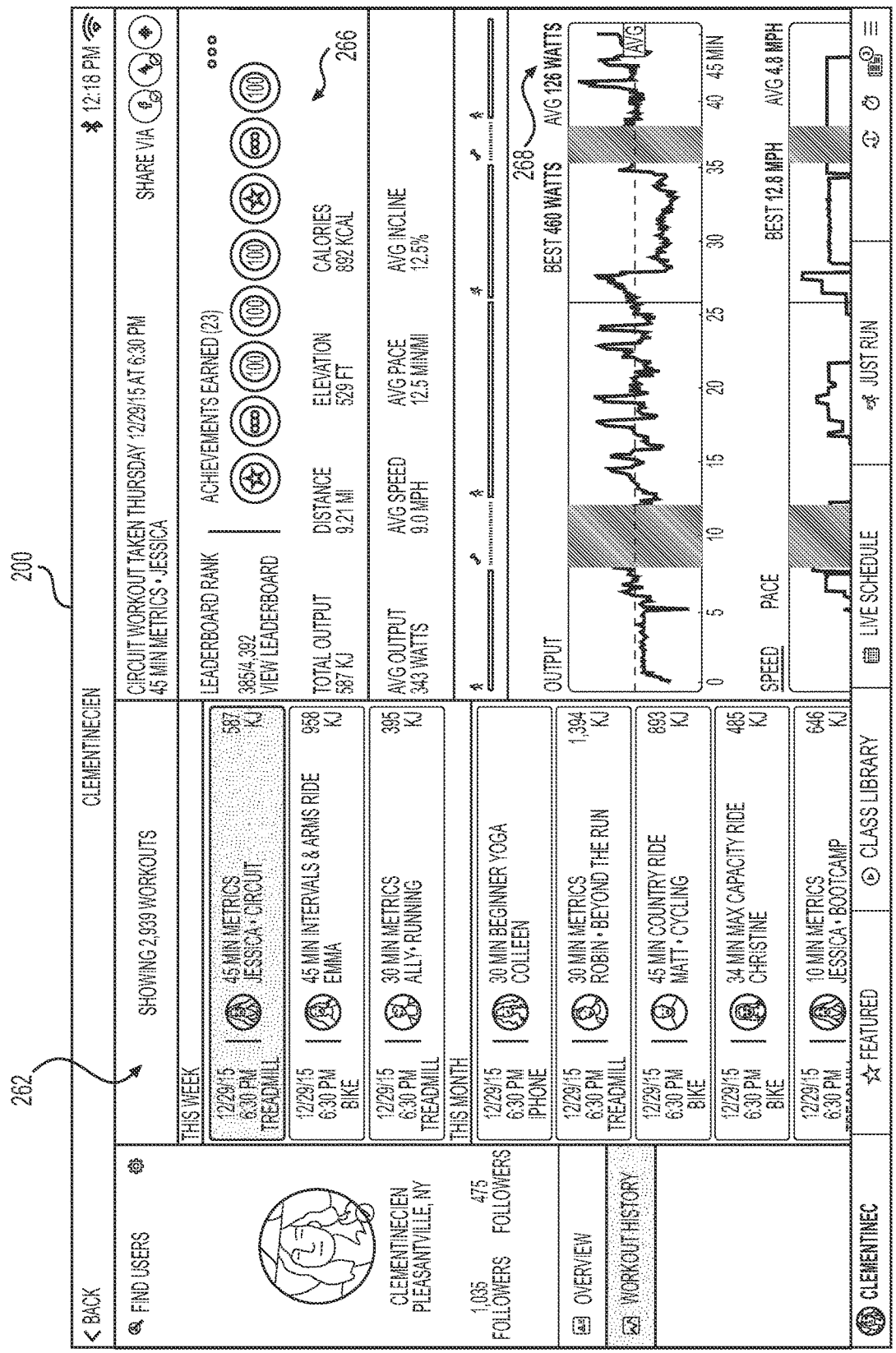
FIG. 24 illustrates still another example user interface of the present disclosure including performance information associated with a particular exercise class.
Figure 25:
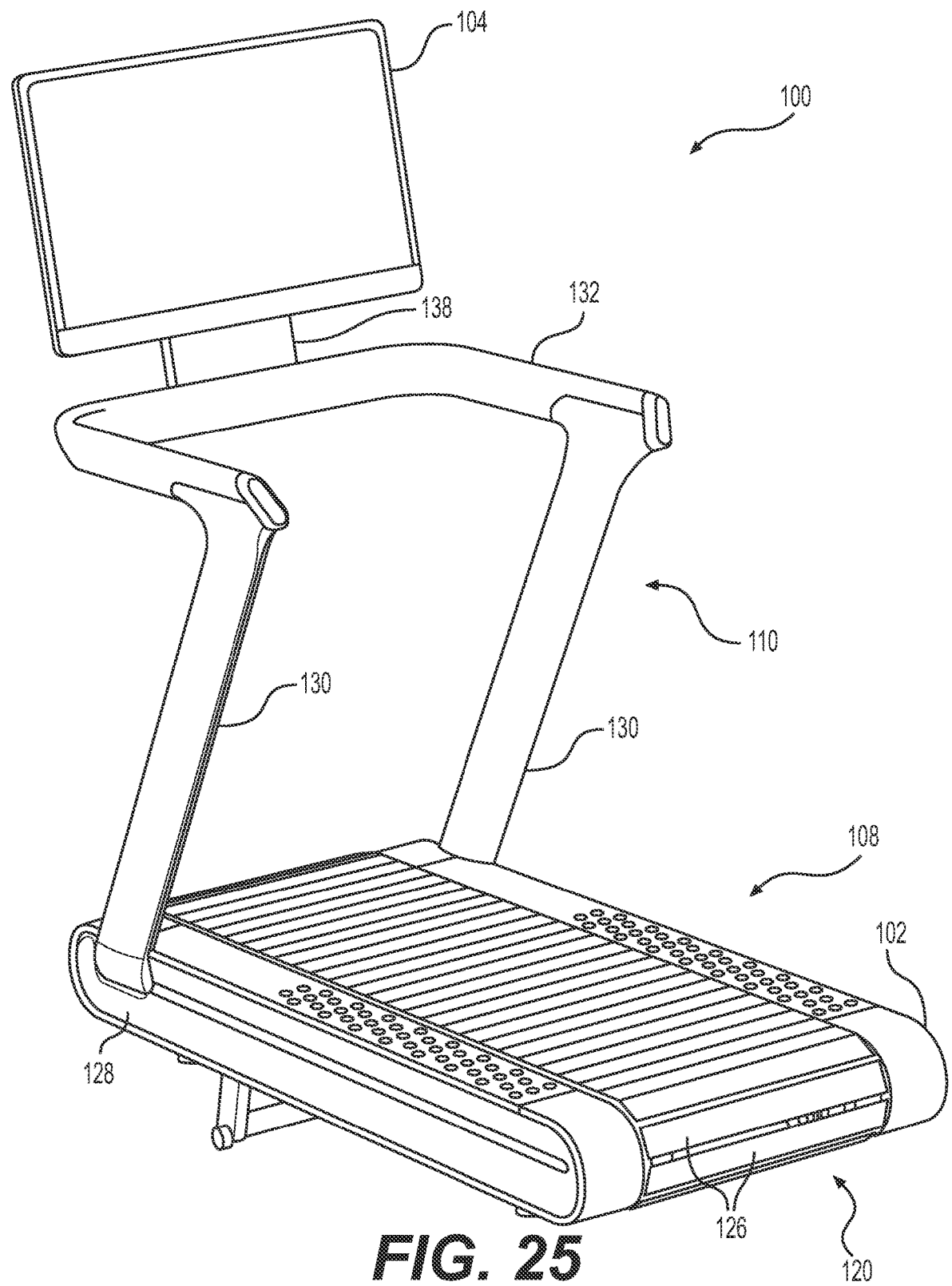
FIG. 25 illustrates an exercise machine according to still another example embodiment of the present disclosure.

FIGS. 22-24 illustrate example user interfaces 200 configured to provide performance information to the user 106 before, during, or after a selected exercise class. For example, the user interface 200 illustrated in FIG. 23 provides an overview of information associated with a particular user 106 (e.g., "clementinecein"). As indicated in the user interface 200 of FIG. 23, such information may include, among other things, the number of followers the user 106 has, the number of fellow participants that the user 106 is following, the total lifetime runs, rides, circuits, or other workouts that the user 106 has done, the various achievements or rewards the user 106 has accomplished, personal best output records of the user 106, a timeline of the user's recent workout activity, and/or other such general information associated with the user's workout activities. Such information may be displayed in one or more separate portions or windows 258, 260 of the user interface 200. In further examples, on the other hand, such information may be provided in the user interface 200 in alternative formats, windows, or locations.

The user interfaces 200 illustrated in FIGS. 22 and 24, on the other hand, provide performance metrics, performance information, and/or other more detailed information associated with the workout history of the particular user 106. For example, as indicated in the user interface 200 of FIG. 22, such information may include a listing of workouts or other exercise classes performed by the user 106 in the present week and/or in the present month. Such information may be displayed in a first window 262 of the user interface 200, and may further include a summary of the user's output during each exercise class, the date and time of the class, the instructor, and/or other information. The user interface 200 may also include one or more additional windows 264 and/or other formats useful in providing additional information regarding the workout history of the user 106. For example, such an additional window 264 may provide specific performance metrics (e.g., a heart rate trend line, a segmented timeline, an average heart rate, a total output, and/or other performance metrics) associated with a specific one of the previous workouts shown in the first window 262.

Similarly, as illustrated in FIG. 24, one or more additional user interfaces 200 providing information associated with the workout history of the particular user 106 may include the window 262 described above, as well as one or more additional windows 266, 268 providing the achievements, output trends, and/or other workout information. For example, the window 266 may display the total output, distance run, elevation ascended, calories burned, average output and/or energy expended, average speed, average mile pace, and/or other information associated with a specific one of the previous workouts shown in the first window 262. The window 266 may also display the leaderboard rank of the user 106 corresponding to the specific one of the previous workouts, as well as various achievements earned for performing the one of the previous workouts. The window 268, on the other hand, may provide speed, output, and or other trend lines associated with the specific one of the previous workouts. As a result, the user interfaces 200 illustrated in FIGS. 22-24 may provide the user 106 with relatively detailed performance information that can be used by the user 106 to improve his/her overall health and/or abilities. Any of the information provided via the user interfaces 200 described herein may be stored in a memory or other component of the digital hardware 148 of the exercise machine 102 and/or may be stored remotely.

Figure 5:
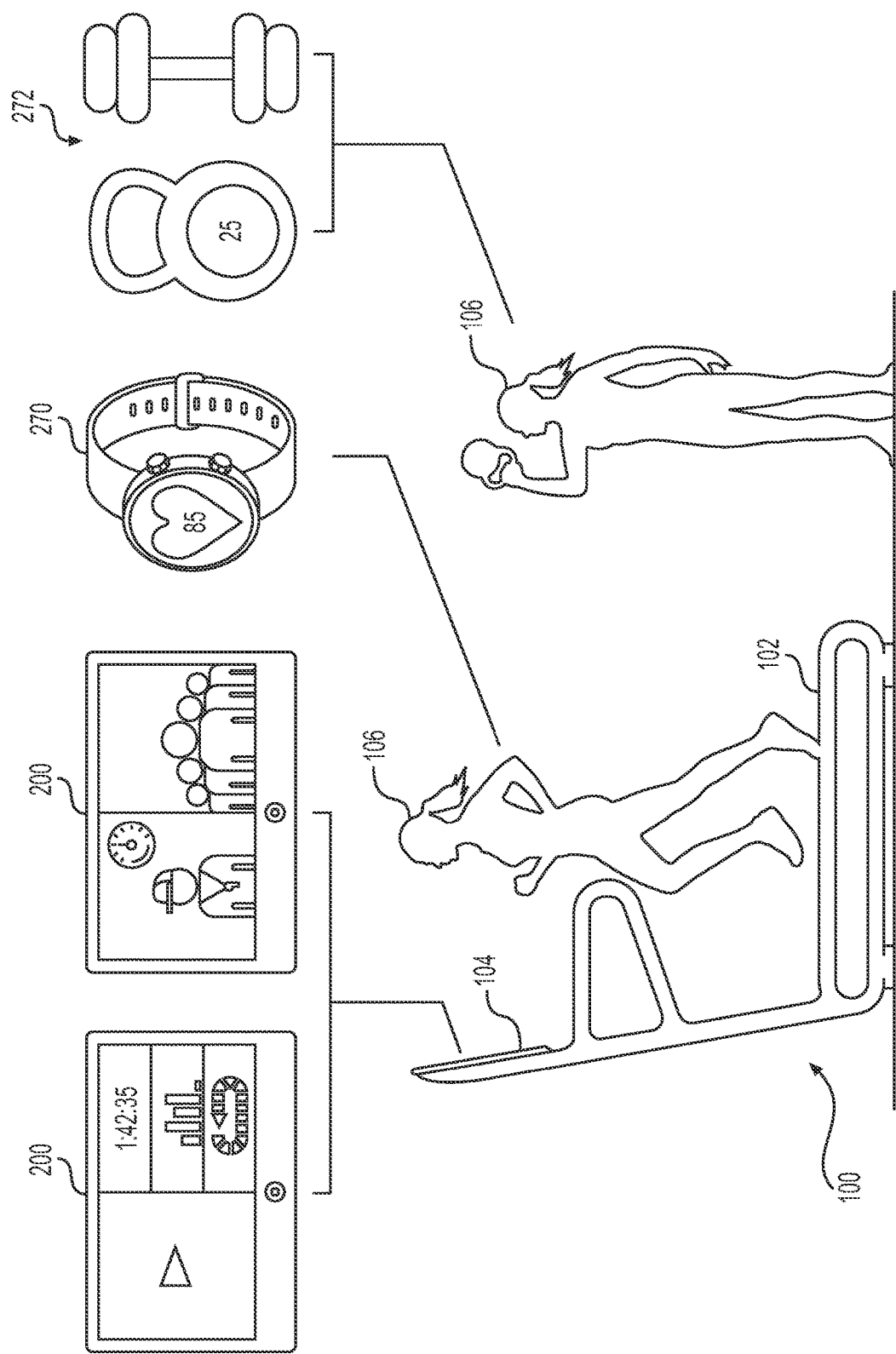
FIG. 5 is an illustration showing an exemplary exercise machine as disclosed herein including illustrations of exemplary information displayed on a display screen, a personal digital device, as well as weights and other accessory devices.

The performance-focused user interfaces 200 illustrated in FIGS. 22-24 may also be configured to provide information obtained from various additional sources. For example, data regarding user performance may be gathered from a variety of sources in addition to the various sensors 147 on the primary exercise machine 102. As illustrated in FIG. 5, other exercise machines 102 and devices used during an exercise class may each include one or more sensors to gather information regarding user performance. The user 106 may also use a variety of other clothing or devices attached to their body (e.g., a watch, a wrist band, a head band, a hat, shoes, etc.) including one or more additional sensors 270. The user 106 may also use other exercise equipment 272 such as weights, resistance bands, rollers, or any other suitable equipment, and such exercise equipment 272 may also include one or more such additional sensors 270. Data from all of these sources may be gathered by the local system 100 and analyzed to provide user performance feedback.

One challenge with certain types of data gathered from such sensors 270 is determining the proper context for interpreting the data so that accurate information regarding user performance can be derived. For example, a sensor 270 worn on the user's wrist may provide data indicating that the user's wrist performed a series of movements consistent with several different exercises, but it may be difficult or impossible to derive which exercise the user 106 was actually performing. Without context, data showing that the user's wrist moved up and down may indicate that the user 106 was running or they may simply have been moving their arm. As a result, performance data derived from such sensors 270 can be very inaccurate.

In various exemplary embodiments, data from a variety of sensors 270 on exercise equipment 272 such as free weights and on the users' body can be gathered, and the system 100 can use information regarding the instructor-led group fitness class to improve accuracy by providing context for the interpretation of sensor data gathered from all sources. If the class instructor has, for example, directed users 106 to do push-ups, the system 100 can assume that sensed movement consistent with a push-up is actually a push-up and interpret the sensor data accordingly. The context provided by the instructor-led group fitness class can substantially improve the resulting performance data.

Accordingly, the one or more user interfaces 200 described with respect to at least FIGS. 22-24 may also provide one or more additional windows that can be used to display any of the performance data and/or other information obtained from the sensors 270 and/or the exercise equipment 272. Such additional windows may also be configured to display a range of content including additional performance data, information about the class, instructor, other participants, etc., or secondary video streams. Such additional windows can allow the user 106 to see a range of information regarding other current or past participants to compare performance, and open or close voice or video chat streams or other communication channels. In various exemplary embodiments the user 106 can simultaneously access and/or view other content including movies, television channels, online channels, etc. via one or more such additional windows.

In various exemplary embodiments, the user interfaces 200 described herein may be run through a local program or application using a local operating system such as an Android or iOS application, or via a browser-based system. Any of the performance metrics or other information described herein with respect to the various user interfaces 200 may also be accessed remotely via any suitable network such as the internet. For example, users 106 may be able to access a website from a tablet, mobile phone, computer, and/or any other digital device, and such users 106 may be able to review historical information, communicate with other participants, schedule classes, access instructor information, and/or view any of the information described herein with respect to the various user interfaces 200 through such a website.

User-Generated Content

Figure 8:
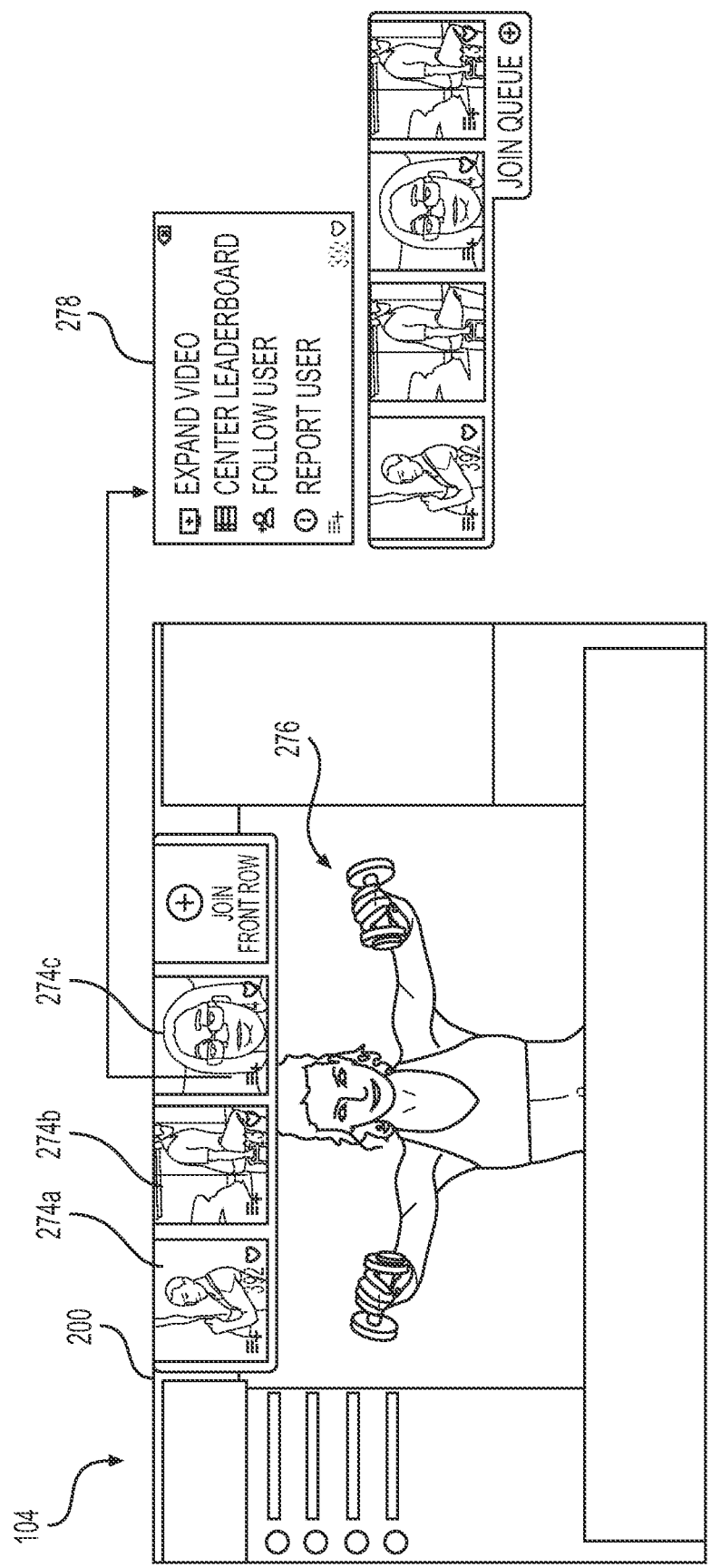
FIG. 8 is an illustration of an exemplary user interface of the present disclosure.

One feature of in-person group exercise classes is the ability to see other participants performing the exercises or other activities in response to the class leader's instructions. This ability to see others performing the same exercises or activities can provide motivation to maintain or improve performance, or help the user confirm that they are performing the proper exercise with proper form. In various exemplary embodiments of the present disclosure, video streams can be displayed on the one or more displays 104 of the respective exercise machines 102 showing other class participants performing the exercises as instructed by an instructor or other class leader. In various exemplary embodiments, such additional video streams may include user-generated content related to the live or previously recorded exercise class content. Referring to FIG. 8 for example, an exemplary embodiment is illustrated wherein video streams of other class participants are displayed in sub-windows 274a, 274b, 274c . . . 274n (collectively "sub-windows 274") across a top portion of a user interface 200 shown on the display 104. Such sub-windows 274 may be displayed on the display 104 while an instructor is displayed in a primary window 276 of the user interface 200. If the class is a live class, such content may be streamed live. If the class is an archived class, such content may be streamed live if the other class participant is taking the class at the same time, or may be archived content from when the other class participant previously took the class. One or more of such video streams may be displayed on the one or more displays 104 described herein. Additionally, by touching, selecting, and/or otherwise providing input via one of the sub-windows 274, the user interface 200 may provide an additional window 278 enabling the user 106 to expand a video associated with the selected sub-window, follow a user associated with the selected sub-window, and/or perform one or more additional actions associated with the selected sub-window.

In various exemplary embodiments, the user 106 may also be able to provide feedback regarding such user generated content. For example, the user 106 may be able to input positive or negative feedback such as indicating that they like or dislike the user-generated content by clicking on an icon provided via the additional window 278 indicating their opinion or otherwise inputting their opinion.

In various exemplary embodiments, the user 106 may also choose whether or not to display any such user-generated content. If user-generated content is displayed, which user-generated content is displayed to a particular user 106 can be determined several different ways. In various exemplary embodiments, the user-generated content may be chosen by the user 106 by selecting it from among the available user-generated content for a particular exercise class currently be displayed via the display 104. Such user-generated content may also be chosen by the class instructor or one or more content editors, it may be presented via a content queue ordered based on any suitable criteria, or it may be chosen by the system 100 based on one or more suitable criteria. For example, the user-generated content to be displayed could simply be a time-based queue of available user-generated content without regard to quality.

In various exemplary embodiments, the user-generated content to be displayed may be selected to provide the best quality user-generated content available for a particular selected exercise class at the time of viewing. At the time the class is aired live, the available user-generated content would be limited to live streamed content generated during the class itself. For archived classes, the available user-generated content could include all content generated by every user that has participated in the class at any time. The user-generated content to be displayed for an archived class may be based on accumulated ratings for that user-generated content over time, or on any other measure of popularity. Such a methodology would result in an improvement of the user-generated content displayed with any archived class over time, as the user-generated content receiving the best feedback would be selected for display while user-generated content that did not receive positive feedback would not be displayed.

Local System

As noted above, an example local system 100 may include an exercise machine 102, and a range of associated sensing, data storage, processing, and/or communications components (e.g., digital hardware 148). In example embodiments, such components may be disposed onboard the exercise machine 102 itself and/or located near the exercise machine 102. The processing, data storage, and/or communications components may be located within a housing of the display 104 to form a single integrated onboard computer and display screen, or they may be separately housed locally on or near the exercise machine 102. Such an example local system 100 may communicate with one or more remote servers through wired or wireless connections using any suitable network or protocol.

Additionally as noted above, an example exercise machine 102 may be equipped with various sensors 147 to measure, sense, detect, and/or otherwise determine information relating to user performance metrics. Such information may be stored in memory associated with the digital hardware 148 and/or in memory associated with the remote servers, and such information may be used by the processors and/or other components of the digital hardware 148 to determine one or more of the performance metrics described herein and/or to determine other performance information. The exercise machine 102 may also be equipped with or connected to various data input devices or other user interfaces such as the display 104, touchscreens, video cameras, and/or microphones.

The sensors 147 and other input devices can communicate with local and/or remote processing and storage devices via any suitable communications protocol and network, using any suitable connection including wired or wireless connections. In various exemplary embodiments, local communication may be managed using a variety of techniques. For example, local communication may be managed using wired transport with a serial protocol to communicate between sensors and the console. Local communication may also be managed using a wireless communication protocol such as the ANT or ANT+ protocol. ANT is a 2.4 GHz practical wireless networking protocol and embedded system solution specifically designed for wireless sensor networks (WSN) that require ultra-low power. Advantages include extremely compact architecture, network flexibility and scalability, ease of use and low system cost. Various combinations of wired and wireless local communication may also be used.

Access to any appropriate communications network such as the internet may be used to provide information to and receive information from other exercise machines 102 or other resources such as a backend system or platform. In various exemplary embodiments, the local system 100 can access and display information relating to other users either directly through a distributed platform or indirectly through a central platform regardless of their location. Such other users may be present at the same location or a nearby location, or they may be at a remote location.

Content Creation and Distribution

Content for delivery to users 106 including live and archived exercise classes, live and archived instructional content such as video content explaining how to properly perform an exercise, scenic or map-based content, videos, and/or animations that can be rendered in three-dimensions from any angle may be created and stored in various local or remote locations and shared across the networked exercise system. Such an example networked exercise system is illustrated in at least FIG. 9. This overview of such a networked exercise system is exemplary only and it will be readily understood that example embodiments of the present disclosure can be implemented through a variety of different system architectures using centralized or distributed content creation and distribution techniques.

In various exemplary embodiments, the networked exercise system 100 is managed through one or more networked backend servers and includes various databases for storage of user information, system information, performance information, archived content, etc. Users' local systems 100 are in communication with the networked backend servers via any appropriate network, including without limitation the internet. As an example of an alternative distribution approach, in various exemplary embodiments the backend servers could be eliminated and data could be communicated throughout the system in a distributed or peer-to-peer manner rather than via a central server network. In such a system, performance data may be broken up into small packets or "pieces" and distributed among user devices such that complete data sets are quickly distributed to all devices for display as required.

Figure 9:
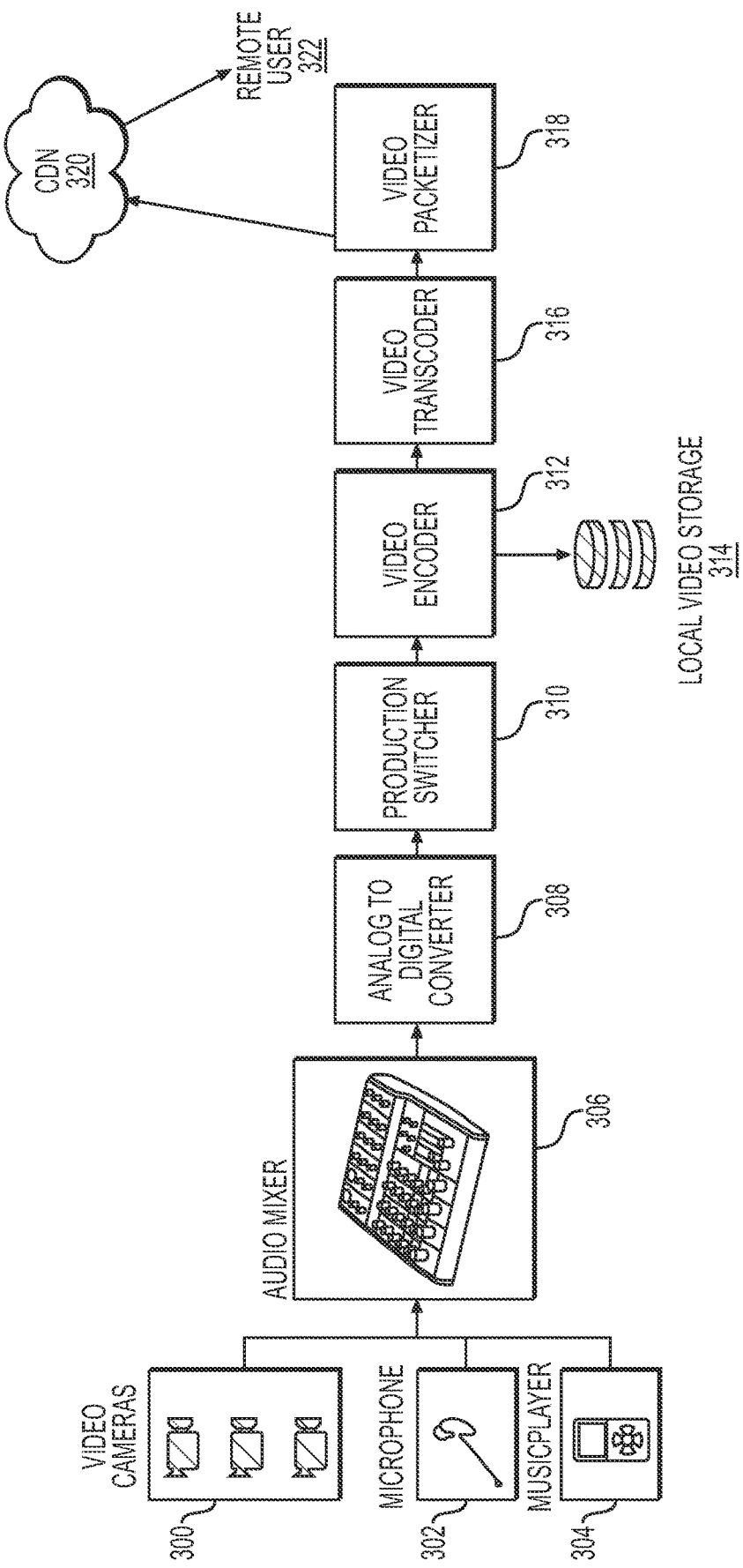
FIG. 9 is a schematic illustration showing exemplary components used for content creation and/or distribution.

Content for distribution through the network can be created in a variety of different ways. Content recording locations may include professional content recording studios or amateur and home-based locations. In various exemplary embodiments, recording studios may include space for live instructor-led exercise classes with live studio participation, or may be dedicated studios with no live, in-studio participation. As shown in FIG. 9, recording equipment including one or more video cameras 300, microphones 302, mp3 players or other music players 304, and/or other components and can be used to capture the instructor and/or participants during the class. Multiple cameras 300 can provide different views, and 3D cameras 300 can be used to create 3D content. In various exemplary embodiments, content may also be generated locally by users 106. For example, exercise machines 102 may be equipped with recording equipment including microphones 302 and cameras 300. Users 106 may generate live or recorded classes that can be transmitted, stored in the system, and distributed throughout the network.

With continued reference to FIG. 9, class content may be generated by providing outputs of the one or more video cameras 300, microphones 302, and/or music players 304 as inputs to an audio mixer 306. The audio mixer 306 may output content to an analog to digital converter 308, which may provide converted data to a production switcher 310. The production switcher 310 may send the production video to a video encoder 312, which may store the encoded video to a local storage device 314, and may also send it to a video transcoder 316. The video transcoder 316 may output transcoded data to a video packetizer 318, which may then send a packetized data stream out through a content distribution network 320 to remote system users 322. In various exemplary embodiments, instructors and/or users 106 may be provided with access to a content creation platform that they can use to help them create content. Such a platform may provide tools for selecting and editing music, managing volume controls, pushing out chat or other communications to users.

As described above, through the display 104 and/or other user interface on their exercise machine 102, users 106 may access lists, calendars, and schedules of live and recorded exercise classes available for delivery through the display 104. In various exemplary embodiments, once the user 106 selects a class, the local system 100 accesses and displays a primary data stream for the class. This primary data stream may include video, music, voice, text, or any other data, and may represent a live or previously recorded cycling class. The local system 100 may be equipped for hardware video accelerated encoding/decoding to manage high definition video quality at up to 1080 pixels based on existing technology. The local system 100 may automatically adjust bitrate/quality of the data stream for the class in order to bring participant the highest quality video according to user's bandwidth/hardware limitations.

In various exemplary embodiments, networked exercise systems and methods of the present disclosure may include multi-directional communication and data transfer capabilities that allow video, audio, voice, and data sharing among all users and/or instructors. This allows users to access and display multi-directional video and audio streams from the instructor and/or other users regardless of location, and to establish direct communications with other users to have private or conferenced video and/or audio communications during live or recorded classes. Such data streams can be established through the local system 100 for presentation via the one or more displays 104 via one or more of the user interfaces 200 described above. In various exemplary embodiments, users 106 can manage multiple data streams to select and control inputs and outputs. The local system 100 may allow the user 106 to control the volume of primary audio stream for the class as well as other audio channels for different users or even unrelated audio streams such as telephone calls or their own music selections. For example, this would allow a user 106 to turn down the instructor volume to facilitate a conversation with other users.

For live classes, in various exemplary embodiments the instructor may have the ability to communicate with the entire class simultaneously or to contact individual users, and solicit feedback from all users regardless of location in real-time. For example, instructors could ask users verbally, or text a pop-up message to users 106, seeking feedback on difficulty level, music choice, terrain, etc. Users 106 could then respond through components of the local system 100 by selecting an appropriate response, or providing verbal feedback. This allows instructors to use crowdsourcing to tailor a class to the needs of the participants, and to improve their classes by soliciting feedback or voting on particular class features or elements.

In various exemplary embodiments, instructors may also be able to set performance targets, and the system can measure and display to the user 106 and the instructor their performance relative to the target. For example, the instructor may set target metrics e.g. target power and speed, then display this next to users' readings with a color coding to indicate whether or not the user is meeting this target. The system may allow the instructor to remotely adjust exercise machine settings for individual users 106. In various exemplary embodiments, the exercise machine 102 may also automatically adjust based on information from the user 106, the instructor, or based on performance. For example, the exercise machine 102 may adjust the difficulty to maintain a particular performance parameter such as heart rate within a particular range or to meet a particular performance target.

In various exemplary embodiments, users 106 can control access to their own information, including sensor data, performance metrics, and personal information. Such data can be stored at the local system 100, transmitted for storage and management by a remote system and shared with other users, or stored remotely but not shared with other users. Users 106 may also elect to disclose their presence on the system to other users, or to participate in a class without making their presence known to other users.

In various exemplary embodiments, users 106 can access a list of all or selected current and/or past class participants. Such lists may include performance information for such users, such as total power, speed, steps, cadence, resistance, or a custom score that provides information about relative user performance. Such lists may also include controls to allow the user to open up live streams to the user such as live video chat streams.

System Features and User Resources

In various exemplary embodiments, the networked exercise system and methods may allow users 106 to create accounts and save and manage their performance data. As discussed above, the system may allow users 106 to browse schedules for upcoming live classes, signup for future live streaming classes, and setup reminders. Users 106 may also be able to invite others to participate in a live class, and setup text, email, voice, or other notifications and calendar entries. Users 106 may be able to access system, account, performance, and all other data via web-based or application based interfaces for desktop and/or mobile devices, in addition to the user interface for the local system 100 associated with their exercise machine 102.

In various exemplary embodiments, the system can provide for simultaneous participation by multiple users in a recorded class, synchronized by the system and allowing access to all of the same communication and data sharing features that are available for a live class. With such a feature, the participants simultaneously participating in the same archived class can compete against each other, as well as against past performances or "ghost" participants for the same class.

Figure 10:
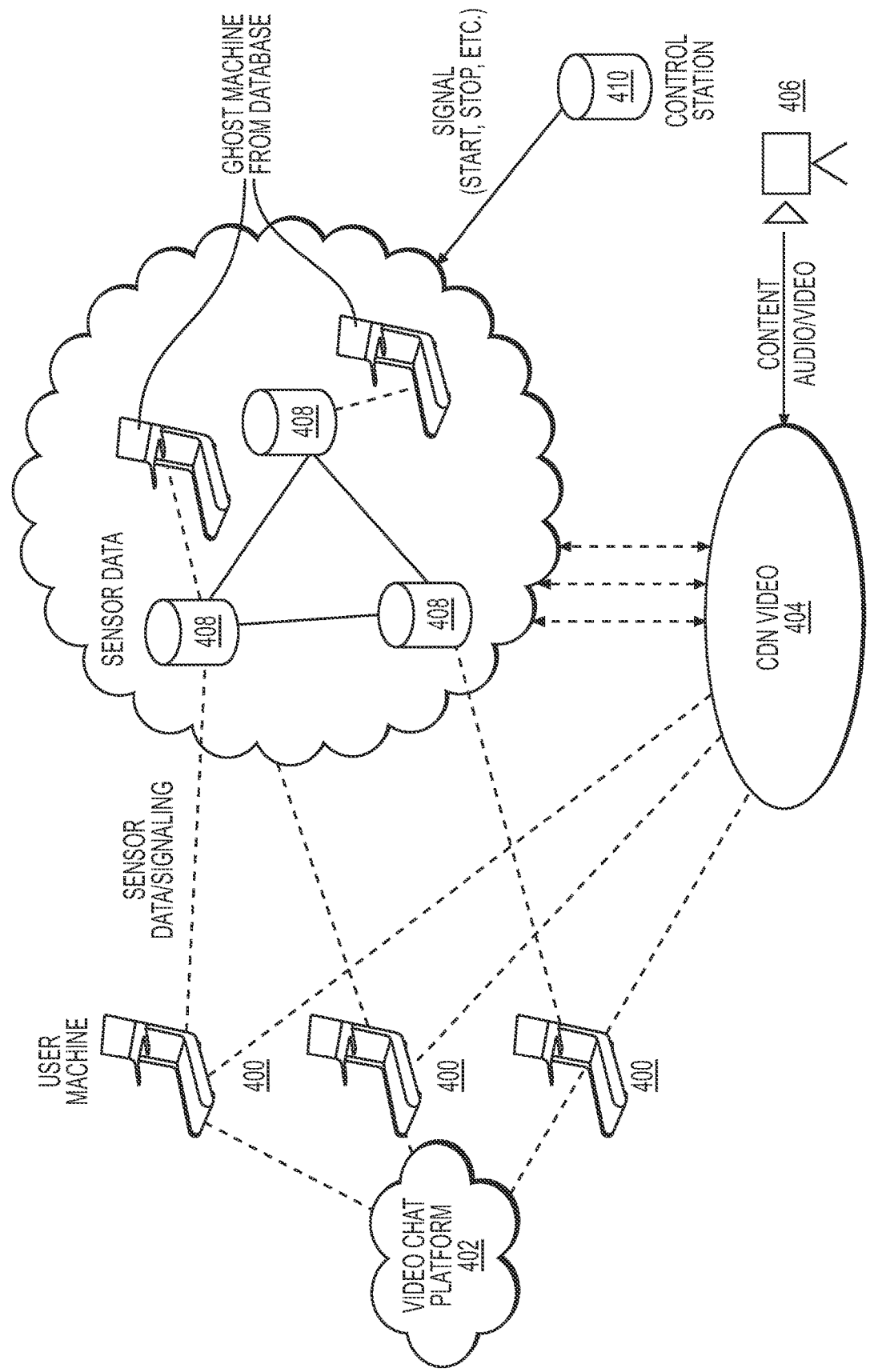
FIG. 10 is a schematic illustration of a basic network architecture according to an example embodiment of the present disclosure.
Figure 11:
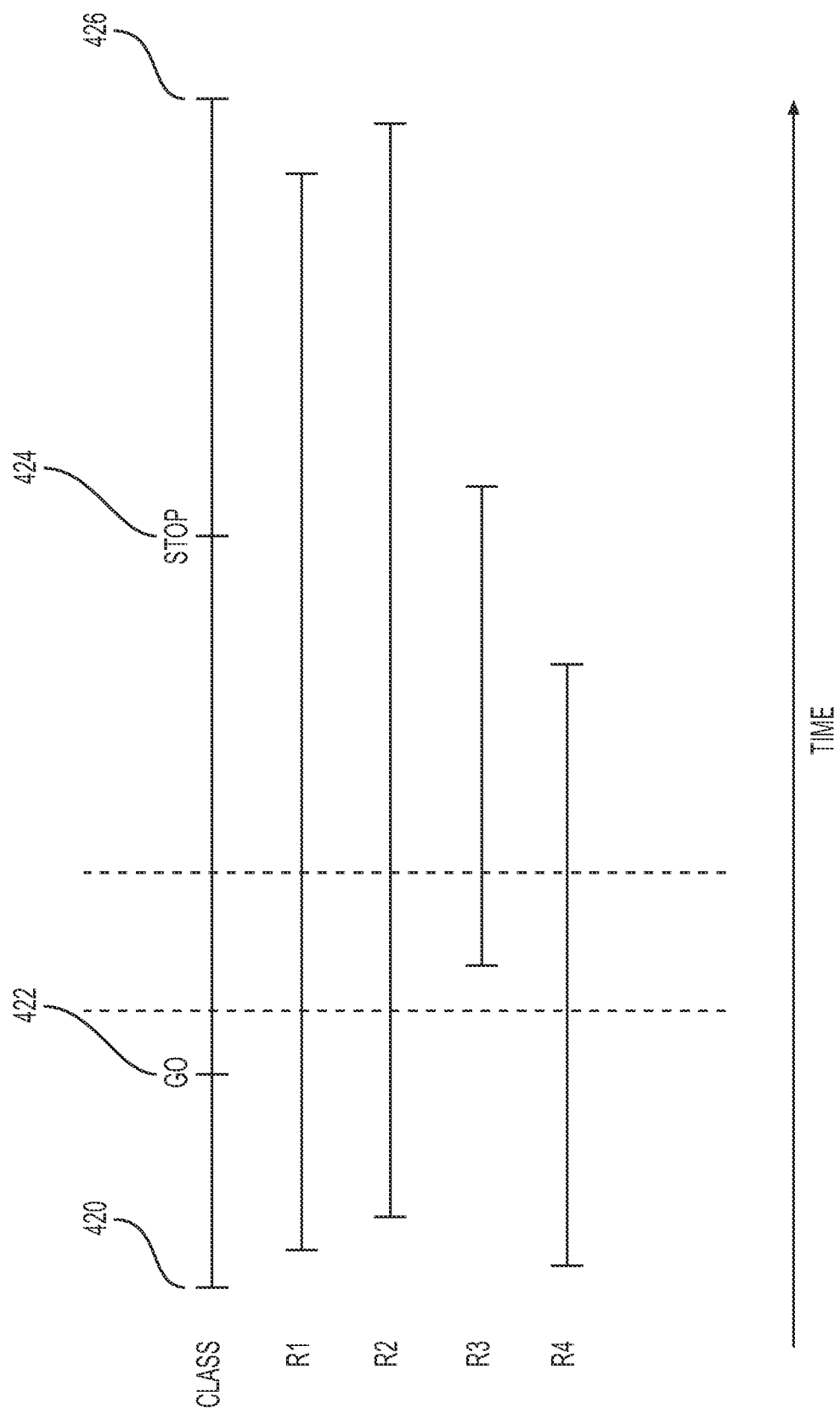
FIG. 11 illustrates a chart showing an example embodiment of a method for synchronizing data among different users participating in the same live or on-demand exercise class.

Referring to FIGS. 10 and 11, the system may be configured to feed synchronized live and/or archived video content and live and/or archived sensor data to users over the network. In various exemplary embodiments, the networked exercise system may be configured with a plurality of user exercise equipment 400 in communication with a video chat platform 402, a video content distribution network 404 that receives audio video content from one or more content sources 406. The user exercise equipment 400 may also be in communication with various other networks and servers. For example, the user exercise equipment 400 may exchange sensor and performance data and/or signaling with various databases 408, including historical or "ghost participant" data. A control station may provide signals via the network to control the collection, storage, and management of data across the system.

One challenge for the use of comparative data from live and/or historical sources is synchronization, since some users 106 may start exercising prior to the start of the actual class, while others may join after the class has started. In order to provide accurate data regarding class performance for the leaderboard, including archived performance data, each class may have a specific "go" or start signal that serves as the starting time point for the data comparison. Archived performance data may be calibrated to the same "go" signal as live participant data, allowing for comparative data to be presented through a leaderboard or other display through the end of the class. A "stop" signal at the end of the class marks the end time point for the performance comparison for both live and archived performance data. If a participant joins the class after the "go" signal, their data can be synched correctly starting at the time they join the class.

FIG. 11 shows various events relative to time, which is increasing from left to right on the scale at the bottom. The timeline for the class itself, whether live or archived, is shown at the top, with timelines for four different participants below it. The video being delivered for a live or archived class may begin before the actual class starts at the video start point 420. The GO signal point 422 indicates the start of the class or the class's comparison period, the STOP signal point 424 indicates the end of the class or the end of the class's comparison period, and the end video point 426 indicates the end of the video stream. For Participants 1, 2, and 4, who all start exercising before the GO signal point, the GO signal serves as their starting time point for class performance metrics. For Participant 3, the point in time when they actually start will serve as their starting time point for class performance metrics. For Participants 1, 2, and 3 who continued past the STOP signal point, their end point for class performance metrics will be the STOP signal point, while the end point for Participant 4 will be the time when they actually stopped exercising.

Using such a system, live and past performance data for the user or other participants can be provided during a class in a range of numerical and graphical formats for comparison and competition. Live and past performance data or target performance data for the user can also be displayed simultaneously to allow users to compare their performance to a benchmark in real time during or after a class. In various exemplary embodiments, the system may also allow users to establish handicapping systems to equalize the competition among different users or user groups allowing for broad based competitions.

In various exemplary embodiments, the system may combine information from multiple users 106 to produce a combined or collective result. For example, different user's performance information could be combined to produce a single performance measurement such as in a relay type race, where the times for different users are collected and combined into a single time or score for a team.

In various exemplary embodiments, the system may also combine the user's performance from two or more different exercise machines 102 to produce a single output or score. For example, performance information gathered from a bike and a treadmill used sequentially or as part of the same group exercise class may be combined together in a single output that reflects performance data from the plurality of exercise machines 102.

In various exemplary embodiments, a mobile application may allow users on non-networked exercise machines to access the system via a mobile digital device such as a tablet computer or mobile phone and access content, live streams, and other system features. The mobile device could access the system via any appropriate network using a dedicated application or browser.

In various exemplary embodiments, one or more secondary displays may be used by the system to display class content. Using a device such as CHROMECAST or a similar integrated device to enable it to display content provided by the system through the user interface, a secondary display screen may be used to display class content or other content provided by the system. The user interface could automatically detect the availability of such an enabled device and allow the user to select the display screen for particular content.

Various types of rewards and honors can be created for different achievements to create incentives for improving performance or reaching other goals. In various exemplary embodiments, the instructor or users can create mini-competitions for participation by all users or just a selected subset of users such as a group of friends. Competitions such as sprints, hill climbs, maximum power output, etc. can be preset or created in real-time through the user interface. Winners can be rewarded with prizes such as badges, trophies, or biking specific honors such as a green or yellow jersey. Competitions can be created within a class or session, or across multiple classes or sessions.

Clauses

The example clauses A-T noted below set forth example embodiments of the present disclosure. Any of the clauses below, or individual features thereof, may be combined in any way. Further, the descriptions included in any of the example clauses below may be combined with one or more features described above or illustrated in FIGS. 1-35. The clauses noted below are not intended to narrow the scope of the present disclosure in any way, and merely constitute examples of the various embodiments described herein.

A: In an example embodiment of the present disclosure, a method includes providing information about available exercise classes to a processor associated with a first exercise machine, the first exercise machine being located at a first remote location; receiving, from a first user of the first exercise machine and via the processor, a selection of one of the available exercise classes; providing, via a network and to the processor, digital content comprising the one of the available exercise classes; receiving, via the network, a first plurality of performance parameters detected at the first exercise machine during display of at least part of the one of the available exercise classes on a display associated with the first exercise machine, the at least part of the one of the available exercise classes requiring participants to run on a treadmill; receiving, via the network, a second plurality of performance parameters detected at a second exercise machine during display of the at least part of the one of the available exercise classes on a display associated with the second exercise machine, the second exercise machine being located at a second remote location different from the first remote location; providing, via the network, at least one parameter of the second plurality of performance parameters to the processor, wherein the processor is configured to cause the at least one parameter of the second plurality of performance parameters to be displayed on the display associated with the first exercise machine together with a corresponding at least one parameter of the first plurality of performance parameters.

B: In the method of clause A, the first and second exercise machines comprise treadmills, and the one of the available exercise classes comprises a running class performed by an instructor at least partially on a treadmill.

C: In the method of clause A or B, the one of the available exercise classes comprises a live class streamed to the first and second exercise machines substantially in real-time.

D: In the method of clause A, B, or C, the first plurality of performance parameters includes at least one of a speed of a belt associated with a deck of the first exercise machine, an incline of the deck, and a mile pace of the first user.

E: In the method of clause A, B, C, or D, the at least one parameter of the first plurality of performance parameters comprises an amount of energy expended by the first user while running during the at least part of the one of the available exercise classes, and wherein the amount of energy is determined based at least partly on a speed of a belt associated with a deck of the first exercise machine, and an incline of the deck.

F: The method of clause A, B, C, D, or E, further comprises providing, via the network, video chat data to the processor associated with the first exercise machine, wherein the processor is configured to cause the video chat data to be displayed on the display associated with the first exercise machine, in substantially real-time, together with the one of the available exercise classes.

G: The method of clause A, B, C, D, E, or F, further comprises receiving, via the network, video chat data from the processor associated with the first exercise machine, and providing, via the network, the video chat data to a processor associated with the second exercise machine, wherein the processor associated with the second exercise machine is configured to cause the video chat data to be displayed on the display associated with the second exercise machine together with the one of the available exercise classes.

H: In the method of clause A, B, C, D, E, F, or G, the processor associated with the first exercise machine is configured to cause the at least one parameter of the second plurality of performance parameters to be displayed on the display associated with the first exercise machine together with the at least part of the one of the available exercise classes.

I: An exercise machine comprises a processor; a first display operably connected to the processor and configured to display content; a deck configured to move relative to a surface supporting the exercise machine; a belt rotatable about the deck; and a sensor operably connected to the processor, the sensor being configured to detect a first performance parameter of a first user running on the belt of the exercise machine during display of at least part of an exercise class on the first display, wherein the processor is configured to: receive, via a network, information indicative of a second performance parameter of a second user, the second performance parameter being detected at an additional exercise machine during display of the at least part of the exercise class on a display associated with the additional exercise machine, the additional exercise machine being located at location remote from the exercise machine, and cause the second performance parameter to be displayed on the first display together with the first performance parameter.

J: In the exercise machine of clause I, the processor is further configured to: receive, via the network and from a server, information about a plurality of available exercise classes, the plurality of exercise classes including the exercise class; cause the first display to display the information; and receive, from the first user and via the display, an input indicating selection of the exercise class.

K: In the exercise machine of clause I or J, the processor is further configured to: request digital content comprising the exercise class, from the server and via the network, at least partly in response to the input, the exercise class comprising a running class performed by an instructor at least partially on a treadmill.

L: In the exercise machine of clause I, J, or K, the sensor is configured to detect at least one of a speed of the belt and an incline of the deck relative to the support surface, and wherein the processor is configured to: determine an amount of energy expended by the first user while running during the at least part of the exercise class, and cause the amount of energy to be displayed on the first display together with the at least part of the exercise class.

M: In the exercise machine of clause I, J, K, or L, the processor is configured to cause the first display to display a segmented timeline together with the at least part of the exercise class, the segmented timeline including: a first segment corresponding to the at least part of the exercise class, and a first visual indicia indicating that the first user is to run during the at least part of the exercise class.

N: In the exercise machine of clause I, J, K, L, or M, the segmented timeline includes: a second segment corresponding to an additional part of the exercise class, and a second visual indicia indicating that the first user is to lift a weight during the additional part of the exercise class.

O: In the exercise machine of clause I, J, K, L, M, or N, the processor is configured to cause the first display to display a leaderboard together with the at least part of the exercise class, the leaderboard indicating: a plurality of additional users associated with the exercise class, a respective rank of each user of the plurality of additional users, and a respective amount of energy expended by each user of the plurality of additional users.

P: In the exercise machine of clause I, J, K, L, M, N, or O, the sensor is configured to detect a load applied to at least one of the belt, the deck, and a motor configured to drive rotation of the belt, and wherein the processor is configured to: determine, based at least partly on the load, that the first user has stepped off of the belt during the at least part of the exercise class, and cause a notification to be displayed on the first display together with the at least part of the exercise class, the notification indicating that the first user has stepped off of the belt.

Q: A method comprises causing at least part of an exercise class to be displayed on a first display associated with a first treadmill; receiving information indicative of a first performance parameter detected by a sensor associated with the first treadmill, the first performance parameter being associated with a first user running on a belt of the first treadmill during display of the at least part of the exercise class on the first display; receiving, via a network, information indicative of a second performance parameter associated with a second user, the second performance parameter being detected at a second treadmill during display of the at least part of the exercise class on a second display associated with the second treadmill, the second treadmill being located at location remote from the first treadmill; and causing the second performance parameter to be displayed on the first display together with the first performance parameter.

R: The method of clause Q, further comprises receiving a first input from the first user during display of the at least part of the exercise class on the first display, the first input being indicative of a request to change an incline of a deck of the first treadmill, the first treadmill including a belt rotatably connected to the deck; and activating a first motor located substantially internal to the deck at least partly in response to the first input.

S: The method of clause Q or R, further comprises receiving a second input from the first user during display of the at least part of the exercise class on the first display, the second input being indicative of a request to change a speed of the belt, the belt comprising a plurality of lateral slats; and activating a second motor located substantially internal to the deck at least partly in response to the second input.

T: The method of clause Q, R, or S, further comprises determining an amount of energy expended by the first user while running during the at least part of the exercise class; and causing the amount of energy to be displayed on the first display together with the at least part of the exercise class, and a segmented timeline, the segmented timeline including a first segment corresponding to the at least part of the exercise class, and a first visual indicia indicating that the first user is to run during the at least part of the exercise class.

CONCLUSION

The subject matter described above is provided by way of illustration only and should not be construed as limiting. Furthermore, the claimed subject matter is not limited to implementations that solve any or all disadvantages noted in any part of this disclosure. Various modifications and changes may be made to the subject matter described herein without following the examples and applications illustrated and described, and without departing from the spirit and scope of the present invention, which is set forth in the following claims.

What is claimed is:

1. A method, comprising:
    causing a first portion of an exercise class to be displayed on a first display of a first exercise machine;
    receiving information indicative of a first performance parameter, the first performance parameter being associated with a first user performing a first activity while the first portion of the exercise class is being displayed on the first display;
    receiving information indicative of a second performance parameter, the second performance parameter being associated with a second user performing the first activity while the first portion of the exercise class is being displayed on a second display of the second exercise machine; and
    during display of the first portion of the exercise class on the first display, causing the first performance parameter to be displayed on the first display together with the second performance parameter and a timeline corresponding to the exercise class, wherein the timeline includes:
        a first segment associated with the first portion of the exercise class, and
        a second segment separate from the first segment, the second segment associated with a second portion of the exercise class different from the first portion.

2. The method of claim 1, further comprising, during display of the first portion of the exercise class on the second display, causing the first performance parameter to be displayed on the second display together with the second performance parameter and the timeline.

3. The method of claim 1, wherein the timeline further comprises:
    first indicia indicative of the first activity and displayed in association with the first segment, and
    second indicia indicative of a second activity, different from the first activity, and displayed in association with the second segment.

4. The method of claim 3, wherein the first activity comprises an activity to be performed on the first exercise machine, and the second activity comprises an activity to be performed off of the first exercise machine.

5. The method of claim 1, wherein during display of the first portion of the exercise class on the first display, the first segment of the timeline is displayed on the first display together with an indication of:
    an elapsed time of the first portion of the exercise class, or
    a remaining time of the first portion.

6. The method of claim 1, wherein the timeline further comprises indicia indicative of equipment required for performance of the first activity, the indicia being displayed in association with the first segment.

7. The method of claim 1, wherein the timeline further comprises a component indicating a characteristic of a second portion of the exercise class, the second portion occurring after the first portion of the exercise class.

8. The method of claim 1, wherein the timeline further comprises a component providing information indicating how to perform the first activity.

9. The method of claim 1, wherein at least one of a size, position, color, and opacity of the first segment displayed on the first display is indicative of a length of the first portion of the exercise class.

10. The method of claim 1, wherein:
    the first exercise machine and second exercise machine comprise treadmills,
    the first exercise machine includes a first processor, and
    the information indicative of the first performance parameter is provided by the first processor, via a network, to a second processor disposed remote from the first exercise machine.

11. A system, comprising:
    a first exercise machine including a first processor, and a first display operably connected to the first processor; and
    a second processor remote from and in communication with the first processor, wherein the second processor is configured to:
        provide digital content of an exercise class to the first processor via a network;
        receive, from the first processor, information indicative of a first performance parameter, the first performance parameter being associated with a first user performing a first activity while a first portion of the exercise class is being displayed on the first display;
        receive, from a second exercise machine, information indicative of a second performance parameter, the second performance parameter being associated with a second user performing the first activity while the first portion of the exercise class is being displayed on a second display of the second exercise machine; and
        during display of the first portion of the exercise class on the first display, cause the first performance parameter to be displayed on the first display together with the second performance parameter and a timeline corresponding to the exercise class, wherein the timeline includes
  a first segment associated with the first portion of the exercise class,
  a second segment associated with a second portion of the exercise class different from the first segment, and
  first indicia indicative of the first activity and displayed in association with the first segment.

12. The system of claim 11, wherein the timeline further includes second indicia indicative of a second activity different from the first activity, the second indicia being displayed in association with the second segment.

13. The system of claim 12, wherein the second indicia indicates that the first user is to at least one of:
  lift weights during the second portion of the exercise class;
  walk during the second portion of the exercise class; or
  run during the second portion of the exercise class.

14. The system of claim 11, wherein the first performance parameter comprises at least one of:
  a speed of a belt associated with a deck of the first exercise machine,
  an incline of the deck, and
  a mile pace of the first user.

15. The system of claim 11, wherein the first performance parameter comprises an amount of energy expended by the first user, and wherein the amount of energy is determined based at least partly on:
  a speed of a belt associated with a deck of the first exercise machine, and
  an incline of the deck.

16. An exercise machine, comprising:
  a first processor;
  a first display operably connected to the first processor;
  a deck configured to move relative to a surface supporting the exercise machine; and
  a belt rotatable about the deck, wherein the first processor is configured to control a speed of the belt and an incline of the deck, and the first processor is in communication with a second processor disposed remote from the exercise machine, the first processor being configured to:
    receive digital content of an exercise class, from the second processor, via a network;
    control the first display to display the exercise class;
    provide information indicative of a first performance parameter to the second processor, the first performance parameter being associated with a first user performing a first activity while a first portion of the exercise class is being displayed on the first display;
    receive information indicative of a second performance parameter from the second processor, the second performance parameter being associated with a second user performing the first activity while the first portion of the exercise class is being displayed on a second display of a second exercise machine; and
    during display of the first portion of the exercise class on the first display, control the first display to display the first performance parameter together with the second performance parameter and a timeline corresponding to the exercise class, wherein the timeline includes
      a first segment associated with the first portion of the exercise class,
      a second segment associated with a second portion of the exercise class different from the first segment, and
      first indicia indicative of the first activity and displayed in association with the first segment.

17. The exercise machine of claim 16, wherein the exercise class comprises a live class streamed, by the second processor and via the network, to the first exercise machine and to the second exercise machine substantially in real-time.

18. The exercise machine of claim 16, wherein the first processor is further configured to:
  receive video chat data from the second processor and via the network; and
  control the first display to display the video chat data, in substantially real-time, together with the exercise class.

19. The exercise machine of claim 16, wherein the first processor is further configured to:
  control the first display to display a leaderboard during display of the first portion of the exercise class on the first display, the leaderboard indicating:
  a plurality of additional users associated with the exercise class,
  a respective rank of each user of the plurality of additional users, and
  a respective amount of energy expended by each user of the plurality of additional users.

20. The exercise machine of claim 16, wherein:
  the timeline further includes second indicia indicative of a second activity different from the first activity, the second indicia being displayed in association with the second segment, and
  at least one of the first activity and the second activity comprises an activity to be performed off of the first exercise machine.

* * * * *

UNITED STATES PATENT AND TRADEMARK OFFICE
CERTIFICATE OF CORRECTION

| | |
|---|---|
| PATENT NO. | : 11,400,344 B2 |
| APPLICATION NO. | : 17/120928 |
| DATED | : August 2, 2022 |
| INVENTOR(S) | : John Foley et al. |

It is certified that error appears in the above-identified patent and that said Letters Patent is hereby corrected as shown below:

In the Specification

In the Cross-Reference to Related Applications:
In Column 1, Line 6-7, change "application Ser. No." to --Patent Application No.--.

Signed and Sealed this
Eleventh Day of October, 2022

Katherine Kelly Vidal
*Director of the United States Patent and Trademark Office*